United States Patent
Wood et al.

(10) Patent No.: US 7,834,036 B2
(45) Date of Patent: Nov. 16, 2010

(54) FUSED-AROMATIC COMPOUNDS HAVING ANTI-DIABETIC ACTIVITY

(75) Inventors: Harold B. Wood, Westfield, NJ (US); Peter T. Meinke, Scotch Plains, NJ (US); Guo Q. Shi, Monmouth Junction, NJ (US); Yong Zhang, West Windsor, NJ (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 724 days.

(21) Appl. No.: 11/884,802

(22) PCT Filed: Mar. 3, 2006

(86) PCT No.: PCT/US2006/007740

§ 371 (c)(1), (2), (4) Date: Aug. 21, 2007

(87) PCT Pub. No.: WO2006/096564

PCT Pub. Date: Sep. 14, 2006

(65) Prior Publication Data

US 2008/0194586 A1    Aug. 14, 2008

Related U.S. Application Data

(60) Provisional application No. 60/658,661, filed on Mar. 4, 2005.

(51) Int. Cl.
*A61K 31/443* (2006.01)
*C07D 413/04* (2006.01)

(52) U.S. Cl. .................................... 514/338; 546/272.1

(58) Field of Classification Search ................. 514/338; 546/272.1
See application file for complete search history.

(56) References Cited

FOREIGN PATENT DOCUMENTS

| WO | WO 01/30343 | 5/2001 |
|---|---|---|
| WO | WO 01/060807 | 8/2001 |
| WO | WO 01/079197 | 10/2001 |
| WO | WO 02/08188 | 1/2002 |
| WO | WO 02/010137 | 2/2002 |
| WO | WO 02/064094 | 8/2002 |
| WO | WO 2004/014860 | 2/2004 |
| WO | WO 2004/019869 | 3/2004 |
| WO | WO 2004/020408 | 3/2004 |
| WO | WO 2004/020409 | 3/2004 |
| WO | WO 2006/033891 | 3/2006 |

*Primary Examiner*—Taofiq A Solola
(74) *Attorney, Agent, or Firm*—Janet E. Fair; John C. Todaro

(57) ABSTRACT

Fused aromatic compounds of Formula (I) are PPAR gamma agonists or partial agonists and are useful in the treatment or control of type II diabetes, including hyperglycemia, dyslipidermia, hyperlipidemia, hypercholesterolemia, hypertriglyceridemia, and obesity that are often associated with type 2 diabetes.

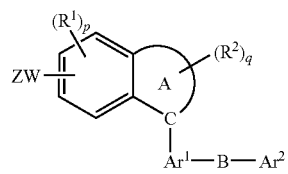

16 Claims, No Drawings

FUSED-AROMATIC COMPOUNDS HAVING ANTI-DIABETIC ACTIVITY

CROSS-REFERENCE TO RELATED APPLICATIONS

This application is a U.S. National Phase application under 35 U.S.C. §371 of PCT application No. PCT/US200/007740, filed Mar. 3, 2006, which claims priority under 35 U.S.C. §119 from U.S. provisional application No. 60/658,661, filed Mar. 4, 2005.

FIELD OF THE INVENTION

The instant invention is concerned with fused aromatics having one or more acid functional groups, including pharmaceutically acceptable salts and prodrugs thereof, which are useful as therapeutic compounds, particularly in the treatment of Type 2 diabetes mellitus, and of conditions that are often associated with this disease, including obesity and lipid disorders.

BACKGROUND OF THE INVENTION

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced in the body. Patients having type 2 diabetes often have hyperinsulinemia (elevated plasma insulin levels); however, these patients are insulin resistant, which means that they have a resistance to the effect of insulin in stimulating glucose and lipid metabolism in the main insulin-sensitive tissues, which are muscle, liver and adipose tissues. Patients who are insulin resistant but not diabetic compensate for the insulin resistance by secreting more insulin, so that serum glucose levels are not elevated enough to meet the criteria of Type 2 diabetes. In patients with Type 2 diabetes, even elevated plasma insulin levels are insufficient to overcome the pronounced insulin resistance.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Many patients who have insulin resistance or Type 2 diabetes often have several symptoms that together are referred to as syndrome X, or the metabolic syndrome. A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

Insulin resistance is, not primarily caused by a diminished number of insulin receptors but by a post-insulin receptor binding defect that is not yet completely understood. This lack of responsiveness to insulin results in insufficient insulin-mediated activation of uptake, oxidation and storage of glucose in muscle and inadequate insulin-mediated repression of lipolysis in adipose tissue and of glucose production and secretion in the liver.

There are several available treatments for type 2 diabetes, each of which has its own limitations and potential risks. Physical exercise and a reduction in dietary intake of calories often dramatically improve the diabetic condition and are the best first line treatment of type 2 diabetes. Compliance with this treatment is very poor because of well-entrenched sedentary lifestyles and excess food consumption. A widely used drug treatment involves the administration of a sulfonylurea (e.g. tolbutamide or glipizide) or a meglitinide (e.g. repaglinide or nateglinide), which are insulin secretagogues. These drugs increase the plasma level of insulin by stimulating the pancreatic β-cells to secrete more insulin. The insulin secretagogues, especially the sulfonylureas, must be administered carefully, as they may cause insulin secretion regardless of whether insulin is needed to reduce serum glucose, so that the patient may develop hypoglycemia.

The biguanides are another class of drugs that are widely used to treat type 2 diabetes. The two best known biguanides, phenformin and metformin, cause some correction of hyperglycemia without risk of causing hypoglycemia. The biguanides can be used either with insulin or with an insulin secretagogue without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of type 2 diabetes. These agents substantially increase insulin sensitivity in muscle, liver and adipose tissue in several animal models of type 2 diabetes, resulting in partial or complete correction of elevated plasma glucose levels without the occurrence of hypoglycemia. The glitazones that are currently marketed (rosiglitazone and pioglitazone) are agonists of the peroxisome proliferator activated receptor (PPAR) gamma subtype. PPAR-gamma agonism is generally believed to be responsible for the improved insulin sensititization that is observed with the glitazones. New PPAR agonists are being developed for the treatment of Type 2 diabetes and/or dyslipidemia. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists), such as muraglitazar and tesaglitazar, are promising because they reduce hyperglycemia and also improve lipid metabolism.

The drug therapies described above often become less effective or ineffective over extended periods of time (years). Insulin is often administered after the other therapies have become ineffective.

PPAR agonists, and particularly glitazones, have had shortcomings which have so far detracted from their attractiveness. Some of the compounds, especially troglitazone, have exhibited liver toxicity. Troglitazone was eventually withdrawn from the marketplace because of hepatotoxicity. Another weakness in the currently marketed PPAR agonists is that monotherapy for type 2 diabetes produces only modest efficacy. The current compounds also do not greatly improve lipid metabolism, and may actually have a negative effect on the lipid profile. These shortcomings have provided an incentive to develop better insulin sensitizers for Type 2 diabetes which function via similar mechanism(s) of action.

Recently, there have been reports of compounds that are PPAR gamma antagonists or partial agonists. WO01/30343 describes a specific compound that is a PPAR partial agonist/antagonist that is useful for the treatment of obesity and Type 2 diabetes. WO02/08188, WO2004/020408, WO2004/020409, and WO2004/019869 disclose classes of PPAR agonists and partial agonists that are indole derivatives and that are useful in the treatment of Type 2 diabetes, with reduced side effects relating to body and heart weight gain. Fused aromatics as described herein have not been disclosed as having anti-diabetic activity.

SUMMARY OF THE INVENTION

The class of compounds described herein is a new class of PPAR-gamma agonists and partial agonists. The compounds are potent ligands of the PPAR gamma nuclear receptor. The class of compounds includes many compounds that are PPARγ partial agonists, but also may include PPARγ full agonists and/or PPARγ antagonists. Some compounds may also have PPARα activity in addition to PPARγ activity. The compounds are useful in the treatment and control of hyperglycemia and insulin resistance. The compounds are expected to be efficacious in the treatment of non-insulin dependent diabetes mellitus (NIDDM) in human and other mammalian patients, particularly in the treatment of hyperglycemia, and in the treatment of conditions associated with NIDDM, including hyperlipidemia, dyslipidemia, obesity, hypercholesterolemia, hypertriglyceridemia, atherosclerosis, vascular restenosis, inflammatory conditions, and other PPAR mediated diseases, disorders and conditions.

The compounds may also be useful in the treatment of one or more lipid disorders, including mixed or diabetic dyslipidemia, isolated hypercholesterolemia, which may be manifested by elevations in LDL-C and/or non-HDL-C, hyper-apoBliproteinemia, hypertriglyceridemia, an increase in triglyceride-rich-lipoproteins, and low HDL cholesterol concentrations. They may also be useful in the treatment or amelioration of atherosclerosis, obesity, vascular restenosis, inflammatory conditions, psoriasis, polycystic ovary syndrome, and other PPAR mediated diseases, disorders and conditions.

The present invention is directed to compounds having formula I, and pharmaceutically acceptable salts thereof:

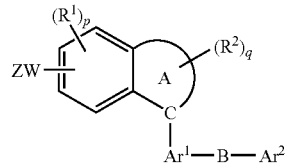

In Formula I, Ring A is a 5- or 6-membered aromatic or heteroaromatic ring having 1-2 heteroatoms independently selected from O, S, and N, where Ring A together with the phenyl ring to which ring A is fused forms a naphthalene or benzoheteroaromatic ring;

$Ar^1$ and $Ar^2$ are each carbocyclic or heterocyclic aromatic groups which are independently selected from the group consisting of phenyl, naphthyl, pyridinyl, pyrazinyl, and pyrimidinyl, said aromatic groups being optionally substituted with 1-4 substituent groups independently selected from halogen, —$C_1$-$C_6$ alkyl, —$C_2$-$C_6$ alkenyl, —$C_2$-$C_6$ alkynyl, —$OC_1$-$C_6$ alkyl, —$OC_2$-$C_6$ alkenyl, —C(=O)$C_1$-$C_6$ alkyl, —S(O)$_n C_1$-$C_6$ alkyl, $C_3$-$C_7$ cycloalkyl, —$OC_3$-$C_7$ cycloalkyl, —$NO_2$, and —CN, wherein —$C_1$-$C_6$ alkyl, —$C_2$-$C_6$ alkenyl, —$C_2$-$C_6$ alkynyl, —$OC_1$-$C_6$ alkyl, —$OC_2$-$C_6$ alkenyl, —C(=O) $C_1$-$C_6$ alkyl, —S(O)$_n C_1$-$C_6$ alkyl, $C_3$-$C_7$ cycloalkyl, and —$OC_3$-$C_7$ cycloalkyl are each optionally substituted with 1-5 halogens;

B is selected from the group consisting of —O—, —S(O)$_n$—, —N($R^3$)—, —C(=O)—, —C($R^4$)$_2$—, and —$C_{3-6}$ cycloalkylidene-;

—WZ is selected from the group consisting of —O—C($R^5$)($R^6$)-Z, —S(O)$_n$—C($R^5$)($R^6$)-Z, and —$CH_2$—C($R^5$)($R^6$)-Z;

Z is selected from the group consisting of —$CO_2 R^7$ and tetrazole;

$R^1$ and $R^2$ are each independently selected from the group consisting of halogen, —CN, —$NO_2$, —OH, —$C_1$-$C_5$ alkyl, —$OC_1$-$C_5$ alkyl, —C(=O)$C_1$-$C_5$ alkyl, —S(O)n$C_1$-$C_5$alkyl, and $C_{3-6}$ cycloalkyl, wherein $C_1$-$C_5$ alkyl, —$OC_1$-$C_5$ alkyl, —C(=O)$C_1$-$C_5$ alkyl, —S(O)$_n C_1$-$C_5$alkyl, and $C_{3-6}$ cycloalkyl are optionally substituted with 1-5 halogens;

$R^3$ is selected from the group consisting of H and $C_1$-$C_5$ alkyl;

Each $R^4$ is independently selected from the group consisting of H, halogen, and —$C_1$-$C_5$ alkyl, wherein —$C_1$-$C_5$ alkyl is optionally substituted with 1-5 halogens;

$R^5$ and $R^6$ are each independently selected from the group consisting of H, halogen, —$C_1$-$C_5$ alkyl, —$OC_1$-$C_5$ alkyl, —$C_2$-$C_5$ alkenyl, —$OC_2$-$C_5$ alkenyl, $C_{3-6}$ cycloalkyl, —(CH$_2$)$_m$phenyl, and —O(CH$_2$)$_m$phenyl, wherein —$C_1$-$C_5$ alkyl, —$OC_1$-$C_5$ alkyl, —$C_2$-$C_5$ alkenyl, and —$OC_2$-$C_5$ alkenyl are optionally substituted with 1-5 halogens, and wherein $C_{3-6}$ cycloalkyl and the phenyl of —(CH$_2$)$_m$phenyl and —O(CH$_2$)$_m$phenyl are optionally substituted with 1-5 groups independently selected from halogen, $C_1$-$C_3$ alkyl and —$OC_1$-$C_3$ alkyl, said $C_1$-$C_3$ allyl and —$OC_1$-$C_3$ alkyl being optionally substituted with 1-3 halogens; or alternatively $R^5$ and $R^6$ may be joined to form a $C_3$-$C_6$ cycloalkyl group, said $C_3$-$C_6$ cycloalkyl group optionally being substituted with 1-3 halogens;

$R^7$ is selected from the group consisting of H and —$C_1$-$C_6$ alkyl, wherein $C_1$-$C_6$ alkyl is optionally substituted with 1-5 halogens;

m in each instance is an integer from 0-2;

n in each instance is an integer from 0-2;

p is an integer from 0 to 3; and q is an integer from 0-3.

Note that "C" in ring A of formula I represents a carbon atom.

In the above definitions and subsequent definitions, alkyl groups may be either linear or branched, unless otherwise specified.

DETAILED DESCRIPTION OF THE INVENTION

The invention has numerous embodiments, as set forth below.

In one subset of compounds of Formula I, Ring A together with the phenyl ring to which ring A is fused forms a naphthalene ring or a benzoheteroaromatic ring selected from the group consisting of quinolyl, isoquinolyl, benzisoxazolyl, indolyl, indazolyl, benzofuryl, and benzothienyl.

In other subsets of compounds of Formula I:

Ring A together with the phenyl ring to which ring A is fused forms a naphthalene ring or a benzoheteroaromatic ring selected from the group consisting of quinolyl, benzisoxazolyl, indolyl, indazolyl, benzofuryl, and benzothienyl;

$Ar^1$ is selected from the group consisting of phenyl, pyrimidinyl, and pyridinyl, and $Ar^2$ is selected from the group consisting of phenyl and pyridinyl, where $Ar^1$ and $Ar^2$ are each optionally substituted with 1-4 substituent groups independently selected from halogen, —$C_1$-$C_4$ alkyl, —$OC_1$-$C_4$ alkyl, —$S(O)_nC_1$-$C_4$ alkyl, —$NO_2$, and —CN, wherein —$C_1$-$C_4$ alkyl, —$OC_1$-$C_4$ alkyl, and —$S(O)_nC_1$-$C_4$ alkyl are each optionally substituted with 1-3 halogens;

B is selected from —O— and —C(=O)—;

—WZ is —O—C($R^5$)($R^6$)—$CO_2R^7$;

$R^1$ and $R^2$ are each independently selected from the group consisting of halogen, —OH, —CN, —$NO_2$, —$C_1$-$C_3$ alkyl, —$OC_1$-$C_3$ alkyl, —$S(O)_2CH_3$, and —$S(O)_2CF_3$, wherein —$C_1$-$C_3$ alkyl and —$OC_1$-$C_3$ alkyl are optionally substituted with 1-3 halogens;

$R^5$ and $R^6$ are each independently selected from the group consisting of H, halogen, and —$C_1$-$C_4$ alkyl, wherein —$C_1$-$C_4$ alkyl is optionally substituted with 1-5 halogens;

$R^7$ is selected from the group consisting of H and $C_1$-$C_6$ alkyl, wherein $C_1$-$C_6$ alkyl is optionally substituted with 1-5 halogens;

n is an integer from 0-2;

p is an integer from 0 to 2; and q is an integer from 0-2.

In subsets of the compounds of this invention, Ring A together with the phenyl ring to which ring A is fused forms a naphthalene ring or a benzoheteroaromatic ring selected from the group consisting of benzisoxazolyl, indolyl, indazolyl, benzofuryl, and benzothienyl.

In subsets of this invention, $Ar^1$ and $Ar^2$ are each independently selected from the group consisting of phenyl and pyridinyl, which are each optionally substituted with 1-4 substituent groups independently selected from halogen, —$C_1$-$C_4$ alkyl, —$OC_1$-$C_4$ alkyl, —$S(O)_nC_1$-$C_4$ alkyl, —$NO_2$, and —CN, wherein —$C_1$-$C_4$ alkyl, —$OC_1$-$C_4$ alkyl, and —$S(O)nC_1$-$C_4$ alkyl are each optionally substituted with 1-3 halogens.

In subsets of compounds of Formula I, Ring A together with the phenyl ring to which ring A is fused forms a naphthalene ring or a benzoheteroaromatic ring selected from the group consisting of benzisoxazolyl, indazolyl, and benzofuryl.

In subsets of compounds of Formula I, $Ar^1$ is selected from the group consisting of phenyl and pyridinyl, and is optionally substituted with 1-2 groups which are independently selected from $C_1$-$C_4$ alkyl, wherein $C_1$-$C_4$ alkyl is optionally substituted with 1-3 halogens.

In subsets of compounds of Formula I, $Ar^2$ is phenyl, which is optionally substituted with 1-2 substituent groups independently selected from halogen, —CN, —$C_1$-$C_3$ alkyl, and —$OC_1$-$C_3$ alkyl, wherein —$C_1$-$C_3$ alkyl and —$OC_1$-$C_3$ alkyl are optionally substituted with 1-3 halogens.

In subsets of compounds of Formula I, B is —O—. In subsets of compounds of Formula I, B is —C(=O)—. In subsets of compounds of Formula I, B is —C(=O)— or —O—.

In subsets of compounds of Formula I, —WZ is —O—C($R^5$)($R^6$)—$CO_2H$.

In subsets of compounds of Formula I, each $R^1$ is independently selected from the group consisting of halogen, —$C_1$-$C_3$ alkyl, and —OH, wherein —$C_1$-$C_3$ alkyl is optionally substituted with 1-3 halogens.

In subsets of compounds of Formula I, each $R^2$ is independently selected from the group consisting of —$C_1$-$C_3$ alkyl, —$S(O)_2CH_3$, and —$S(O)_2CF_3$, wherein —$C_1$-$C_3$ alkyl is optionally substituted with 1-3 halogens.

In subsets of compounds of Formula I, $R^5$ and $R^6$ are each H or —$C_1$-$C_3$ alkyl.

In subsets of the compounds of the invention, q and p are each independently integers from 0-2. In subsets of the compounds of the invention, q is an integer which is 0 or 1. In subsets of the compounds of the invention, p is an integer which is 0 or 1.

A preferred subset of compounds as described above has Formula II, wherein

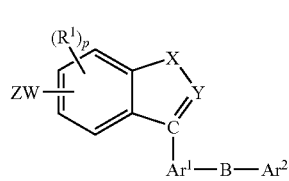

X—Y is —O—N=, —N($R^2$)—N=, —O—C($R^2$)=, —S—C($R^2$)=, or —N($R^2$)—(C$R^2$)=, and the other substituent groups are as defined previously.

In many preferred compounds having Formula II, $Ar^1$ is selected from the group consisting of phenyl, pyrimidinyl, and pyridinyl, and is optionally substituted with 1-2 groups which are independently selected from $C_1$-$C_4$ alkyl, wherein $C_1$-$C_4$ alkyl is optionally substituted with 1-3 halogens;

$Ar^2$ is phenyl, which is optionally substituted with 1-2 substituent groups independently selected from halogen, —CN, —$C_1$-$C_3$ alkyl, and —$OC_1$-$C_3$ alkyl, wherein —$C_1$-$C_3$ alkyl and —$OC_1$-$C_3$ alkyl are optionally substituted with 1-3 halogens;

B is selected from —O— and —C(=O)—;

—WZ is —O—C($R^5$)($R^6$)—$CO_2R^7$;

Each $R^1$ is independently selected from the group consisting of halogen, —$C_1$-$C_3$ alkyl, —$OC_1$-$C_3$ alkyl, and —OH, wherein —$C_1$-$C_3$ alkyl and —$OC_1$-$C_3$ alkyl are optionally substituted with 1-3 halogens;

Each $R^2$ is independently selected from the group consisting of H, —$C_1$-$C_3$ alkyl, —$S(O)_2CH_3$, and —$S(O)_2CF_3$, wherein —$C_1$-$C_3$ alkyl is optionally substituted with 1-3 halogens;

$R^5$ and $R^6$ are each independently selected from the group consisting of H and $C_1$-$C_3$ alkyl, wherein —$C_1$-$C_3$ alkyl is optionally substituted with 1-5 halogens;

$R^7$ is H or —$C_1$-$C_5$ alkyl; and p is an integer from 0-2.

In subsets of the compounds of the invention, $Ar^1$ is selected from the group consisting of phenyl and pyridinyl, and is optionally substituted with 1-2 groups which are independently selected from $C_1$-$C_4$ alkyl, wherein $C_1$-$C_4$ alkyl is optionally substituted with 1-3 halogens.

Many preferred compounds defined by Formula I and II above have Formula III below:

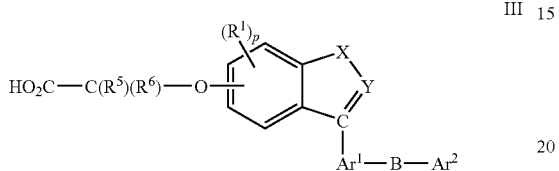

III

In these compounds, X—Y is selected from the group consisting of —O—N=, —N($R^2$)—N=, and —O—C($R^2$)=;

$Ar^1$ is selected from the group consisting of phenyl, pyrimidinyl, and pyridinyl, wherein $Ar^1$ is optionally substituted with a —$C_2$-$C_4$ alkyl group, which is optionally substituted with 1-3 F;

Each $R^1$ is independently selected from the group consisting of halogen, $CH_3$, —$CF_3$, —OH, —$OCH_3$, and —$OCF_3$;

$R^2$ is selected from the group consisting of H, —$C_1$-$C_3$ alkyl, —$CF_3$, —$S(O)_2CH_3$, and —$S(O)_2CF_3$;

$R^5$ is H or —$C_1$-$C_3$ alkyl; and $R^6$ is —$C_1$-$C_3$ alkyl.

In subsets of the compounds, $Ar^1$ is phenyl or pyridinyl, wherein $Ar^1$ is optionally substituted with a —$C_2$-$C_4$ alkyl group, which is optionally substituted with 1-3 F; or is substituted as defined elsewhere.

In subsets of compounds described above having formula I, II or III, $Ar^1$ is selected from the group consisting of phenyl, pyrimidinyl, and pyridinyl, wherein pyridinyl is connected through the 3-position to the C-atom of the ring A to which $Ar^1$ is connected, pyrimidinyl is connected through the 5-position to the C-atom of the ring A to which $Ar^1$ is connected, and $Ar^1$ is substituted with one —$C_2$-$C_4$ alkyl substituent.

In subsets of compounds described above having formula I, II or III, $Ar^2$ is phenyl, which is optionally substituted with 1-2 substituent groups independently selected from halogen, —CN, —$C_1$-$C_2$ alkyl, —$CF_3$, —$OCH_3$, and —$OCF_3$.

In subsets of compounds described above having formula I, II or III, B is —O—.

In subsets of compounds described above having formula I, II or III, each $R^1$ is independently selected from the group consisting of halogen, —$CH_3$, —$CF_3$, and —OH.

In subsets of compounds described above having formula I, II or III, $R^2$ is selected from the group consisting of H, —$CH_3$, —$CF_3$, —$S(O)_2CH_3$, and —$S(O)_2CF_3$.

In subsets of compounds described above having formula I, II or III, $R^5$ is H or —$CH_3$.

In subsets of compounds described above having formula I, II or III, $R^6$ is —$C_1$-$C_3$ alkyl.

In subsets of compounds described above, $Ar^1$ is selected from the group consisting of phenyl and pyridinyl, wherein pyridinyl is connected at the 3-position to the C-atom of the ring A to which $Ar^1$ is connected, and $Ar^1$ is substituted with one —$C_2$-$C_4$ alkyl substituent which is optionally substituted with 1-3 F; or in other subsets, $Ar^1$ is substituted with one —$C_2$-$C_4$ alkyl substituent which is not substituted further; or in other subsets, $Ar^1$ is substituted with one group n-propyl.

Other subsets comprise compounds having Formula IV, including pharmaceutically acceptable salts thereof:

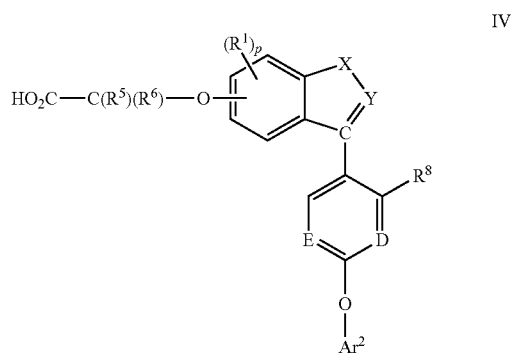

IV where D and E are each independently selected from —CH= and —N=; and $R^8$ is —$C_2$-$C_4$ alkyl, which is optionally substituted with 1-3 F. Other substituents may have any of the definitions described previously. In other subsets, $R^8$ is —$C_2$-$C_4$ alkyl, which is not further substituted. In other subsets, $R^8$ is n-propyl.

Other subsets comprise compounds having Formula V, including pharmaceutically acceptable salts thereof:

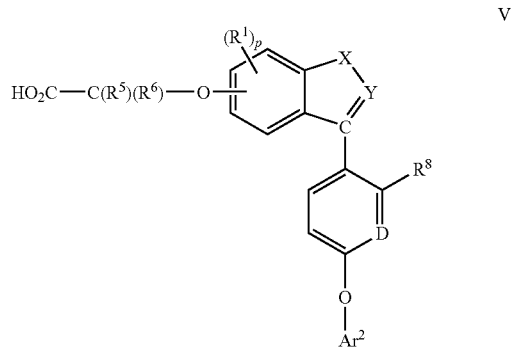

V where D is —CH= or —N=; and $R^8$ is —$C_2$-$C_4$ alkyl, which is optionally substituted with 1-3 F.

Other subsets comprise compounds having Formula VI below, including pharmaceutically acceptable salts thereof:

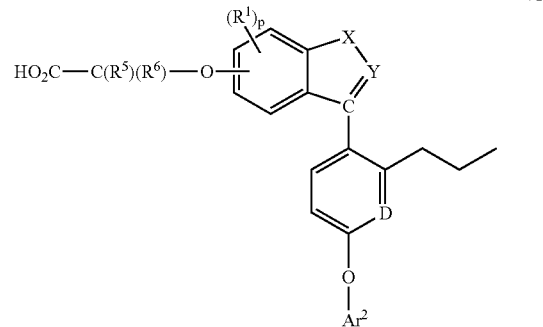

VI

In these compound, the definitions are as defined previously, and as follows:

D is —CH= or —N=;
R² is H, —CH₃, or —S(O)₂CH₃; and
R⁶ is C₁-C₂ alkyl.

Subsets of the compounds described above having Formula IV, V or VI comprise compounds in which X—Y is —O—N=, and D is —CH=.

Subsets of the compounds described above having Formula IV, V or VI comprise compounds in which X—Y is —O—N=, and D is —N=.

The invention includes compounds of Formula I, II, III, IV, V and VI, including pharmaceutically acceptable salts of these compounds, prodrugs of these compounds, and pharmaceutical compositions comprising these compounds and a pharmaceutically acceptable carrier. Disclosure herein relating to compounds of Formula I or the compound of Formula I also is meant to include all subsets of Formula I, including Formula II, III, IV, V and VI, as well as specific compounds disclosed herein.

Structures of specific compounds and synthetic procedures are disclosed in the examples and in Table 1. The specific compounds of the invention include the compounds provided in the Examples and in Table 1, and pharmaceutically acceptable salts thereof.

TABLE 1

| Example | Chemical Name | Structure |
|---------|---------------|-----------|
| 1 | (2S)-2-({3-[4-(4-chlorophenoxy)-2-propylphenyl]-1-benzofuran-5-yl}oxy)propanoic acid | 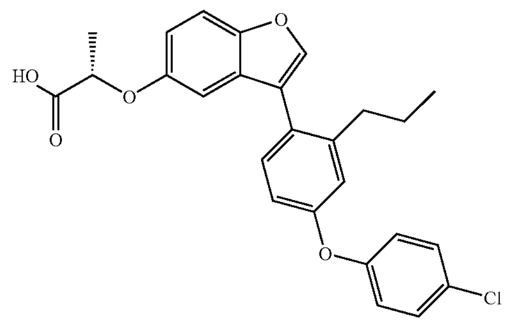 |
| 2 | (2S)-2-({6-chloro-3-[4-(4-chlorophenoxy)-2-propylphenyl]-1-benzofuran-5-yl}oxy)propanoic acid | 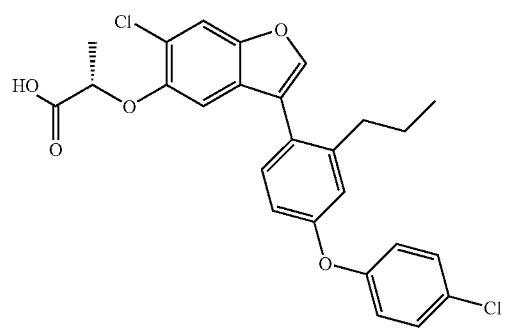 |
| 3 | (2S)-2-({3-[4-(4-chlorophenoxy)-2-propylphenyl]-1,2-benzisoxazol-5-yl}oxy)propanoic acid | 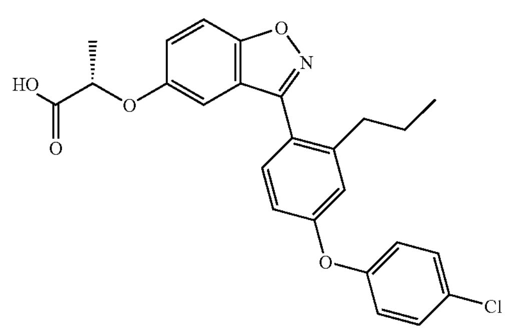 |

TABLE 1-continued

| Example | Chemical Name | Structure |
|---|---|---|
| 4 | (2S)-2-({4-chloro-3-[4-(4-chlorophenoxy)-2-propylphenyl]-1,2-benzisoxazol-5-yl}oxy)propanoic acid | 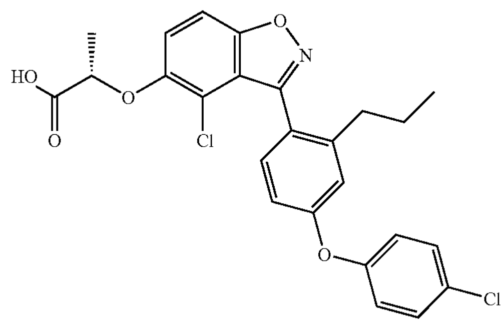 |
| 5 | (2R)-2-({6-chloro-3-[4-(4-chlorophenoxy)-2-propylphenyl]-1,2-benzisoxazol-5-yl}oxy)propanoic acid | 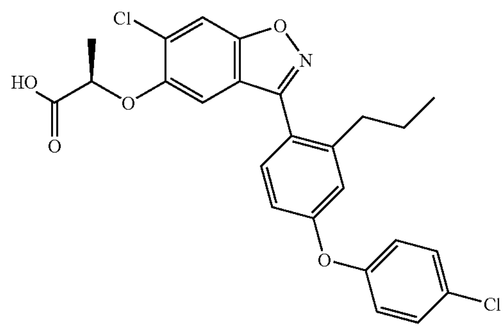 |
| 6 | (2S)-2-({6-chloro-3-[4-(4-chlorophenoxy)-2-propylphenyl]-1,2-benzisoxazol-5-yl}oxy)propanoic acid | 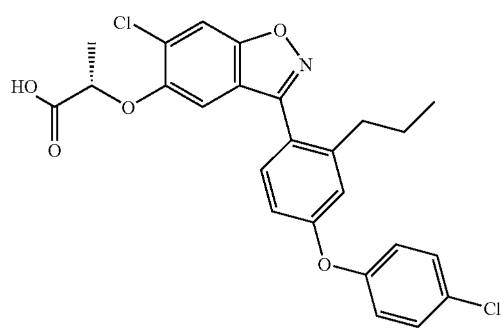 |
| 7 | (2S)-2-({6-chloro-3-[4-(4-methylphenoxy)-2-propylphenyl]-1,2-benzisoxazol-5-yl}oxy)propanoic acid | 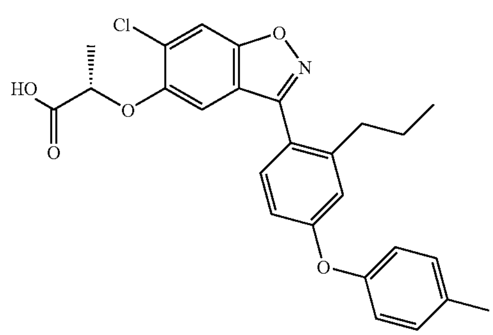 |

TABLE 1-continued

| Example | Chemical Name |
|---|---|
| 8 | (2S)-2-({6-chloro-3-[4-(4-ethylphenoxy)-2-propylphenyl]-1,2-benzisoxazol-5-yl}oxy)propanoic acid |
| 9 | (2S)-2-[(6-chloro-3-{2-propyl-4-[4-(trifluoromethoxy)phenoxy]phenyl}-1,2-benzisoxazol-5-yl)oxy]propanoic acid |
| 10 | (2S)-2-({6-chloro-3-[4-(3-chlorophenoxy)-2-propylphenyl]-1,2-benzisoxazol-5-yl}oxy)propanoic acid |
| 11 | (2S)-2-({6-chloro-3-[4-(3-chloro-4-methylphenoxy)-2-propylphenyl]-1,2-benzisoxazol-5-yl}oxy)propanoic acid |

TABLE 1-continued

| Example | Chemical Name | Structure |
|---------|---------------|-----------|
| 12 | ({6-chloro-3-[6-(4-chlorophenoxy)-2-propylpyridin-3-yl]-1,2-benzisoxazol-5-yl}oxy)acetic acid | 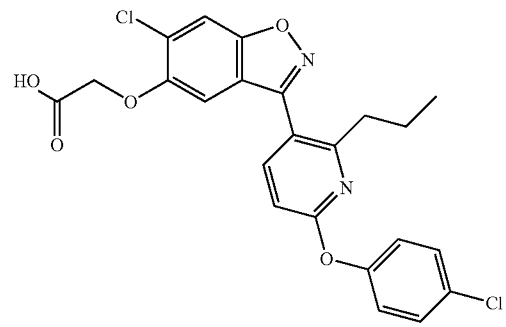 |
| 13 | 2-({6-chloro-3-[6-(4-chlorophenoxy)-2-propylpyridin-3-yl]-1,2-benzisoxazol-5-yl}oxy)butanoic acid | 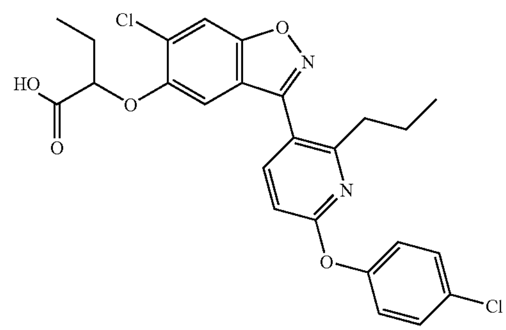 |
| 14 | (2S)-2-({6-chloro-3-[6-(4-chlorophenoxy)-2-propylpyridin-3-yl]-1,2-benzisoxazol-5-yl}oxy)propanoic acid | 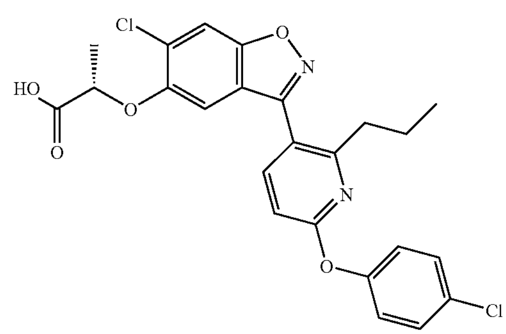 |
| 15 | (2S)-2-({6-chloro-3-[6-(4-fluorophenoxy)-2-propylpyridin-3-yl]-1,2-benzisoxazol-5-yl}oxy)propanoic acid | 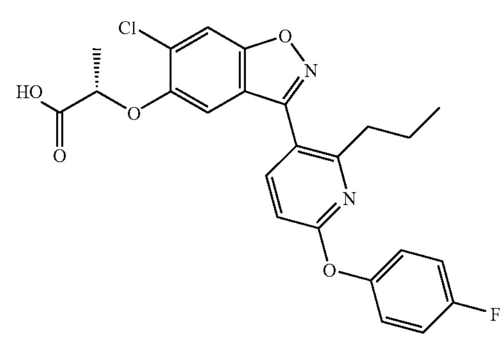 |

TABLE 1-continued

| Example | Chemical Name | Structure |
|---|---|---|
| 16 | (2S)-2-{[6-chloro-3-(6-phenoxy-2-propylpyridin-3-yl)-1,2-benzisoxazol-5-yl]oxy}propanoic acid | 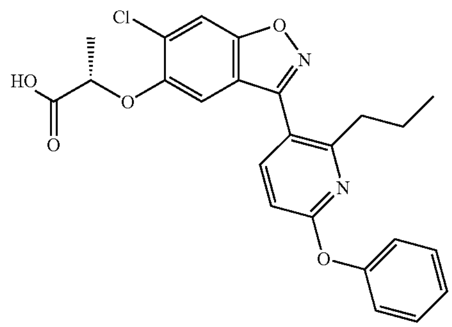 |
| 17 | (2R)-2-({6-chloro-3-[6-(4-chlorophenoxy)-2-propylpyridin-3-yl]-1,2-benzisoxazol-5-yl}oxy)propanoic acid | 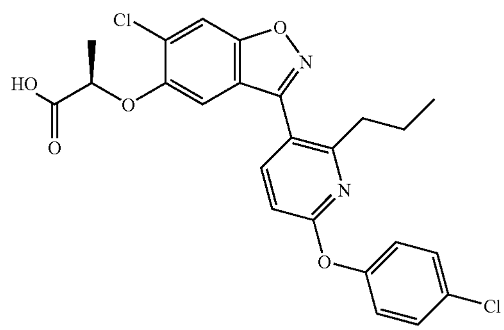 |
| 18 | (2S)-2-({6-chloro-3-[6-(4-cyanophenoxy)-2-propylpyridin-3-yl]-1,2-benzisoxazol-5-yl}oxy)propanoic acid | 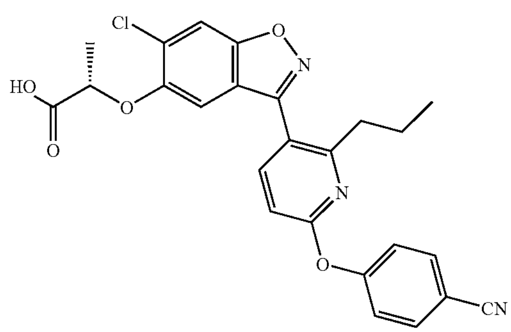 |
| 19 | (2S)-2-({6-chloro-3-[6-(4-chlorophenoxy)pyridin-3-yl]-1,2-benzisoxazol-5-yl}oxy)propanoic acid | 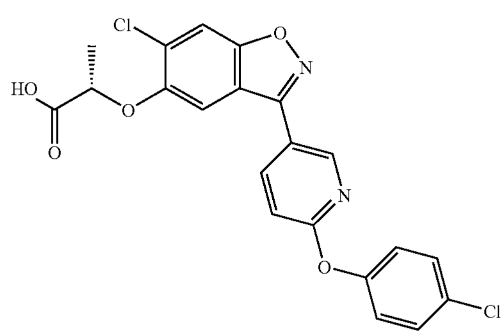 |

TABLE 1-continued

| Example | Chemical Name | Structure |
|---|---|---|
| 20 | (2S)-2-({6-chloro-3-[6-(4-chlorophenoxy)-2-propylpyridin-3-yl]-1-methyl-1H-indazol-5-yl}oxy)propanoic acid | 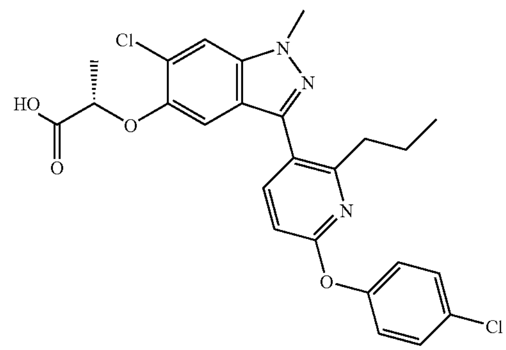 |
| 21 | (2S)-2-({6-chloro-3-[6-(4-chlorophenoxy)-2-propylpyridin-3-yl]-1H-indazol-5-yl}oxy)propanoic acid | 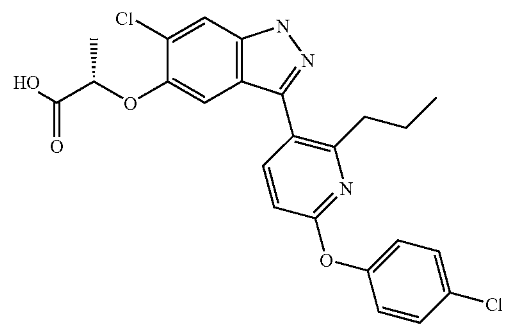 |
| 22 | (2S)-2-{[6-chloro-3-[6-(4-chlorophenoxy)-2-propylpyridin-3-yl]-1-(methylsulfonyl)-1H-indazol-5-yl]oxy}propanoic acid | 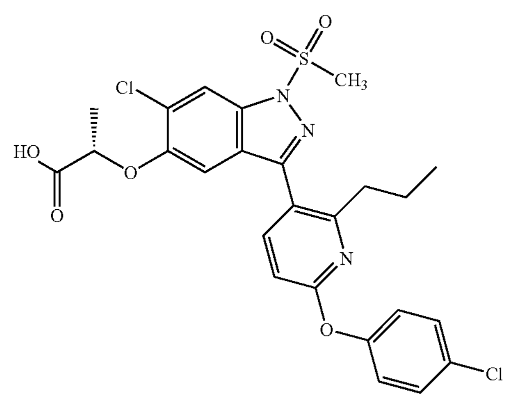 |
| 23 | (2S)-2-({8-[4-(4-fluorobenzoyl)phenyl]-2-naphthyl}oxy)propanoic acid | 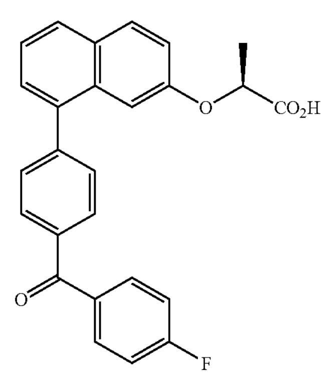 |

TABLE 1-continued

| Example | Chemical Name | Structure |
|---------|---------------|-----------|
| 24 | ({8-[2-(4-chlorophenoxy)pyrimidin-5-yl]-2-naphthyl}oxy)acetic acid | 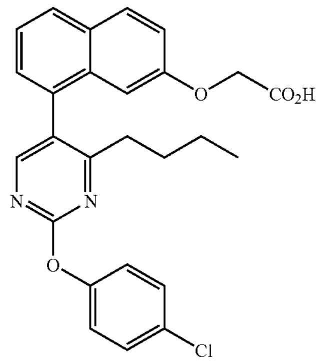 |

20

Table 2 provides additional specific compounds, including pharmaceutically acceptably salts thereof, that can be readily made using the procedures in this application by a practitioner in the field of synthetic organic chemistry.

TABLE 2

| Example | Chemical Name | Structure |
|---------|---------------|-----------|
| 2-1 | 2-({8-[4-(4-fluorobenzoyl)phenyl]-2-naphthyl}oxy)-2-methylpropanoic acid | 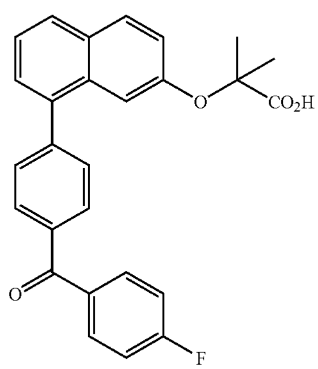 |
| 2-2 | 2-({8-[4-(4-methoxybenzoyl)phenyl]-2-naphthyl}oxy)-2-methylpropanoic acid | 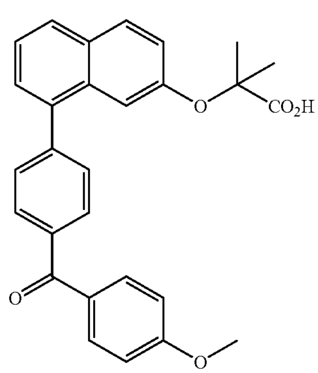 |

TABLE 2-continued

| Example | Chemical Name | Structure |
|---|---|---|
| 2-3 | (2R)-2-({8-[4-(4-fluorophenoxy)phenyl]-2-naphthyl}oxy)propanoic acid | 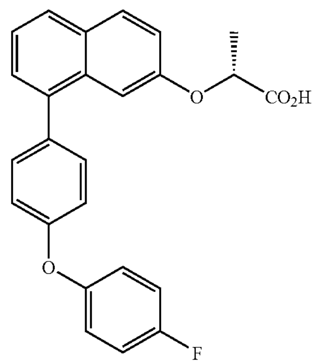 |
| 2-4 | (2S)-2-({8-[4-(4-fluorophenoxy)phenyl]-2-naphthyl}oxy)propanoic acid | 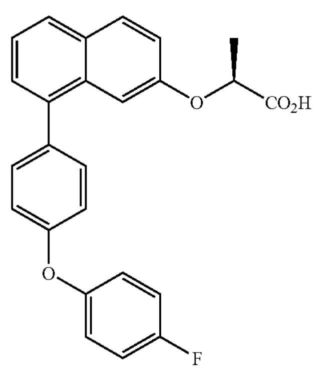 |
| 2-5 | 2-({8-[4-(4-fluorophenoxy)phenyl]-2-naphthyl}oxy)-2-methylpropanoic acid | 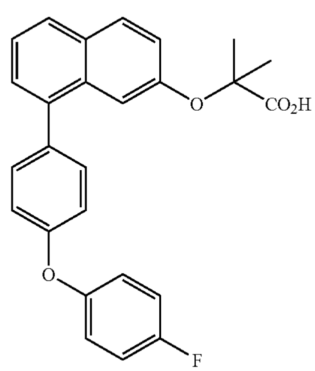 |
| 2-6 | 2-({8-[4-(4-fluorophenoxy)-3-propylphenyl]-2-naphthyl}oxy)-2-methylpropanoic acid | 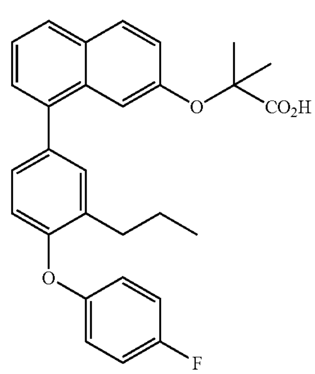 |

TABLE 2-continued

| Example | Chemical Name | Structure |
|---|---|---|
| 2-7 | (2S)-2-({8-[4-(4-fluorophenoxy)-3-propylphenyl]-2-naphthyl}oxy)propanoic acid | 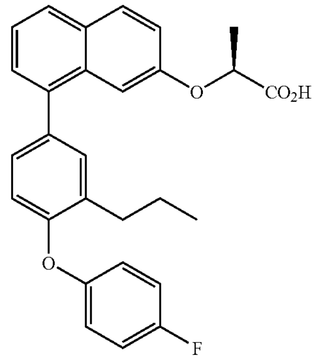 |
| 2-8 | 2-({3-[4-4-chlorophenoxy]-2-propylphenyl}-1,2-benzisoxazol-5-yl)oxy)propanoic acid | 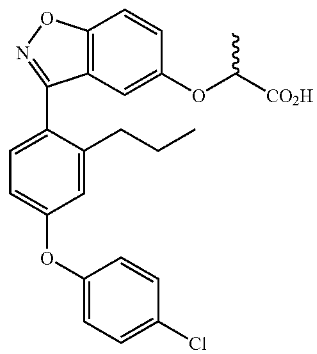 |
| 2-9 | (2S)-2-({6-chloro-3-[4-(4-fluorophenoxy)-2-propylphenyl]-1,2-benzisoxazol-5-yl}oxy)propanoic acid | 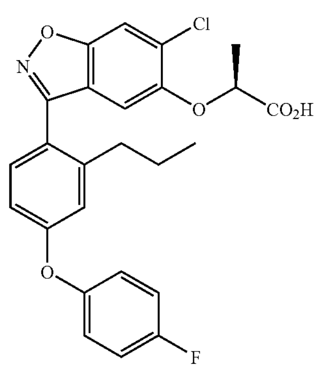 |
| 2-10 | (2S)-2-({6-chloro-3-[6-(4-chlorophenoxy)-2-propylpyridin-3-yl]-4-iodo-1,2-benzisoxazol-5-yl}oxy)propanoic acid | 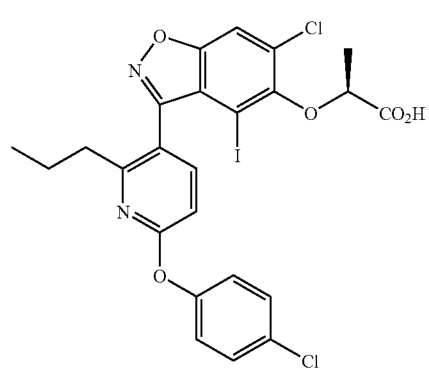 |

The compounds of this invention can be used in pharmaceutical compositions comprising the compound or a pharmaceutically acceptable salt thereof and a pharmaceutically acceptable carrier, optionally with one or more additional other active pharmaceutical ingredients. The compounds of this invention can be used in pharmaceutical compositions in which a compound of Formula I, or a pharmaceutically acceptable salt thereof, is the only active ingredient.

The compounds of the invention and pharmaceutically acceptable salts thereof are suitable for use in the manufacture of medicaments for the treatment of type 2 diabetes mellitus in a human or other mammalian patient, and in the manufacture of medicaments for other diseases described below that are treated by the compounds. The preferred patient is human.

The compounds as defined above may be used in any of the following methods to treat or control diseases, as well as methods to treat other diseases not listed below, in a mammalian patient, especially a human, by administering to the patient a therapeutically effective amount for the specific disease of a compound of Formula I:

(1) non-insulin dependent diabetes mellitus (type 2 diabetes);
(2) hyperglycemia;
(3) metabolic syndrome;
(4) obesity;
(5) hypercholesterolemia;
(6) hypertriglyceridemia; and/or
(7) one or more lipid disorders, including mixed or diabetic dyslipidemia, low HDL cholesterol, high LDL cholesterol, hyperlipidemia, hypercholesterolemia, and hypertriglyceridemia.

The compounds may also be used in a method for reducing the risks of adverse sequelae associated with metabolic syndrome in a human or other mammalian patient in need of such treatment which comprises administering to the patient a therapeutically effective amount of a compound of Formula I, or a pharmaceutically acceptable salt thereof.

The compounds may also be used in a method for treating atherosclerosis, for reducing the risk of developing atherosclerosis, for delaying the onset of atherosclerosis, and/or reducing the risk of sequelae of atherosclerosis in a human or other mammalian patient in need of such treatment or at risk of developing atherosclerosis or sequelae of atherosclerosis, which comprises administering to the patient a therapeutically effective amount of a compound of Formula I. Sequelae of atherosclerosis include for example angina, claudication, heart attack, stroke, etc.

The compounds are especially useful in the treatment of the following diseases, by administering a therapeutically effective amount (for the speciofic disease) of the compound, or a pharmaceutically acceptable salt thereof, to a patient in need of treatment:

(1) type 2 diabetes, and especially hyperglycemia resulting from type 2 diabetes;
(2) metabolic syndrome;
(3) obesity; and
(4) hypercholesterolemia.

Definitions

"Ac" is acetyl, which is $CH_3C(O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring system having a specified number of rings and a specified ring size (e.g. monocyclic 3-7-membered ring). A cycloalkyl can be fused to an aryl group. Examples of cycloalkyl include cyclopropyl, cyclopentyl, cyclohexyl, cycloheptyl, and the like. A cycloalkyl fused to an aromatic ring can be for example an indane ring or a tetrahydronaphthalene ring.

A cycloalkylidene group is a divalent cycloalkane radical in which both attachments are at the same carbon. For example, the cyclopropyl group of 1,1-dimethylcyclopropane is a cyclopropylidene group.

"Aryl" (and "arylene") when used to describe a substituent or group in a structure means an aromatic carbocyclic ring system having a specified number of rings and a specified ring size, as for example, a monocyclic or bicyclic aromatic system having 5-7-membered rings. Typical aryl groups include phenyl and naphthyl. Phenyl is generally the most preferred aromatic group. An aryl group can be fused to a cycloalkyl or heterocycle. "Heterocyclic" and "heterocycle" means a fully or partially saturated ring system containing a specified number of heteroatoms, a specified number of rings, and a specified ring size (e.g., heterocyclic monocyclic rings having 1-3 heteroatoms independently selected from N, S and O, each of said rings having 5-7 atoms). Examples of an aryl ring fused to heterocyclic groups include 2,3-dihydrobenzofuranyl, dihydrobenzopyranyl, and the like. Examples of monocyclic heterocycles include tetrahydrofuran, piperazine, and morpholine.

"Fused" has the meaning commonly used in organic chemistry. Two carbocyclic and/or heterocyclic rings are fused if they share a common side, as exemplified in the definitions of benzoheteroaryl and aryl.

"Heteroaryl" or "heterocyclic aromatic" means a mono- or polycyclic aromatic ring system containing a specified number of heteroatoms, a specified number of rings, and a specified ring size (e.g. a monocyclic ring having 1-3 heteroatoms independently selected from N, O and S, including —S(O)— and —$S(O)_2$—, with each ring containing 5 to 6 atoms). Examples of monocyclic heteroaryls include pyrrolyl, isoxazolyl, isothiazolyl, pyrazolyl, pyridinyl, oxazolyl, oxadiazolyl, thiadiazolyl, thiazolyl, imidazolyl, triazolyl, tetrazolyl, furanyl, triazinyl, thienyl, pyrimidinyl, pyridazinyl, and pyrazinyl.

"Benzoheteroaryl" or "benzoheteroaromatic" refers to bicyclic rings comprising a phenyl ring fused to a monocyclic heteroaromatic ring. Examples of benzoheteroaryl include benzisoxazolyl, benzoxazolyl, benzisothiazolyl, benzothiazolyl, benzimidazolyl, benzofuryl, benzothienyl (including S-oxide and dioxide), quinolyl, isoquinolyl, indazolyl, indolyl, and the like.

"Halogen" includes fluorine, chlorine, bromine and iodine.

"Me" represents methyl.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to comprehend all such isomeric forms of the compounds of Formula I.

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using starting materials and/or reagents that are optically pure and/or have a known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic or has a basic group in the structure, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Preferred acids include citric, hydrobromic, hydrochloric, maleic, phosphoric, sulfuric, tartaric, and benzenesulfonic acids. In some instances the compounds of the invention may be present in zwitterionic forms.

It will be understood that, as used herein, references to the compounds of Formula I are meant to also include the pharmaceutically acceptable salts.

Metabolites—Prodrugs

Metabolites of the claimed compounds which themselves fall within the scope of the claimed invention are also compounds of the current invention. Prodrugs, which are compounds that are converted to the claimed compounds as they are being administered to a patient or after they have been administered to a patient, also may be considered compounds of this invention.

Utilities

Compounds of the present invention are potent ligands having agonist, partial agonist or antagonist activity on one or more of the various peroxisome proliferator activated receptor subtypes, particularly PPARγ. The compounds may also be ligands or agonists, partial agonists or antagonists of the PPARα subtype as well as the PPARγ subtype, resulting in mixed PPARα/γ agonism. Some compounds (generally less preferred) may also be PPARδ ligands and have PPARδ activity in addition to their other PPAR activity. The compounds of this invention are useful in treating or controlling diseases, disorders or conditions which are mediated by one or more ligands of the individual PPAR subtypes (eg. γ or α) or a combination of PPAR subtypes (e.g. α/γ). One aspect of the present invention provides a method for the treatment and control of diseases that can be mediated by administration of a PPAR agonist or partial agonist, particularly a PPARγ agonist or partial agonist, such as type 2 diabetes. One aspect of the present invention provides a method for the treatment and control of diseases, disorders, or conditions which are mediated by one or more PPAR subtypes in a mammal which comprises administering to such a mammal a therapeutically effective amount of a compound of Formula I, or a pharmaceutically acceptable salt thereof. Compounds of the present invention may be useful in treating or controlling many PPAR mediated diseases and conditions, including, but not limited to, (1) diabetes mellitus, and especially non-insulin dependent diabetes mellitus (NIDDM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) psoriasis, (23) metabolic syndrome, (24) ovarian hyperandrogenism (polycystic ovarian syndrome), and other disorders where insulin resistance is a component. They may also have utility in treating high blood pressure, neoplastic conditions, adipose cell tumors, adipose cell carcinomas, such as liposarcoma, prostate cancer and other cancers, including gastric, breast, bladder and colon cancers, angiogenesis, and Alzheimer's disease.

The present compounds can be used to lower glucose, lipids, and insulin in non-diabetic patients who have impaired glucose tolerance and/or are in a pre-diabetic condition by the administration to a patient in need of treatment a therapeutically effective amount of a compound having Formula I, or pharmaceutically acceptable salt thereof.

The present compounds can be used to treat obesity in a patient in need of such treatment by administering to the patient a therapeutically effective amount of a compound of Formula I, or pharmaceutically acceptable salt thereof.

The present compounds can be used to treat or reduce the risk of developing atherosclerosis in a patient in need of such treatment by administering to the patient a therapeutically effective amount of a compound of Formula 1, or a pharmaceutically acceptable salt thereof.

The present compounds can be used to treat or reduce hyperglycemia in a diabetic patient in need of such treatment by administering to the patient a therapeutically effective amount of a compound of Formula 1, or a pharmaceutically acceptable salt thereof.

The compounds may have utility in treating osteoporosis. The compounds of this invention may be used to treat osteoporosis or to reduce the risk of developing osteoporosis by slowing or stopping the loss of bone density in a patient who has osteoporosis or is at risk of developing osteoporosis. The compounds of this invention may also reverse the loss of bone mass in patients who have already begun to lose bone mass.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (such as torcetrapib), niacin, niacin receptor agonists, bile acid sequestrants, microsomal triglyceride transport inhibitors, and bile acid reuptake inhibitors. These combination treatments may also be effective for the treatment or control of one or more related conditions selected from the group consisting of hypercholesterolemia, atherosclerosis, hyperlipidemia, hypertriglyceridemia, dyslipidemia, high LDL, and low HDL.

Another aspect of the invention provides a method of treating inflammatory conditions, including inflammatory bowel disease, Crohn's disease, and ulcerative colitis by administering an effective amount of a compound of this invention to a patient in need of treatment. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.01 milligram to about 100 milligrams per kilogram of animal body weight, preferably given as a single daily dose or in divided doses two to six times a day, or in sustained release form. For most large mammals, including humans (e.g. a 70 kg adult), the total daily dosage is from about 0.1 milligrams to about 1000 milligrams, is likely to be from about 0.5 milligrams to about 350 milligrams, and is often from about 1 milligram to about 50 milligrams. For a particularly potent compound, the dosage for an adult human may be as low as 0.1 mg. Examples of daily dosages for a 70 kg adult human are 0.1 mg, 0.5 mg, 1 mg, 2 mg, 5 mg, 10 mg, 25 mg, 50 mg, 100 mg, 150 mg, 200 mg, 250 mg, 350 mg, and 500 mg per day. The daily dosage regimen may be adjusted within the above ranges or even outside of these ranges to provide the optimal therapeutic response.

Oral administration will usually be carried out using tablets. Examples of doses in tablets which may be administered once a day or more than once a day (e.g. 2×, 3×, or (rarely) 4 or more times per day, are 0.1 mg, 0.5 mg, 1 mg, 2 mg, 5 mg, 10 mg, 25 mg, 50 mg, 100 mg, 150 mg, 200 mg, 250 mg, 350 mg, and 500 mg. Other oral forms (e.g. capsules or suspensions) can also be administered in doses having similar sizes.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy. In general, compositions suitable for oral administration are preferred.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form, in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other PPAR gamma agonists and partial agonists, such as the glitazones (e.g. troglitazone, pioglitazone, englitazone, MCC-555, rosiglitazone, balaglitazone, netoglitazone, and the like), and PPAR gamma agonists and partial agonists that do not have a glitazone structure;

(b) biguanides such as metformin and phenformin;

(c) protein tyrosine phosphatase-1B (PTP-1B) inhibitors, (d) dipeptidyl peptidase IV (DP-IV) inhibitors, including sitagliptin, vildagliptin, and saxagliptin;

(e) insulin or insulin mimetics;

(f) insulin secretagogues, such as sulfonylureas (e.g. tolbutamide, glimepiride, and glipizide) and meglitinides (eg. repaglinide and nateglinide);

(g) α-glucosidase inhibitors (such as acarbose and miglitol);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) niacin receptor agonists, (v) PPARα agonists such as fenofibric acid derivatives (gemfibrozil, clofibrate, fenofibrate and bezafibrate), (vi) cholesterol absorption inhibitors, such as for example ezetimibe, (vii) acyl CoA:cholesterol acyltransferase (ACAT) inhibitors, such as avasimibe, (viii) CETP inhibitors, such as torcetrapib, JTT-705, and compounds disclosed in WO2005/100298, WO2006/014357, and WO2006/014413, and (ix) phenolic anti-oxidants, such as probucol;

(i) PPARα/γ dual agonists, such as KRP-297, muraglitazar, tesaglitazar, LY-818 and the like;

(j) PPARδ agonists such as those disclosed in WO97/28149;

(k) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and β3 adrenergic receptor agonists;

(l) ileal bile acid transporter inhibitors;

(m) agents intended for use in inflammatory conditions such as aspirin, non-steroidal anti-inflammatory drugs, glucocorticoids, azulfidine, and cyclo-oxygenase 2 selective inhibitors;

(n) glucagon receptor antagonists;

(o) GLP-1;

(p) GIP-1; and (q) GLP-1 analogs, such as exendins, including exenatide.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

Compounds of the present invention (i.e. compounds having Formula I) can be used to treat one or more diseases or conditions selected from hypercholesterolemia, atherosclerosis, low HDL levels, high LDL levels, hyperlipidemia, hypertriglyceridemia, and dyslipidemia by administering a therapeutically effective amount of a compound of claim 1 in combination with an HMG-CoA reductase inhibitor to a patient in need of such treatment. Statins are the preferred HMG-CoA reductase inhibitors for use in this combination therapy. Preferred statins include lovastatin, simvastatin, pravastatin, fluvastatin, atorvastatin, itavastatin, ZD-4522, rivastatin, and rosuvastatin. This combination treatment may be particularly desirable for treating or reducing the risk of developing atherosclerosis. Such a combination can optionally have a third pharmaceutically active ingredient, such as a CETP inhibitor (e.g. torcetrapib) or a cholesterol absorption inhibitor (e.g. ezetimibe).

Biological Assays

A) PPAR Binding Assays

For preparation of recombinant human PPARγ, PPARδ, and PPARα: Human PPARγ$_2$, human PPARδ and human PPARα were expressed as gst-fusion proteins in E. coli. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). E. coli containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C.

For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3$H$_2$]AD5075, (21 Ci/mmole), ± test compound as described in Berger et al (Novel peroxisome proliferator-activated receptor (PPARγ) and PPARδ ligands produce distinct biological effects. J. Biol. Chem. (1999), 274: 6718-6725. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$]L-783483, (17 Ci/mmole), ± test compound as described in Berger et al (Novel peroxisome proliferator-activated receptory (PPARγ) and PPARδ ligands produce distinct biological effects.1999 J Biol Chem 274: 6718-6725). (L-783483 is 3-chloro-4-(3-(7-propyl-3-trifluoromethyl-6-benz-[4,5]-isoxazoloxy)propylthio)phenylacetic acid, Ex. 20 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [$^3$H$_2$]L-797773, (34 Ci/mmole), ± test compound. (L-797733 is (3-(4-(3-phenyl-7-propyl-6-benz-[4,5]-isoxazoloxy)butyloxy))phenylacetic acid, Ex.62 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B) Gal-4 HPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5X)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at 12×10$^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% CO2. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5X)-tk-luc reporter vector and 0.0002 μg of pCMV-lacZ as an internal control for transactivation efficiency. Cells were incubated in the transfection mixture for 5 h at 37° C. in an atmosphere of 10% CO$_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

Agonism is determined by comparison of maximal transactivation activity with a full PPAR agonist, such as rosiglitazone. Generally, if the maximal stimulation of transactivation is less than 50% of the effect observed with a full agonist, then the compound is designated as a partial agonist. If the maximal stimulation of transactivation is greater than 50% of the effect observed with a full agonist, then the compound is designated as a full agonist. The compounds of this invention generally have EC50 values in the range of 1 nM to 3000 nM.

C) In Vivo Studies

Male db/db mice (10-11 week old C57B1/KFJ, Jackson Labs, Bar Harbor, Me.) are housed 5/cage and allowed ad lib. access to ground Purina rodent chow and water. The animals, and their food, are weighed every 2 days and are dosed daily by gavage with vehicle (0.5% carboxymethylcellulose)±test compound at the indicated dose. Drug suspensions are prepared daily. Plasma glucose, and triglyceride concentrations are determined from blood obtained by tail bleeds at 3-5 day intervals during the study period. Glucose and triglyceride, determinations are performed on a Boehringer Mannheim Hitachi 911 automatic analyzer (Boebringer Mannheim, Indianapolis, Ind.) using heparinized plasma diluted 1:6 (v/v) with normal saline. Lean animals are age-matched heterozygous mice maintained in the same manner.

EXAMPLES

The following Examples are provided to illustrate the invention and are not to be construed as limiting the invention in any manner. The scope of the invention is defined by the appended claims.

The process for making the compounds of the instant invention is generally depicted in Schemes 1-2 below.

Scheme 1

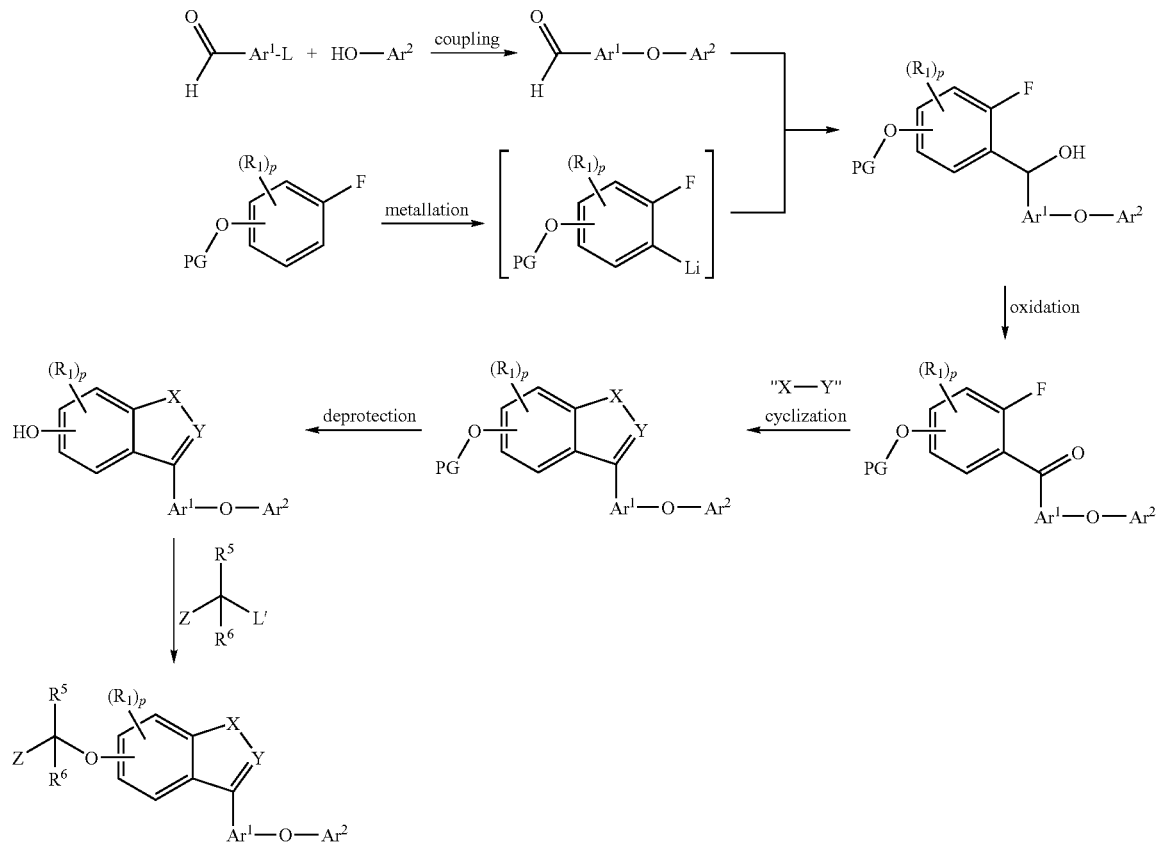

L, L' = leaving groups
PG = protecting group

Scheme 2

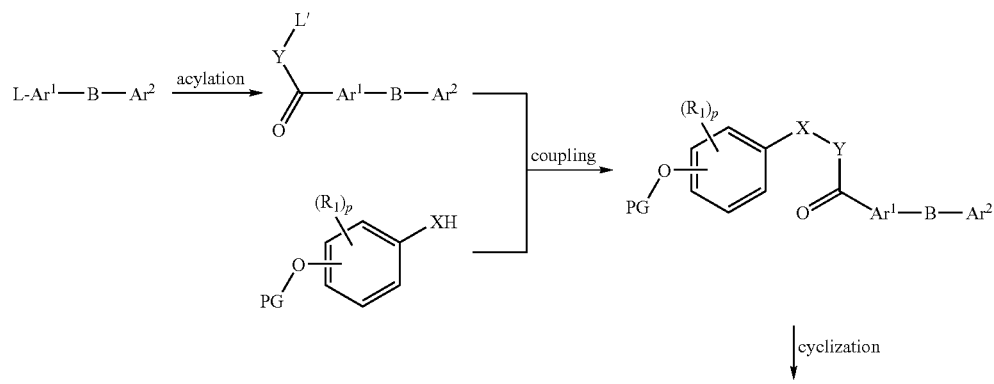

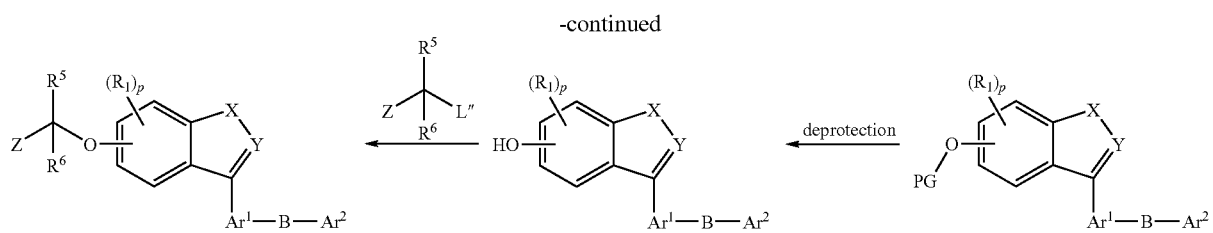

Example 1

(2S)-2-({3-[4-(4-chlorophenoxy)-2-propylphenyl]-1-benzofuran-5-yl}oxy)propanoic acid

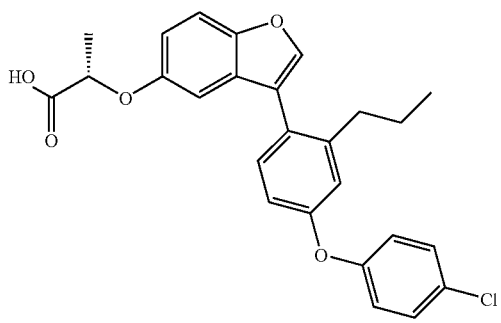

Step 1. Preparation of 4-chlorophenoxybenzaldehyde

A heterogeneous mixture of 4-chlorophenol (14.1 g, 0.11 mmol), 4-fluorobenzaldehyde 12.4 g, 0.1 mmol) and $CS_2CO_3$ (65.0 g, 0.20 mmol) in DMF (400 mL) was stirred at 90° C. for 6 h. The reaction mixture was poured into water (1.2 L) and extracted with ethyl acetate (2×200 mL). The organic phase was washed with water (2×100 mL), dried over magnesium sulfate and concentrated to give essentially pure 4-chlorophenoxybenzaldehyde, which was used directly in the next step.

Step 2. Preparation of 4-(4-chlorophenoxy)phenol

The crude aldehyde from step 1 (23.3 g, 0.10 mmol) was dissolved in dichloromethane (500 mL), and m-chloroperbenzoic acid (70%, 50.0 g, 0.20 mmol) and sodium bicarbonate (25.2 g, 0.30 mmol) were added. The resulting heterogeneous mixture was stirred and heated under reflux for 2 h and then quenched with an aqueous solution of sodium sulfite (0.5 M, 500 mL). After stirring at 25° C. for 30 min, the organic phase was separated and the aqueouse phase was extracted with dichloromethane (2×200 mL). The combined organic phases were washed with a saturated solution of sodium bicarbonate (2×200 mL), dried over magnesium sulfate and concentrated. The residue was chromatographed on silica gel, eluting with an 8:2 mixture of hexane and ethyl acetate to give the title phenol.

Step 3. Preparation of 3-[4-(4-chlorophenoxy)phenoxy]-1-propene

A mixture of the phenol from step 2 (16.5 g, 75 mmol), allyl bromide (10.8 g, 90 mmol) and cesium carbonate (48.7 g, 150 mmol) in DMF(300 mL) was stirred at 25° C. for 6 h. The mixture was poured into water (1.0 L) and extracted with ethyl acetate (2×200 mL). The combined organic phase was washed with water (3×100 mL), dried over magnesium sulfate and concentrated. The crude product was used directly in the next step.

Step 4. Preparation of 4-(4-chlorophenoxy)-2-(2-propenyl)phenol

The crude allyl ether from step 3 (20.0 g) was dissolved in 2,4,6-trichlorobenzene (60 mL), and the solution was heated at reflux for 4 h. After being cooled to room temperature, the solution was directly loaded onto a column of silica gel and eluted sequentially with hexane and an 8:2 mixture of hexane and ethyl acetate to give 4-(4-chlorophenoxy)-2-(2-propenyl)phenol.

Step 5. Preparation of 4-(4-chlorophenoxy)-2-propylphenol

A mixture of the product from step 4 (15.7 g, 60 mmol) and 10% Pd/C (3.1 g) in ethyl acetate (300 mL) was stirred under hydrogen (1 atm). After the reaction was completed (ca. 30 min), the mixture was filtered through celite and the filtrate was concentrated to give 15.7 g of the title compound as an oil which solidified upon standing.

Step 6. Preparation of 4-(4-chlorophenoxy)-2-propylphenyl trifluoromethanesulfonate To a solution of the phenol from Step 5 (2.6 g, 10 mmol) and ethyldisopropylamine (3.5 mL, 20 mmol) in dichloromethane (50 mL) cooled at −75° C. was added triflic anhydride (2.0 mL, 12 mmol). The resulting solution was warmed gradually to 0° C. and quenched with water. The organic layer was washed with water and dried over magnesium sulfate. Removal of the solvent gave a residue which was redissolved in diethyl ether and filtered through a short pad of silica gel to give 4-(4-chlorophenoxy)-2-propylphenyl trifluoromethanesulfonate.

Step 7. Preparation of 1-[4-(4-chlorophenoxy)-2-propylphenyl]ethanone

A mixture of the product from Step 6 (2.0 g, 5.0 mmol), n-butyl vinyl ether (25 mmol), triethylamine (0.83 mL, 6.0 mmol), palladium acetate (0.125 mmol) and 1,3-bis(diphenylphosphino)propane (51.5 mg, 0.125 mmol) in DMF (25 mL) was heated at 80° C. under nitrogen for 4 h. The reaction mixture was poured into 1 N hydrochloric acid and extracted with ethyl acetate. The organic phase was washed with water and concentrated. The residue was purified by chromatography on silica gel to afford the title product.

Step 8. 2-bromo-1-[4-(4-chlorophenoxy)-2-propylphenyl]ethanone

To a solution of the product from Step 7 (1.2 g, 4.2 mmol) in dioxane (20 mL) at room temperature was added dropwise bromine (0.25 mL, 5.0 mmol). After 2 h at room temperature, the reaction mixture was diluted with ethyl acetate, washed with an aqueous solution of sodium thiosulfate and dried over magnesium sulfate. Removal of the solvent gave a residue which was purified by chromatography on silica gel to give the title product.

Step 9. 1-[4-(4-chlorophenoxy)-2-propylphenyl]-2-(4-methoxyphenoxy)ethanone

A mixture of the product from Step 8 (0.50 g, 1.4 mmol), p-methoxyphenol (2.8 mmol) and cesium carbonate (0.91 g, 2.8 mmol) in DMF (10 mL) was stirred at room temperature for 1 h. The reaction mixture was diluted with ethyl acetate and washed with water. The solvent was evaporated and the residue was purified by chromatography on silica gel to give the title product as an oil.

Step 10. 3-[4-(4-chlorophenoxy)-2-propylphenyl]-5-methoxy-1-benzofuran

A mixture of the product from Step 9 (0.46 g, 1.1 mmol) and Amberlyst-15 (0.50 g) in xylene (10 mL) was heated at 140° C. for 2 h. The reaction mixture was filtered and the filtrate was concentrated. The residue was purified by chromatography on silica gel to give the title product.

Step 11. 3-[4-(4-chlorophenoxy)-2-propylphenyl]-1-benzofuran-5-ol

To a solution of the product from Step 10 (0.34 g, 0.86 mmol) in dichloromethane (5.0 mL) cooled with an ice bath was added boron tribromide (1.0 M in dichloromethane, 1.7 mL, 1.7 mmol). The reaction mixture was gradually warmed to room temperature over 1 h, diluted with ethyl acetate and poured into a saturated solution of sodium bicarbonate. The organic layer was washed with brine, dried and filtered through a short path of silica gel to give the title product.

Step 12. (2S)-2-({3-[4-(4-chlorophenoxy)-2-propylphenyl]-1-benzofuran-5-yl}oxy)propanoic acid The title compound was prepared according to the following general procedure using the phenol from Step 11 and methyl (R)-lactate as the substrates.

General procedure. To a solution of an appropriate phenol (5 mmol), methyl lactate (7.5 mmol) and triphenylphosphine (7.5 mmol) in THF (30 mL) cooled in ice bath was added dropwise diethyl azodicarboxylate (7.5 mmol). The reaction mixture was warmed to room temperature and stirred for 1 h. Acetic acid (0.1 mL) was added and the reaction mixture was concentrated. The residue was triturated with 1:1 diethyl ether:hexane and the precipitate was filtered off. The filtrate was concentrated to give a residue which was purified by chromatography on silica gel to give the coupling product. The coupling product was dissolved in methanol (50 mL) and treated with 2 N NaOH (7.5 mL) at room temperature for 1 h. The reaction mixture was acidified with 2 N hydrochloric acid (or acetic acid) to pH 3 and concentrated. The residue was purified by preparative HPLC on a RP C-18 column using 10-100% acetonitrile in water gradient solvent system modified with 0.1% trifluoroacetic acid to give the final product.

$^1$H NMR (600 MHz, CD$_3$OD) δ 7.65 (s, 1H), 7.39 (d, J=9.0 Hz, 1H), 7.35 (d, J=9.0 Hz, 2 H), 7.28 (d, J=8.4 Hz, 1H), 7.02 (d, J=8.4 Hz, 2H), 6.97 (d, J=3.0 Hz, 1H), 6.96 (dd, J=9.0, 2.4 Hz, 1H), 6.88 (dd, J=8.4 Hz, 2.4 Hz, 1H), 6.80 (d, J=2.4 Hz, 1H), 4.52 (q, d=7.2 Hz, 1H), 2.56 (t, J=7.8 Hz, 2H), 1.51 (d, J=7.2 Hz, 3H), 1.45 (m, 2H), 0.76 (t, J=7.2 Hz, 3H).

MS (ESI, m/z): 450.9 (M+1).

Example 2

(2S)-2-({6-chloro-3-[4-(4-chlorophenoxy)-2-propylphenyl]-1-benzofuran-5-yl}oxy)propanoic acid

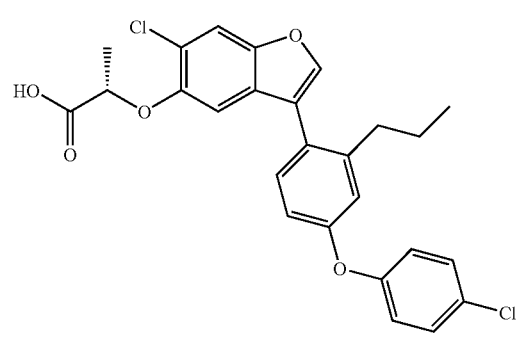

The title compound was prepared following the same procedure as described for Example 1 except that, in step 9 of Example 1, 3-chloro-4-methoxyphenol was used instead of 4-methoxyphenol.

$^1$H NMR (500 MHz, CD$_3$OD) δ 7.74 (s, 1H), 7.66 (s, 1H), 7.38 (d, J=9.0 Hz, 2H), 7.28 (d, J=8.5 Hz, 1H), 7.04 (d, J=9.0 Hz, 2H), 7.00 (d, J=8.5 Hz, 1H), 6.96 (dd, J=8.5, 2.5 Hz, 1H), 6.90 (s, 1H), 4.60 (m, 1H), 2.55 (t, J=7.5 Hz, 2H), 1.62 (d, J=7 Hz, 3H), 1.45 (m, 2H), 0.77 (t, J=8.5 Hz, 3H).

Example 3

(2S)-2-({3-[4-(4-chlorophenoxy)-2-propylphenyl]-1,2-benzisoxazol-5-yl}oxy)propanoic acid

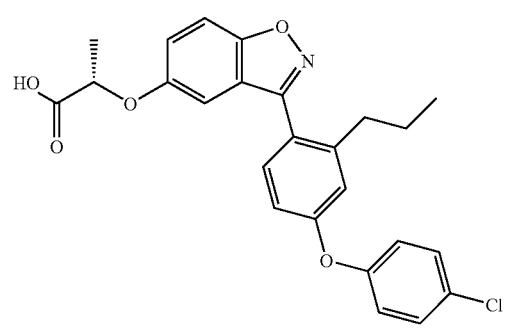

Step 1. 4-(4-chlorophenoxy)-2-propylbenzaldehyde

A mixture of the triflate from Step 6 of Example 1 (3.98 g, 10 mmol), trioctylsilane (6.7 mL, 15 mmol), triethyl amine (7.0 mL, 25 mmol), palladium acetate (0.22 g, 0.5 mmol) and diphenylphosphine (0.21 g, 0.5 mmol) in DMF (60 mL) was stirred at 80° C. under an atmosphere of carbon monoxide (50 psi) for 5 h. The reaction was then diluted with ethyl acetate and water. The organic layer was washed with water and concentrated. The residue was purified by chromatography on silica gel to give the title product.

Step 2 (2-fluoro-5-methoxphenyl)[4-(4-chlorophenoxy)-2-propylphenyl]methanol

To a solution of 2,2,6,6-tetramethylpiperidine (2.75 g, 10 mmol) in THF (50 mL) cooled at −75° C. was added a solution of n-butyllithium in hexane (1.6 M, 6.3 mL, 10 mmol). After 15 min, 4-fluoroanisole (1.3 g, 10 mmol) was added and the solution was warmed gradually to −40° C. over a 2 h period. The solution was recooled to −75° C. and a solution of the aldehyde from Step 1 (1.4 g, 5.1 mmol) in THF (3 mL) was added quickly. The reaction mixture was stirred for 15 min., poured into a saturated aqueous solution of ammonium chloride and extracted with ethyl acetate. After removal of the solvent, the residue was purified by chromatography on silica gel to give the title product.

Step 3. [4-(4-chlorophenoxy)-2-propylphenyl](2-fluoro-5-methoxyphenyl)methanone

A mixture of the product from Step 2 (1.6 g, 4.0 mmol), N-methylmorpholine-N-oxide (0.70 g, 6.0 mmol), tetrapropylammonium perruthenate (70 mg, 0.2 mmol) and 4A molecular sieves (1.6 g) in dichloromethane (20 mL) was stirred at 25° C. for 1 h. The reaction mixture was diluted with diethyl ether (60 mL) and filtered through a short path of silica gel. Removal of the solvent gave the title product.

Step 4. (Z)-[4-(4-chlorophenoxy)-2-propylphenyl](2-fluoro-5-methoxyphenyl)methanone oxime A mixture of the product from Step 3 (1.6 g, 4.0 mmol), hydroxylamine hydrochloride (2.8 g, 40 mmol) and sodium acetate (3.3 g, 40 mmol) in ethanol (40 mL) was stirred in a sealed tube at 60° C. for 48 h. The precipitate was filtered off and the filtrate was concentrated. The residue was purified by chromatography on silica gel to give the oxime product.

Step 5. 3-[4-(4-chlorophenoxy)-2-propylphenyl]-5-methoxy-1,2-benzisoxazole

A mixture of the oxime from Step 4 (1.4 g, 3.3 mmol) and cesium carbonate (2.1 g, 6.7 mmol) in DMF (20 mL) was stirred at 80° C. for 18 h. The reaction was diluted with ethyl acetate and washed with water. The crude product was purified by chromatography on silica gel to give the title product.

Step 6. 3-[4-(4-chlorophenoxy)-2-propylphenyl]-1,2-benzisoxazol-5-ol

To a solution of the product from Step 5 (1.0 g, 2.5 mmol) in dichloromethane (15 mL) cooled at 0° C. was added a solution of boron tribromide in heptane (1.0 M, 5.0 mL, 5.0 mmol). The reaction was stirred at 25° C. for 30 min and then poured into aqueous sodium bicarbonate. The aqueous layer was extracted with ethyl acetate. The combined organic phase was washed with brine, dried over magnesium sulfate and concentrated. The residue was purified by chromatography on silica gel to give the title product.
$^1$H NMR (500 MHz, CDCl$_3$) δ 7.54 (d, J==8.5 Hz, 1H), 7.45 (d, J=8.5 Hz, 1H), 7.39 (d, J=9.0 Hz, 1H), 7.19 (dd, J=2.5, 8.5 Hz, 1H), 7.04-7.09 (m, 3H), 6.94-6.98 (m, 2H), 2.70 (t, J=7.5 Hz, 2H), 1.56 (m, 2H), 0.83 (t, J=7.5 Hz, 3H).
MS (ESI, m/z): 380.1(M++1).

Step 7. (2S)-2-({3-[4-(4-chlorophenoxy)-2-propylphenyl]-1,2-benzisoxazol-5-yl}oxy)propanoic acid The phenol from Step 6 (0.38 g, 1.0 mmol) and methyl (R)-lactate (0.16 g, 1.5 mmol) was reacted according the general procedure described in Step 11 of Example 1 to give the title compound as a white solid.
$^1$H NMR (500 MHz, CDCl$_3$) δ 7.60 (d, J=8.5 Hz, 1H), 7.38-7.42 (m, 3H), 7.30 (m, 1H), 7.04-7.10 (m, 3H), 6.94-7.0. (m, 2H), 4.83 (q, J=7.5 Hz, 1H), 2.70 (t, J=7.5 Hz, 2H), 1.70 (d, J=7.5 Hz, 3H), 1.53 (m, 2H), 0.83 (t, J=7.5 Hz, 3H).
MS (ESI, m/z): 452.1 (M+1).

Example 4

(2S)-2-({4-chloro-3-[4-(4-chlorophenoxy)-2-propylphenyl]-1,2-benzisoxazol-5-yl}oxy)propanoic acid

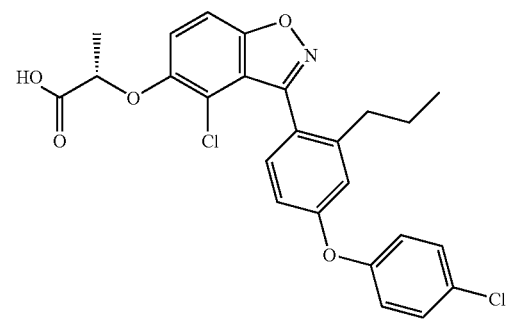

Step 1. 4-chloro-3-[4-(4-chlorophenoxy)-2-propylphenyl]-1,2-benzisoxazol-5-ol

To a solution of the phenol product obtained from step 6 of Example 3 (0.38 g, 1.0 mmol) and diisobutylamine (18 μL, 0.10 mmol) in toluene (5 mL) was added dropwise sulfuryl chloride (80 μL, 1.0 mmol) over 10 min. The resulting solution was stirred at 25° C. for 1 h and then quenched with a saturated solution of aqueous sodium bicarbonate. The organic layer was extracted with ethyl acetate and the combined organic layer was washed with 2 N solution of sodium sulfite. After removal of the solvent, the crude product was purified by chromatography on silica gel eluting with 7:3 hexane:ethyl acetate to give the title product as a solid.
MS (ESI, m/z): 415.2 (M$^+$+1).

Step 2. (2S)-2-({4-chloro-3-[4-(4-chlorophenoxy)-2-propylphenyl]-1,2-benzisoxazol-5-yl}oxy)propanoic acid The phenol product from Step 1 (0.38 g, 0.9 mmol) and methyl (R)-lactate (0.16 g, 1.5 mmol) was reacted according the general procedure described in Step 11 of Example 1 to give the title compound as a white solid.
$^1$H NMR (500 MHz, CDCl$_3$) δ 7.63 (d, J=8.5 Hz, 1H), 7.46 (d, J=8.5, 1H), 7.43 (d, J=9.0 Hz, 2H), 7.38 (d, J=8.5 Hz, 1H), 7.10 (d, J=9.0 Hz, 2H), 7.03 (d, J=2.5 Hz, 1H), 6.96 (dd, J=2.5, 8.5 Hz, 1H), 4.91 (q, J=7.5 Hz, 1H), 2.51 (m, 2H), 1.65 (d, J=7.5 Hz, 3H), 1.47 (m, 2H), 0.78 (t, J=7.5 Hz, 3H).
MS (ESI, m/z): 486.1 (M$^+$+1).

Example 5

(2R)-2-({6-chloro-3-[4-(4-chlorophenoxy)-2-propylphenyl]-1,2-benzisoxazol-5-yl}oxy)propanoic acid

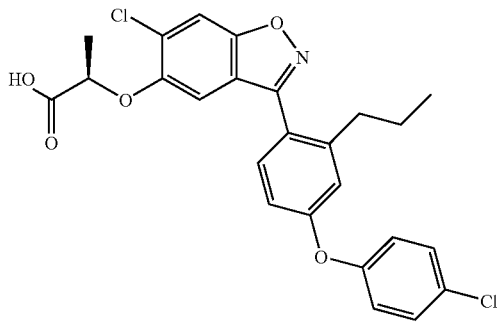

Step 1. Preparation of 4-fluoro-2-chloro-3-(trimethylsilyl)anisole

To a solution of 2-chloro-4-fluoroanisole (16.5 g, 100 mmol) in THF (500 mL) cooled at −75° C. was added dropwise a solution of t-BuLi in pentane (1.7 M, 61.8 mL, 105 mmol). The reaction was kept at −75° C. for 15 min, quenched at −75° C. with trimethylchlorosilane (19.0 mL, 150 mmol) and finally poured into a saturated solution of sodium bicarbonate. The organic layer was washed with brine, dried over magnesium sulfate and concentrated. The residue was purified by chromatography on silica gel eluting with 20:1 hexane:diethyl ether to give the title product.

Step 2. Preparation of [4-chloro-2-fluoro-5-methoxy-3-(trimethylsilyl)phenyl][4-(4-chlorophenoxy)-2-propylphenyl]methanol To a solution of 2,2,6,6-tetramethylpiperidine (2.75 g, 10 mmol) in THF (50 mL) cooled at −75° C. was added a solution of n-butyllithium in hexane (1.6 M, 6.3 mL, 10 mmol). After 15 min, 4-fluoro-2-chloro-3-(trimethylsilyl)anisole (2.3 g, 10 mmol) was added and the solution was warmed gradually to −40° C. over a 2 h period. The solution was recooled to −75° C. and a solution of the aldehyde from Step 1 of Example 3 (1.4 g, 5.0 mmol) in THF (3 mL) was added quickly. The reaction mixture was stirred for 15 min., poured into a saturated aqueous solution of ammonium chloride and extracted with ethyl acetate. After removal of the solvent, the residue was purified by chromatography on silica gel to give the title product.

Step 3. Preparation of [4-(4-chlorophenoxy)-2-propylphenyl][4-chloro-2-fluoro-5-methoxyphenyl]methanone A mixture of the product from Step 2 (1.9 g, 3.7 mmol), N-methylmorpholine-N-oxide (0.70 g, 6.0 mmol), tetrapropylammonium perruthenate (70 mg, 0.2 mmol) and 4 Å molecular sieves (2.0 g) in dichloromethane (20 mL) was stirred at 25° C. for 1 h. The reaction mixture was diluted with diethyl ether (60 mL) and filtered through a short path of silica gel. Removal of the solvent gave the crude product. The crude product was dissolved in THF (20 mL) and treated with tetrabutylammonium fluoride (1M in THF, 5.6 mL, 5.6 mmol) for 10 min. The reaction mixture was diluted with ethyl acetate, washed with brine, dried and concentrated. The residue was purified by chromatography on silica gel to give the title product.

Step 4. Preparation of (Z)-[4-(4-chlorophenoxy)-2-propylphenyl](4-chloro-2-fluoro-5-methoxyphenyl)methanone oxime A mixture of the product from Step 3 (1.4 g, 3.2 mmol), hydroxylamine hydrochloride (2.2 g, 32 mmol) and sodium acetate (2.6 g, 32 mmol) in ethanol (30 mL) was stirred in a sealed tube at 60° C. for 72 h. The precipitate was filtered off and the filtrate was concentrated. The residue was purified by chromatography on silica gel to give the oxime product.

Step 5. Preparation of 6-chloro-3-[4-(4-chlorophenoxy)-2-propylphenyl]-5-methoxy-1,2-benzisoxazole A mixture of the oxime from Step 4 (1.2 g, 2.7 mmol) and cesium carbonate (1.7 g, 5.4 mmol) in DMF (20 mL) was stirred at 80° C. for 18 h. The reaction was diluted with ethyl acetate and washed with water. The crude product was purified by chromatography on silica gel to give the title product.

Step 6. Preparation of 6-chloro-3-[4-(4-chlorophenoxy)-2-propylphenyl]-1,2-benzisoxazol-5-ol To a solution of the product from Step 5 (0.82 g, 1.9 mmol) in dichloromethane (15 mL) cooled at 0° C. was added a solution of boron tribromide in heptane (1.0 M, 3.8 mL, 3.8 mmol). The reaction was stirred at 25° C. for 30 min and then poured into aqueous sodium bicarbonate. The aqueous layer was extracted with ethyl acetate. The combine organic phase was washed with brine, dried over magnesium sulfate and concentrated. The residue was purified by chromatography on silica gel to give the title product.

Step 7. Preparation of (2R)-2-({6-chloro-3-[4-(4-chlorophenoxy)-2-propylphenyl]-1,2-benzisoxazol-5-yl}oxy)propanoic acid The phenol from Step 6 (0.38 g, 1.0 mmol) and methyl (S)-lactate (0.16 g, 1.5 mmol) was reacted according the general procedure described in Step 11 of Example 1 to give the title compound as a white solid.

$^1$H NMR (500 MHz, CDCl$_3$) δ 7.82 (s, 1H), 7.48 (d, J=8.5, 1H), 7.42 (d, J=9.0 Hz, 2H), 7.10 (d, J=9.0 Hz, 2H), 7.06 (d, J=2.5 Hz, 1H), 7.02 (s, 1H), 6.98 (dd, J=2.5, 8.5 Hz, 1H), 4.49 (q, J=7.5 Hz, 1H), 2.68 (t, J=2.5 Hz, 2H), 1.63 (d, J=7.5 Hz, 3H), 1.50 (m, 2H), 0.81 (t, J=7.5 Hz, 3H).

MS (ESI, m/z): 486.1 (M$^+$+1).

Example 6

(2S)-2-({6-chloro-3-[4-(4-chlorophenoxy)-2-propylphenyl]-1,2-benzisoxazol-5-yl}oxy)propanoic acid

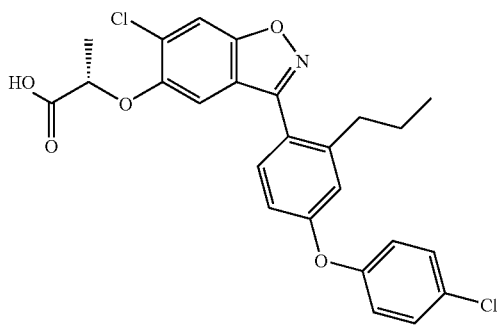

The phenol from Step 6 of Example 5 (0.42 g, 1.0 mmol) and methyl (R)-lactate (0.16 g, 1.5 mmol) was reacted according the general procedure described in Step 11 of Example 1 to give the title compound as a white solid.

$^1$H NMR (500 MHz, CDCl$_3$) δ 7.82 (s, 1H), 7.48 (d, J=8.5, 1H), 7.42 (d, J=9.0 Hz, 2H), 7.10 (d, J=9.0 Hz, 2H), 7.06 (d, J=2.5 Hz, 1H), 7.02 (s, 1H), 6.98 (dd, J=2.5, 8.5 Hz, 1H), 4.49 (q, J=7.5 Hz, 1H), 2.68 (t, J=2.5 Hz, 2H), 1.63 (d, J=7.5 Hz, 3H), 1.50 (m, 2H), 0.81 (t, J=7.5 Hz, 3H).

MS (ESI, m/z): 486.1 (M$^+$+1).

Compounds of Examples 7 through 11 were prepared according to procedures similar to those described for Examples 5 and 6.

Example 7

(2S)-2-({6-chloro-3-[4-(4-methylphenoxy)-2-propylphenyl]-1,2-benzisoxazol-5-yl}oxy)propanoic acid

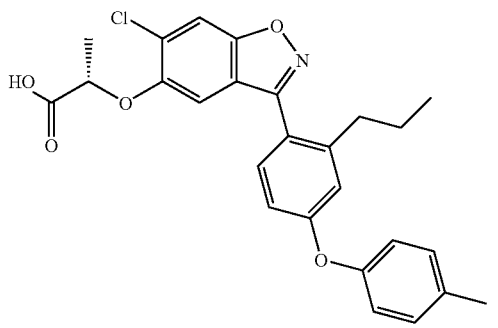

$^1$H NMR (500 MHz, CD$_3$OD) δ 7.82 (s, 1H), 7.44 (d, J=8.5 Hz, 1H), 7.25 (d, J=8.0 Hz, 2H), 7.02 (s, 1H), 7.00 (d, J=8.0 Hz, 2H), 6.99 (d, J=2.5 Hz, 1H), 6.93 (dd, J=8.5, 2.5 Hz, 1H), 4.46 (q, J=7.0 Hz, 1H), 2.66 (t, J=7.5 Hz, 2H), 2.37 (s, 3H), 1.63 (d, J=7.0 Hz, 3H), 1.48 (m, 2H), 0.81 (t, J=7.5 Hz, 3H).

MS (ESI, m/z): 466.2 (M+1).

Example 8

(2S)-2-({6-chloro-3-[4-(4-ethylphenoxy)-2-propylphenyl]-1,2-benzisoxazol-5-yl}oxy)propanoic acid

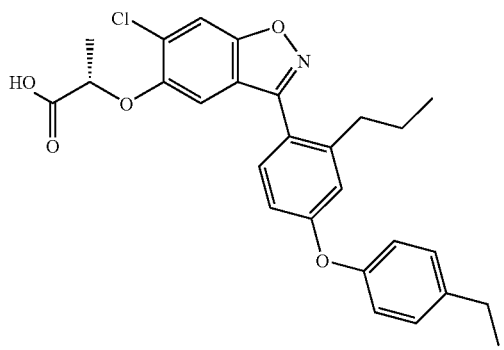

$^1$H NMR (500 MHz, CDCl$_3$) δ 7.79 (s, 1H), 7.37 (d, J=8.0 Hz, 1H), 7.27 (d, J=8.5 Hz, 2H), 7.09 (s, 1H), 7.08 (d, J=2.5 Hz, 1H), 7.07 (d, J=8.5 Hz, 2H), 6.96 (dd, J=8.0 Hz, 2.0 Hz, 1H), 4.84 (q, J=7.0 Hz, 1H), 2.72 (q, J=7.5 Hz, 2H), 2.67 (t, J=7.5 Hz, 3H). 7.0 Hz, 3H), 1.55 (m, 2H), 1.31 (t, J=7.5 Hz, 3H), 0.85 (t, J=7.5 Hz, 3H).

MS (ESI, m/z): 480.3 (M+1).

Example 9

(2S)-2-[(6-chloro-3-{2-propyl-4-[4-(trifluoromethoxy)phenoxy]phenyl}-1,2-benzisoxazol-5-yl)oxy]propanoic acid

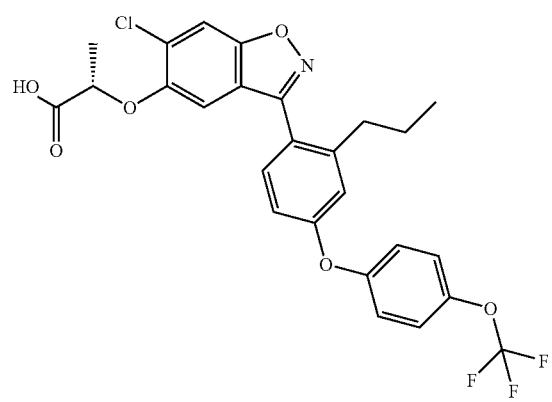

$^1$H NMR (500 MHz, CDCl$_3$) δ 7.76 (s, 1H), 7.37 (d, J=8.0 Hz, 1H), 7.27 (d, J=8.5 Hz, 1H), 7.12 (d, J=8.5 Hz, 2H), 7.07 (d, J=2.5 Hz, 1H), 7.05 (s, 1H), 6.95 (dd, J=8.0, 2.5 Hz, 1H), 4.82 (q, J=7.0 Hz, 1H), 2.66 (m, 2H), 1.73 (d, J=7.0 Hz, 3H), 1.52 (m, 2H), 0.82 (t, J=7.5 Hz, 3H).

MS (ESI, m/z): 536.2 (M+1).

Example 10

(2S)-2-({6-chloro-3-[4-(3-chlorophenoxy)-2-propylphenyl]-1,2-benzisoxazol-5-yl}oxy)propanoic acid

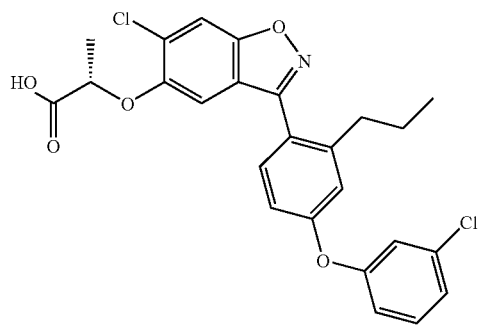

$^1$H NMR (500 MHz, CDCl$_3$) δ 7.80 (s, 1H), 7.42 (d, J=8.5 Hz, 1H), 7.36 (t, J=8.0 Hz, 1H), 7.19 (dt, J=8.0 Hz, 1 Hz, 1H), 7.14 (t, J=2.0 Hz, 1H), 7.10 (d, J=2.5 Hz, 1H), 7.03 (ddd, J=8.5, 3.0, 1.0 Hz, 1H), 7.01 (dd, J=8.5 Hz, 2.5 Hz, 1H), 4.85 (q, J=7.0 Hz, 2H), 2.68 (td, J=7.5, 2.0 Hz, 2H), 1.77 (d, J=7.0 Hz, 3H), 1.56 (m, 2H), 0.86 (t, J=7.5 Hz, 3H).

MS (ESI, m/z): 486.1 (M+1).

Example 11

(2S)-2-({6-chloro-3-[4-(3-chloro-4-methylphenoxy)-2-propylphenyl]-1,2-benzisoxazol-5-yl}oxy)propanoic acid

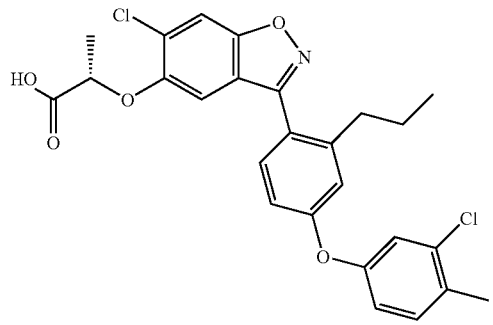

$^1$H NMR (500 MHz, CDCl$_3$) δ 7.78 (s, 1H), 7.37 (dd, J=8.5, 2.5 Hz, 2H), 7.07 (s, 1H), 7.05 (d, J=2.5 Hz, 1H), 7.01 (d, J=2.5 Hz, 1H), 6.95 (dd, J=8.5, 2.5 Hz, 1H), 6.91 (dd, J=8.5, 2.5 Hz, 1H), 4.83 (q, J=4.83 Hz, 1H), 2.66 (t, J=7.0 Hz, 2H), 2.41 (s, 3H), 1.75 (d, J=7.0 Hz, 3H), 1.53 (m, 2H), 0.84 (t, J=7.5 Hz, 3H).

MS (ESI, m/z): 500.2 (M+1).

Example 12

({6-chloro-3-[6-(4-chlorophenoxy)-2-propylpyridin-3-yl]-1,2-benzisoxazol-5-yl}oxy)acetic acid

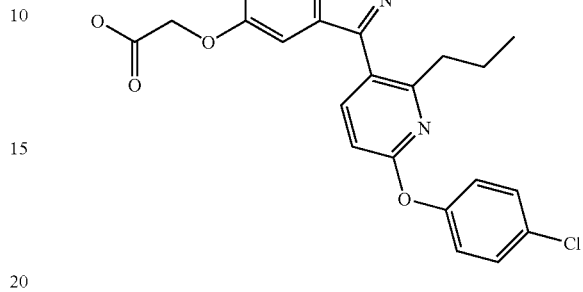

Step 1. Preparation of methyl 2,6-dichloronicotinate

To a solution of 2,6-dichloronicotinic acid (52 g, 0.27 mol) in benzene:MeOH (7:1, 1.0 L) was added dropwise a solution of (trimethylsilyl)diazomethane (1 M in heptane) until gas evolution ceased and the yellow color persisted (ca. 320 mL, 1.2 equiv.). The volatiles were removed and the residue was purified by chromatography on silica gel eluting with 7:1 hexane:ethyl acetate to give the product as a white solid.

Step 2. Preparation of methyl 2-chloro-6-(4-chlorophenoxy)nicotinate

A mixture of the product from Step 1 (54 g, 0.26 mol), p-chlorophenol (31.7 g, 0.25 mol) and cesium carbonate (101.4 g, 0.31 mol) in anhydrous DMF (1.0 L) was stirred at 25° C. for about 2 h or until less than 5% of the starting material remained. The reaction mixture was then poured into water (2.5 L) and extracted with ethyl acetate (2×800 mL). The organic layer was washed with water (2×300 mL) and dried over magnesium sulfate. The crude product was purified by chromatography on silica gel eluting with 7:1 hexane:ethyl acetate to afford the title product.

Step 3. Preparation of methyl 6-(4-chlorophenoxy)-2-propylnicotinate

To a solution of product from Step 2 (73.0 g, 0.245 mol) and Fe(acac)$_3$ (4.3 g, 12.2 mmol) in THF (1.2 L) cooled at −30° C. was added a solution of n-propylmagnesium chloride (2 M in Et$_2$O, 245 mL, 0.49 mol) over 45 min, while maintaining the reaction temperature below −30° C. The dark-colored reaction mixture was stirred for an additional 15 min and poured into a saturated aqueous solution of NH$_4$Cl (1.5 L). The organic layer was separated and washed with brine (1×250 mL). After removal of the solvent, the crude product was purified by chromatography on silica gel eluting with 100% hexane and then with 15:1 hexane:ethyl acetate to furnish the title product as an oil.

Step 4. Preparation of [6-(4-chlorophenoxy)-2-propylpyridin-3-yl]methanol

To a solution of the product from Step 3 (48 g, 157 mmol) in toluene (500 mL) cooled at −75° C. was added a solution of diisobutylaluminum hydride (1.0 M in toluene, 314 mL, 314 mmol) over a 45 min period. After additional 30 min at −75° C., the reaction mixture was poured into a ice-cold solution of 1 N hydrochloric acid (1.5 L) and the mixture was stirred at room temperature for 30 min. The product was extracted with ethyl acetate (2×500 mL) and organic extracts were washed with a saturated solution of sodium bicarbonate and brine. After removal of the solvent, the crude product was purified by chromatography on silica gel eluting with 7:1 hexane:ethyl acetate to give the title product as an oil.

Step 5. Preparation 6-(4-chlorophenoxy)-2-propylnicotinaldehyde

A mixture of the product from Step 4 (30.5 g, 110 mmol), N-methylmorpholine-N-oxide (19.3 g, 165 mmol), tetrapropylammonium perruthenate (1.9 g, 5.5 mmol) and 4 Å molecular sieves (55 g) in dichloromethane (500 mL) was cooled with a water bath at 20° C. and stirred for 1 h. The reaction mixture was diluted with diethyl ether (1.5 L), stirred for 15 min and filtered through a short path of silica gel. Removal of the solvent gave the title product as a light yellow oil.

$^1$H NMR (500 MHz, CDCl$_3$) δ 10.30 (s, 1H), 8.18 (d, J=8.5 Hz, 1H), 7.42 (d, J=9.0 Hz, 2H), 7.16 (d, J=9.0 Hz, 2H), 6.84 (d, J=8.5 Hz, 1H), 3.06 (t, J=7.5 Hz, 2H), 1.72 (m, 2H), 0.97 (t, J=7.5 Hz, 3H).

MS (ESI, m/z): 276.1 (M$^+$+1).

Step 6. Preparation of [4-chloro-2-fluoro-5-methoxy-3-(trimethylsilyl)phenyl][4-(4-chlorophenoxyl-2-propylpyridin-3-yl]methanol To a solution of 2,2,6,6-tetramethylpiperidine (27.5 g, 100 mmol) in THF (500 mL) cooled at −75° C. was added a solution of n-butyllithium in hexane (1.6 M, 63 mL, 100 mmol). After 15 min, 4-fluoro-2-chloro-3-(trimethylsilyl) anisole (23 g, 100 mmol) was added and the solution was warmed gradually to −50° C. over a 2 h period. The solution was recooled to −75° C. and a solution of the aldehyde from Step 5 (21 g, 75 mmol) in THF (30 mL) was added quickly. The reaction mixture was stirred for 15 min., poured into a saturated aqueous solution of ammonium chloride and extracted with ethyl acetate. After removal of the solvent, the residue was purified by chromatography on silica gel to give the title product.

Step 7. Preparation of [4-chloro-2-fluoro-5-methoxyphenyl][4-(4-chlorophenoxy)-2-propylpyridin-3-yl] methanone A mixture of the product from Step 6 (19.0 g, 37 mmol), N-methylmorpholine-N-oxide (7.0 g, 60 mmol), tetrapropylammonium perruthenate (0.70 g, 2.0 mmol) and 4 Å molecular sieves (20 g) in dichloromethane (200 mL) was stirred at 25° C. for 1 h. The reaction mixture was diluted with diethyl ether (600 mL) and filtered through a short path of silica gel. Removal of the solvent gave the crude product. The crude product was dissolved in wet THF (200 mL, 2% water) and treated with tetrabutylammonium fluoride (1M in THF, 56 mL, 56 mmol) for 10 min. The reaction mixture was diluted with ethyl acetate, washed with brine, dried and concentrated. The residue was purified by chromatography on silica gel to give the title product.

Step 8. Preparation of [4-chloro-2-fluoro-5-methoxy-3-(trimethylsilyl)phenyl][4-(4-chlorophenoxy)-2-propylpyridin-3-yl]methanone oxime A mixture of the product from Step 7 (14 g, 32 mmol), hydroxylamine hydrochloride (22 g, 320 mmol) and sodium acetate (26 g, 320 mmol) in ethanol (300 mL) was stirred in a sealed tube at 60° C. for 72 h. The solid was filtered off and the filtrate was concentrated. The residue was purified by chromatography on silica gel to give the title oxime.

Step 9. Preparation of 6-chloro-3-[4-(4-chlorophenoxy)-2-propylpyridin-3-yl]-5-methoxy-1,2-benzisoxazole A mixture of the oxime from Step 8 (12.0 g, 27 mmol) and cesium carbonate (17 g, 54 mmol) in DMF (200 mL) was stirred at 80° C. for 18 h. The reaction was diluted with ethyl acetate and washed with water. The crude product was purified by chromatography on silica gel to give the title product.

Step 10. Preparation of 6-chloro-3-[4-(4-chlorophenoxy)-2-propylpyridin-3-yl]1,2-benzisoxazol-5-ol The product from Step 9 (4.3 g, 10 mmol) and boron tribromide dimethyl sulfide complex (12.4 g, 40 mmol) were mixed in dichloroethane (100 mL). The resulting solution was heated at 85° C. for 18 h. The mixture was diluted with ethyl acetate (200 mL), washed with a saturated solution of sodium bicarbonate, dried over magnesium sulfate and concentrated. The residue was purified by chromatography on silica gel to give the title product as a white solid.

$^1$H NMR (500 MHz, CDCl$_3$) δ 7.79 (d, J=8.5 Hz, 1H), 7.75 (s, 1H), 7.43 (d, J=9.0 Hz, 2H), 7.20 (d, J=9.0 Hz, 2H), 7.15 (s, 1H), 6.88 (d, J=8.5 Hz, 2H), 5.80 (br. s, 1H), 2.75 (t, J=7.5 Hz, 2H), 1.67 (m, 2H), 0.85 (t, J=7.5 Hz, 3H).

Step 11. Preparation of ({6-chloro-3-[6-(4-chlorophenoxy)-2-propylpyridin-3-yl]-1,2-benzisoxazol-5-yl}oxy)acetic acid A mixture of the phenol from Step 10 (0.42 g, 1.0 mmol), methyl bromoacetate (0.23 g, 1.5 mmol) and cesium carbonate (0.49 g, 1.5 mmol) in DMF (10 mL) was stirred at room temperature for 2 h. The reaction mixture was diluted with ethyl acetate, washed with water and concentrated. The residue was taken up in methanol (10 mL) and treated with 2 NNaOH (1.5 mL) for 1 h. The mixture was acidified with acetic acid (1 mL) and concentrated. The residue was purified by preparative HPLC on a RP-C18 column using 10-100% acetonitrile in water gradient solvent system modified with 0.1% acetic acid to give the title compound as a white solid.

$^1$H NMR (500 MHz, CDCl$_3$) δ7.80 (s, 1H), 7.77 (d, J=8.5, 1H), 7.42 (d, J=9.0 Hz, 2H), 7.19 (d, J=9.0 Hz, 2H), 6.96 (s, 1H), 6.86 (d, J=8.5 Hz, 1H), 4.74 (s, 2H), 2.70 (t, J=2.5 Hz, 2H), 1.63 (m, 2H), 0.81 (t, J=7.5 Hz, 3H).

MS (ESI, m/z): 473.2 (M$^+$+1).

Example 13

2-({6-chloro-3-[6-(4-chlorophenoxy)-2-propylpyridin-3-yl]-1,2-benzisoxazol-5-yl}oxy)butanoic acid

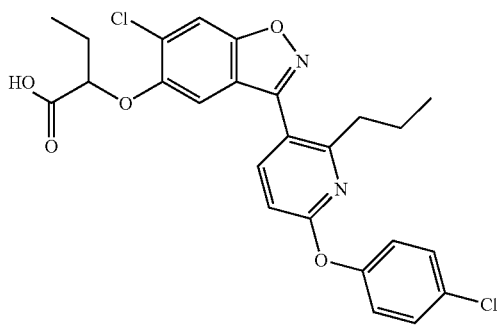

The title compound was prepared according to the same procedure as described for Example 12 except that methyl bromopropanoate was used instead of methyl bromoacetate in step 11.

$^1$H NMR (500 MHz, CDCl$_3$) δ 7.79 (s, 1H), 7.74 (d, J=8.5, 1H), 7.42 (d, J=9.0 Hz, 1H), 7.19 (d, J=9.0 Hz, 2H), 6.93 (s, 1H), 6.85 (d, J=8.5 Hz, 1H), 4.66 (t, J=7.5 Hz, 1H), 2.69 (t, J=7.5 Hz, 2H), 2.12 (m, 2H), 1.62 (m, 2H), 1.16 (t, J=7.5 Hz, 3H), 0.80 (t, J=7.5 Hz, 3H).

MS (ESI, m/z): 501.3 (M$^+$+1).

Example 14

(2S)-2-({6-chloro-3-[6-(4-chlorophenoxy)-2-propylpyridin-3-yl]-1,2-benzisoxazol-5-yl}oxy)propanoic acid

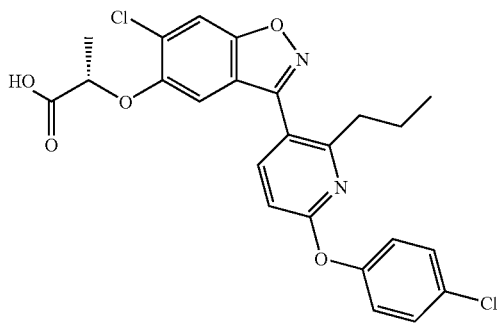

Step 1. Methyl (2S)-2-({6-chloro-3-[6-(4-chlorophenoxy)-2-propylpyridin-3-yl]-1,2-benzisoxazol-5-yl}oxy)propanoate To a solution of the hydroxybenzisoxazole from Step 10 of Example 12 (2.1 g, 5.0 mmol), methyl (R)-lactate (0.78 g, 7.5 mmol) and triphenylphosphine (2.0, 7.5 mmol) in THF (30 mL) cooled in ice bath was added dropwise diethyl azodicarboxylate (1.3 g, 7.5 mmol). The reaction mixture was warmed to room temperature and stirred for 1 h. Acetic acid (0.1 mL) was added and the reaction mixture was concentrated. The residue was triturated with 1:1 diethyl ether:hexane (20 mL) and the mixture was filtered through a column of silica gel to give the title product.

Step 2. (2S)-2-({6-chloro-3-[6-(4-chlorophenoxy)-2-propylpyridin-3-yl]-1,2-benzisoxazol-5-yl}oxy)propanoic acid The ester from Step 1 (2.3 g, 4.5 mmol) was dissolved in methanol (45 mL) and treated with 2 N NaOH (4.5 mL, 9.0 mmol) at room temperature for 1 h. The reaction mixture was acidified with acetic acid (2.0 mL) and methanol was removed under reduced pressure. The residue was taken up in ethyl acetate and the resulting solution was washed with brine and dried over MgSO$_4$. After removal of the solvent, the crude acid was recrystallized in ether-hexane (1:10) to give the title product as a white solid.

$^1$H NMR (500 MHz, CDCl$_3$) δ7.80 (s, 1H), 7.74 (d, J=8.5, 1H), 7.42 (d, J=9.0 Hz, 1H), 7.19 (d, J=9.0 Hz, 2H), 7.01 (s, 1H), 6.85 (d, J=8.5 Hz, 1H), 4.80 (q, J=7.5 Hz, 1H), 2.69 (t, J=2.5 Hz, 2H), 1.76 (d, J=7.5 Hz, 3H), 1.62 (m, 2H), 0.80 (t, J=7.5 Hz, 1H).

MS (ESI, m/z): 486.9 (M$^+$+1).

Alternate Method of Synthesizing Example 14

(2S)-2-({6-chloro-3-[6-(4-chlorophenoxy)-2-propylpyridin-3-yl]-1,2-benzisoxazol-5-yl}oxy)propanoic acid, which is the compound of Example 14, has also been made by the following multi-step route. It is S-14 in steps 9 and 1 0 of the sequence below:

Steps 1 and 2. Esterification and Aryl Ether Formation

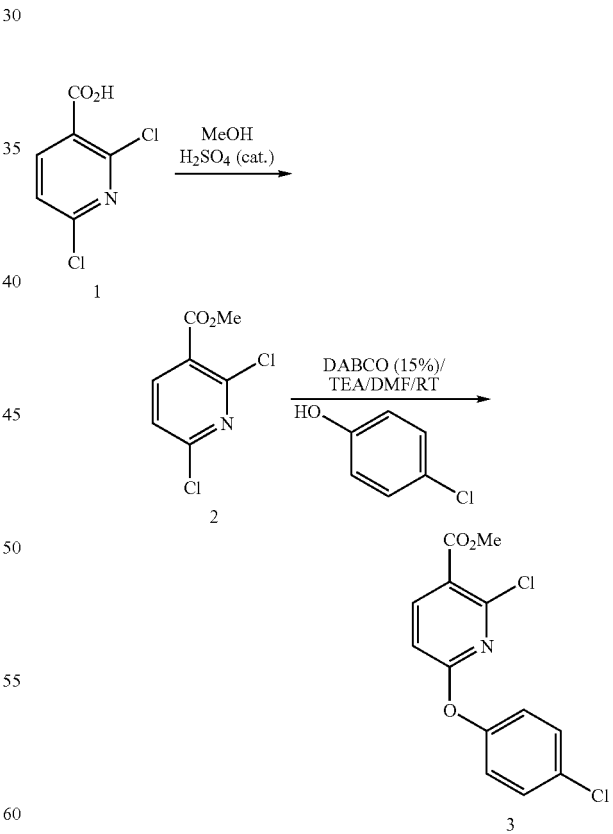

To a solution of 2,6-dichloronicotinic acid (1) (19.2 g, 0.10 mol) in MeOH (100 mL) was added 5.56 mL (0.10 mol) of concentrated H$_2$SO$_4$ dropwise. An ~15° C. temperature increase was observed. The resulting solution was heated at 60° C. for 8-14 hrs.

The reaction mixture was allowed to cool to RT and then poured into a biphasic mixture containing IPAc (220 mL) and aq. $K_2CO_3$ (20.7 g in 117.3 g water) at RT with stirring. The organic layer was separated, washed with sat. $NaHCO_3$ (80 mL), and then water (80 mL). The isolated IPAc solution was subjected to a solvent switch to DMF (80 mL) in vacuo.

A solution of 4-chlorophenol (12.2 g, 0.095 mol) in 36.6 mL of DMF was added at room temperature to the above solution (19.6 g of ester 2, 0.095 mol), followed by addition of triethylamine (17.3 mL, 0.124 mol) at 20-22° C. over 15 min. Solid DABCO (1.6 g, 14.2 mmol) was added to the resulting solution in one portion. A temperature increase of ~3° C. was observed. A water bath was used to maintain the reaction temperature. The reaction was stirred at 22-24° C. for 4-5 h while monitoring by LC until all of the 4-chlorophenol was consumed, resulting in a light slurry. AcOH (2.72 mL, 47.5 mmol) and IPA (57.5 mL) were added to the light slurry, followed by cold water (30 mL) to maintain the internal temperature at 20-25° C. When the water was added, a clear solution first formed, and then a slurry of product formed. After stirring at RT for 0.5 h, additional water (86 mL) was added over 0.5 h. After the slurry was stirred at RT for 1-2 h, it was filtered. The filter cake was washed with mixed solvents (60 mL of IPA:$H_2O$=1:1). The isolated solid was dried in a vacuum-oven at 50° C. for 8 h to provide the product as white cotton-like solid.

Step 3. Propylation

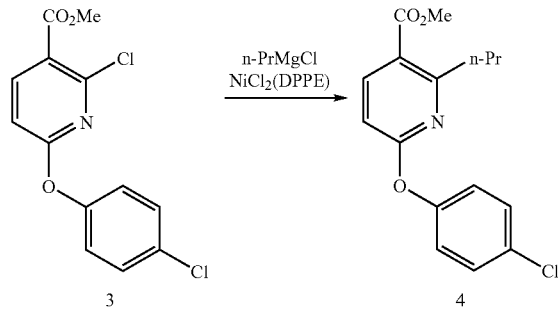

To a solution of methyl 2-chloro-6-(4-chlorophenoxy) nicotinate (12.53 g, 42.03 mmol) and $NiCl_2$dppe (111 mg, 0.5 mol %) in THF (63 mL) was added n-PrMgCl (2.0 M in diethyl ether, 22.5 mL, 45.0 mmol) over ½ h. The reaction was aged at 25° C. to 28° C. for 15 minutes.

The reaction was then quenched with 10% citric acid solution (120 mL) and diluted with MTBE (120 mL). The mixture was stirred over 15 min. The organic layer was cut and was washed with 10% NaCl solution (120 mL). The organic layer (188 mL) was concentrated to 90 mL (½ volume), and 90 mL of MeOH was then added. The volume was again reduced to 90 mL by vacuum distillation. This was repeated 2 additional times to complete the solvent switch to MeOH. The final volume was about 90 mL.

Step 4. Methyl Ester Hydrolysis

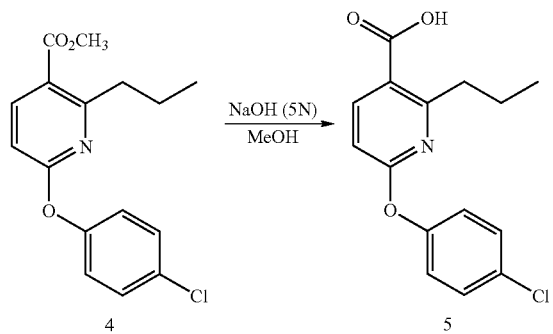

To the solution of 4 from above was added 5N NaOH (13 mL, 65 mmol). The mixture was heated to 68° C. for 2.5 h. LC assay showed the reaction was complete. The reaction can also be run at 50° C., in which case it is typically complete in 4 h. Water (90 mL) was then added to the solution at 68° C., followed by 36 mL of 20% citric acid. The product crystallized from the solution. Water (90 mL) was then added. The slurry was stirred for 2 h and was then filtered. The white cake was washed with 150 mL of water/MeOH (2:1) and was dried in an oven at 62° C. overnight.

Step 5. Friedel-Crafts Acylation

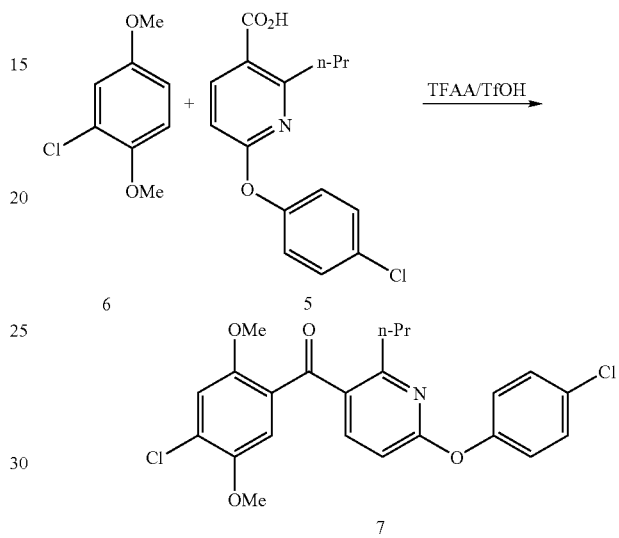

To a 100 L round bottom vessel was charged nicotinic acid 5 (7200 g, 24.68 Mol), which was then dissolved in 17 L of trifluoroacetic anhydride (TFAA). Dimethoxychlorobenzene (6337 mL, 44.42 Mol) was added, followed by slow addition of triflic acid (4426 mL, 2 equivalents), while maintaining the temperature at <40° C. A reflux condenser was attached, and the reaction was heated to 42° C. and stirred overnight. The reaction was assayed, showing a 70% conversion by mass of 5 to 7.

An additional triflic acid charge (440 mL, 0.20 equivalents) was made, and a distillation setup was substituted for the reflux condenser. The batch was heated to 55° C., and ~9 L of TFAA was distilled into an ice cooled 22 L RBF. The batch was aged at 55° C. for 4 hours. At this point the reaction had reached completion.

The reaction was cooled to ambient temperature with an ice bath, and was then quenched into a 100 L extractor at 0° C. onto 30 L (6 molar equivalents) of 5 N KOH and 25 L (3.5 volumes) of toluene, maintaining the temperature at <50° C. for 1 hour. The 100 L flask was rinsed into the extractor with 2×2 L of toluene and 2×2 L of 5N KOH. The phases were separated at room temperature, and the organic phase was washed with 18 L of 1N HCl.

The organic solution was transferred back into the rinsed 100 L vessel and was treated with Darco G-60 (3.6 kg, 50 wt %). The mixture of solution and carbon was heated at 35° C. for 30 min. The charcoal mixture was then filtered through a pad of solka floc, rinsed with 8 L of toluene and vacuum transferred through a 5 uM poly cap, into a visually clean 100 L round bottom flask, with a mark at the 16 L level. The 100 L flask was attached to a batch concentrator and distilled down to the 16 L mark at 35° C. At this point the batch was seeded with 10 g of seed crystals of 7 obtained from an earlier batch, and heptane addition began. After 20 L of heptane had been added the slurry grew thick. The batch was heated to 55° C., and an additional 4 L of heptane was added bringing the total batch volume to the 40 L mark. The slurry was aged at 55° C. for 15 minutes with rapid stirring. At this point a constant volume distillation with the addition of heptane was begun, and the batch temperature was cooled and then was maintained between 30 and 35° C. A total of 80 L of heptane (including the original 24 L) was added to the batch. The solvent composition was checked by $^1$H NMR, and was found to contain 94 mole % heptane.

The slurry was then heated to 65° C. and allowed to slowly cool to room temperature overnight.

The slurry was filtered, and the flask was rinsed with 9 L of a mixture of 95% heptane/5% toluene. The cake was then slurry washed with 9 L of 95% heptane/5% toluene, and then 18 L heptane. The product 7 was dried on the frit under a stream of $N_2$ at ambient temperature.

Step 6. Demethylation of 7 to 8

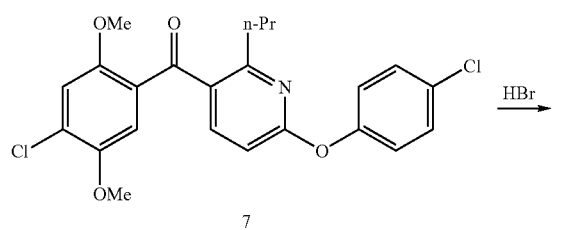

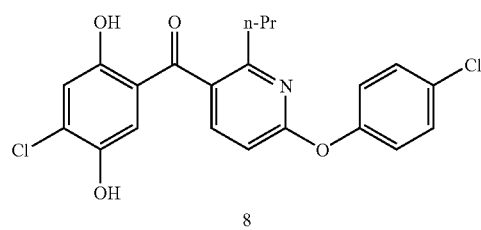

Into a visually clean 200 mL two-neck RBF was charged 11.1 g of solid 93.5 wt % dimethoxyketone 7 (25 mmol), HBr (48% aqueous, 50 mL, 0.5 mol), and HOAc (50 mL, 5×vol). The slurry was heated to 100° C. (dial-in temp.) in 0.5 hours, and the internal temperature gradually stabilized at 95-95.5° C.

The slurry turned dark brown within two hours after the reaction temperature reached 90° C. Further heating for one hour gradually generated bright yellow crystals, and the precipitate became thicker with time. The reaction was stirred at 95-95.5° C. (Internal T) for 24 hours.

The batch was cooled to room temperature, filtered, and sequentially washed with 50 mL HOAc (displacement wash), 50 mL HOAc (slurry wash) and 5% MeOH in water (3×50 mL, slurry washes). The isolated product was dried at r.t. under vacuum over the weekend.

The dry powder product was then suspended in 5% MeOH in water (100 mL) for 4 hours and filtered. The filter cake was washed with 50 mL of water and dried under vacuum to give the final product as the free base.

Step 7. Oxime Formation and Isomerization

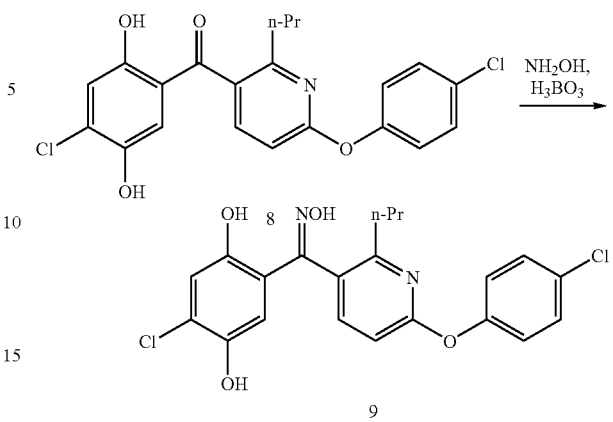

To a 100 L, 4-neck round bottom flask, with mechanical stirrer, reflux condenser, thermocouple and nitrogen/vacuum line, was charged n-propanol (24 L), dihydroquinone ketone (7.598 kg, 89% purity, 6.762 assay kg, 12.38 mol), and boric acid (808 g, 13.07 mol). Hydroxylamine (2.3 L, 37.60 mol) was then poured into the flask. The reaction was heated to reflux (90-92° C.) for 60 minutes.

The reaction was cooled to 30° C. and transferred into a 180-L extractor containing 35 L of water. 15 L of water and 50 L of MTBE were added to the extractor and the mixture was vigorously stirred and allowed to settle. The bottom aqueous layer was cut. The organic layer was washed with 50 L of 20 wt % NaCl (aq), and then with 18 L of 20 wt % NaCl (aq).

The organic layer was agitated with 3 kg of sodium sulfate and 1 kg of DARCO G-60 and filtered through a bed of Solkaflok. The cake bed was rinsed with 15 L of MTBE. The filtrate was concentrated to approximately 20 L at 35-40° C., 20-25 in. Hg. n-Propanol (60 L) was fed and distilled at 35-40° C., 28-30 in. Hg, while maintaining a constant volume of 20 L. The final batch KF was 860 ppm water.

The resulting solution was heated on a steam pot to 93-97° C. The reaction was monitored for isomerization conversion. After 6 hours, the batch was allowed to cool to ambient temperature. 200 mL of the batch was sampled for seed formation. To the stirring solution, 50 mL of water was added, and then 1 g of seed was added, and the batch was aged to form a seed bed. The remaining 250 mL of water was added to complete the crystallization.

To the batch, 5 L of water was added, followed by the seed slurry. The mixture was aged, giving a thick slurry. The remaining 25 L of water was added over 1 hour. The slurry was heated to 50° C. and cooled to ambient temperature.

The solid was isolated by filtration. The cake was washed with 2:1 water/n-propanol (8 L, 8 L, 12 L, 12 L), water (8 L), then hexanes (12 L, 8 L). The solid was dried on the filter under a nitrogen tent. The E-oxime was obtained as an orange solid.

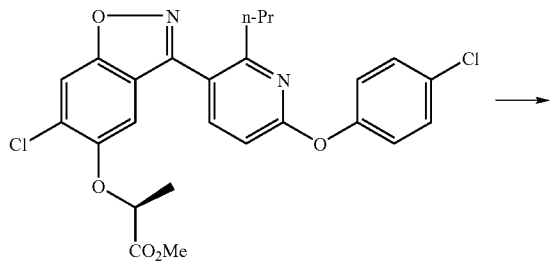

Step 8. Benzisoxazole Formation

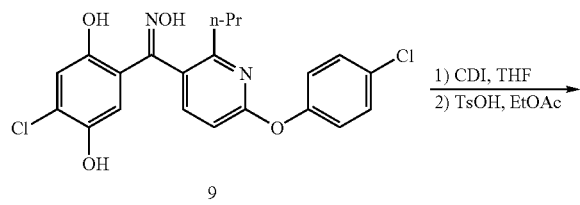

9

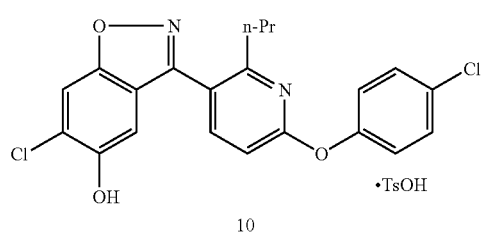

10

To a 100 L cylindrical vessel with cooling coils, thermocouple, and nitrogen/vacuum inlets, was charged THF (23 L) and the oxime (4.953 kg, 4.661 assay kg, 10.76 mol). The dark brown solution was cooled to −15° C. CDI (2.70 kg, 16.65 mol) was added in two portions over 10 minutes. The reaction was aged at −5-0° C. for 1 hour.

The reaction was then warmed to 25° C. MeOH (1.3 L) was added, and the solution was aged for 1 hour.

To the reaction, 35 L of MTBE, 20 L of water, and 2.5 L of 85% phosphoric acid were added with vigorous stirring. After settling, the bottom aqueous layer was cut. The organic layer was washed with water (20 L), 0.5 M $Na_2CO_3$ (2×20 L), 1M $H_3PO_4$ (20 L), then 10 wt % $KH_2PO_4$ (4 L).

The batch was stirred with 1 kg of DARCO G-60 for 1.5 hours. The mixture was filtered through Solkaflok and the bed was washed with 14 L of MTBE.

The filtrate was fed into a 100 L round bottom flask equipped with mechanical stirrer, thermocouple, and nitrogen inlet, and was attached to a batch concentrator. The batch was fed and distilled at 35-40° C., 16-20 in. Hg, maintaining the batch volume at 20-25 L. EtOAc (40 L) was then fed and distilled at 35-40° C., 20-23 in. Hg at a constant volume of 15-20 L.

To a 100 L cylindrical vessel with heating coils were charged EtOAc (20 L) and $TsOH/H_2O$ (2.304 kg, 12.11 mol), and the mixture was heated to 35-45° C. to dissolve. The acid solution was fed into the isoxazole batch with further distilling, maintaining a constant volume of 25 L. An additional 20 L of EtOAc was distilled to azeotropically dry the mixture. A slurry began to form, and it continued to thicken on addition and concentration. The final KF was 400 ppm water. The batch was heated to 60° C. and allowed to slowly cool to ambient temperature overnight.

The solid product was isolated by filtration. The cake was washed with EtOAc (16 L), then with MeCN (24 L), and was dried on the filter under a nitrogen tent. The benzisoxazole tosylate was obtained as a pale yellow solid.

Step 9A. Lactate Tosylate Formation

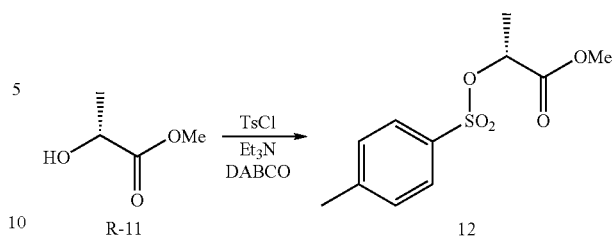

To a 50 L RBF was added 1.50 kg R-methyl lactate, which was then dissolved in EtOAc (7.5 L) with 3.02 kg tosyl chloride. The batch was cooled with ice to 6° C. A mild endotherm was noted on mixing.

DABCO (242 g) and triethylamine (3.01 L) were separately dissolved in the 7.5 L of EtOAc. The solution was charged to a 50 L vessel, maintaining the temperature below 25° C. The reaction was aged 2 h at room temperature. A mild to moderate delayed exotherm was seen. A white slurry formed during the addition.

To a 50 L extractor 4 L of water and 3 L of EtOAc were added with stirring. Water (3.5 L) was added to the reaction vessel, and the biphasic solution was transferred to the extractor. The vessel was then rinsed with 4.5 L EtOAc. To the stirred extraction was added 7.5 L of 2 N HCl, bringing the total extraction volume to 40 L. The extraction was aged 10 min and phase separated. The organic was washed with 7.5 L of water and then 15 L of 4% $NaHCO_3$ (aq). The organic solution was then transferred to clean plastic carboys, and dried over $Na_2SO_4$ (5 kg) in the carboys.

The batch was then filtered through a 20 uM poly cap filter into a Buchi rotary evaporator, yielding the product as an oil containing residual ethyl acetate (3 wt %) and 700 PPM water. The batch was transferred to a container and was stored in a cold room until it was used. The product had an ee of 98.2%.

Step 9. Methyl Lactate Attachment

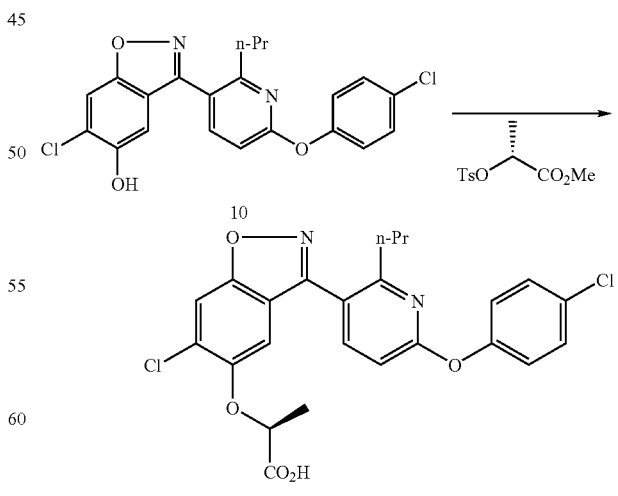

To a 100 L RBF was added benzisoxazole tosylate 10 (5.7 kg, 10 moles), then $K_2CO_3$ powder (5.7 kg, 42 moles), and then 25 L DMSO. A slight exotherm was noted. The reaction was stirred for 10 min, and the mixture was degassed and placed under N$_2$. The slurry was cooled to <30° C., and the lactate tosylate 12 (2.8 kg, 11 moles) was added. The mixture was stirred for 2-4 hrs until HPLC showed >98% conversion. To the reaction was added 20 L MTBE and 30 L cold water. The cold water was added to moderate the slight exotherm on quenching. The layers were agitated for 10 min.

The mixture was transferred to a 180 L cyclindrical vessel, and an additional 30 L MTBE and 30 L cold water were added. The layers were cut and the aqueous layer was back extracted with 25 L MTBE. The combined organic layers were washed with 18 L 2% NaHCO$_3$. The final organic layer was fed with concurrent distillation into a 100 L RBF and solvent switched to acetonitrile. The batch was kept at 25-30° C. to prevent crystallization.

The batch volume was adjusted to 45 L with acetonitile, and 36 L water was added slowly (product crystallizes after 4 L water is added). After overnight aging, the batch was filtered, and the cake was washed with 10 L 1/1 MeCN/water. Solid methyl ester S-13 on the funnel was dried with suction under nitrogen flow for 4 days.

Step 10. Hydrolysis and Final Crystallization

In a 50 L cyclindrical vessel, the methyl ester S-13 (2.3 kg) was dissolved in 12.5 L MeCN and mixed with 10 L 1N NaOH. The solution was aged for 2-3 hrs at ambient temperature. Toluene (25 L) was added, followed by conc. HCl to bring the pH to 2-3 (0.85 L). The resulting layers were separated. The organic layer was washed with 15 L brine and dried with Na$_2$SO$_4$ and 0.7 kg Ecorsorb C-933. The slurry was filtered and the cake was washed with 10 L toluene. In a 100 L RBF, the filtrate was batch concentrated to 15 L.

The batch volume was then adjusted to 18 L (8 L toluene/kg product). The batch was heated to 50° C., and 56 L of methylcyclohexane was added at 50° C. The batch was seeded with crystals from earlier batches after 18 L of methylcyclohexane was added. The batch was cooled slowly to ambient temperature (about 10 min per degree) to yield crystalline product S-14. The batch became thick at around 39° C. The batch was cooled further to ambient temperature over 4-8 hrs. It was aged a total of 16 hrs.

The batch was filtered, and the cake was washed with 10 L of 4:1 methylcyclohexane/toluene, then 2×10 L of methylcyclohexane. It was dried on the filter pot under vacuum and nitrogen flow overnight, and was then transferred to a vacuum oven and dried with nitrogen flow overnight.

Compound 10 in the above preparation may be used as an intermediate in making any of the compounds disclosed in Examples 12-19.

Compounds in Examples 15 through 19 below were prepared according to procedures similar to those described for Examples 12 to 14.

Example 15

(2S)-2-({6-chloro-3-[6-(4-fluorophenoxy)-2-propylpyridin-3-yl]-1,2-benzisoxazol-5-yl}oxy)propanoic acid

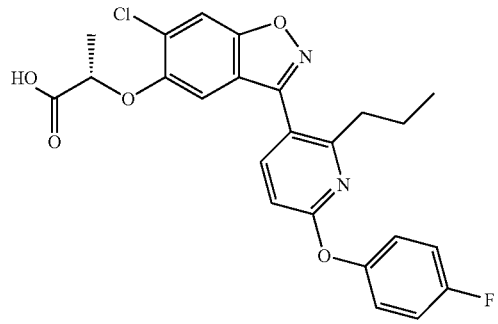

$^1$H NMR (500 MHz, CDCl$_3$) δ 7.81 (d, J=8.5, 1H), 7.80 (s, 1H), 7.21-7.26 (m, 2H), 7.15-7.20 (m, 2H), 7.00 (s, 1H), 6.81 (d, J=8.5 Hz, 1H), 4.79 (q, J=7.5 Hz, 1H), 2.76 (t, J=2.5 Hz, 2H), 1.76 (d, J=7.5 Hz, 3H), 1.67 (m, 2H), 0.81 (t, J=7.5 Hz, 3H).

MS (ESI, m/z): 471.2 (M$^+$+1).

Example 16

(2S)-2-{[6-chloro-3-(6-phenoxy-2-propylpyridin-3-yl)-1,2-benzisoxazol-5-yl]oxy}propanoic acid

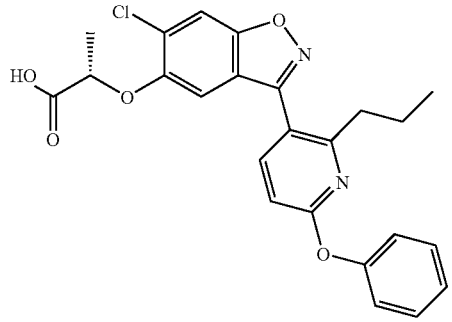

$^1$H NMR (500 MHz, CDCl$_3$) δ 7.80 (s, 1H), 7.75 (d, J=8.5, 1H), 7.47 (t, J=8.5 Hz, 2H), 7.29 (t, J=8.5 Hz, 1H), 7.25 (d, J=8.5 Hz, 2H), 7.02 (s, 1H), 6.82 (d, J=8.5 Hz, 1H), 4.80 (q, J=7.5 Hz, 1H), 2.75 (t, J=2.5 Hz, 2H), 1.78 (d, J=7.5 Hz, 3H), 1.66 (m, 2H), 0.82 (t, J=7.5 Hz, 3H).

MS (ESI, m/z): 453.2 (M$^+$+1).

Example 17

(2R)-2-({6-chloro-3-[6-(4-chlorophenoxy)-2-propylpyridin-3-yl]-1,2-benzisoxazol-5-yl}oxy)propanoic acid

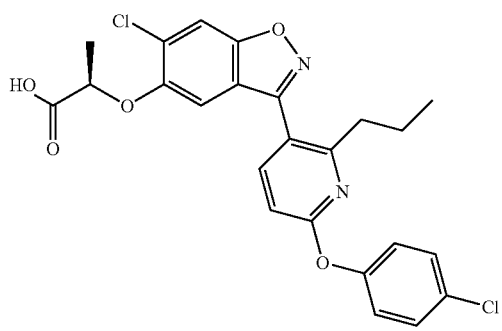

$^1$H NMR (500 MHz, CDCl$_3$) δ 7.80 (s, 1H), 7.74 (d, J=8.5, 1H), 7.42 (d, J=9.0 Hz, 2H), 7.19 (d, J=9.0 Hz, 2H), 7.01 (s, 1H), 6.85 (d, J=8.5 Hz, 1H), 4.80 (q, J=1H), 2.69 (t, J=2.5 Hz, 2H), 1.76 (d, J=7.5 Hz, 3H), 1.62 (m, 2H), 0.80 (t, J=7.5 Hz, 3H).

MS (ESI, m/z): 486.9 (M$^+$+1).

Example 18

(2S)-2-({6-chloro-3-[6-(4-cyanophenoxy)-2-propylpyridin-3-yl]-1,2-benzisoxazol-5-yl}oxy)propanoic acid

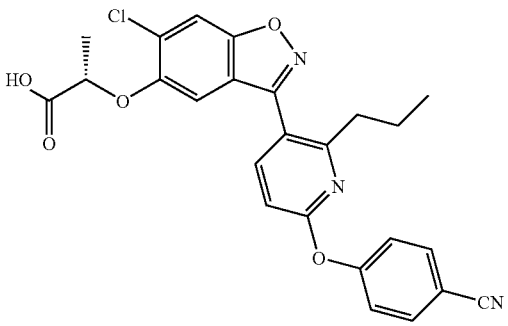

$^1$H NMR (500 MHz, CDCl$_3$) δ 7.83 (d, J=8.5, 1H), 7.82 (s, 1H), 7.77 (d, J=9.0 Hz, 2H), 7.37 (d, J=9.0 Hz, 2H), 7.01 (s, 1H), 6.98 (d, J=8.5 Hz, 1H), 4.82 (q, J=7.5 Hz, 1H), 2.71 (t, J=2.5 Hz, 2H), 1.76 (d, J=7.5 Hz, 3H), 1.63 (m, 2H), 0.81 (t, J=7.5 Hz, 3H).

MS (ESI, m/z): 478.22 (M$^+$+1).

Example 19

(2S)-2-({6-chloro-3-[6-(4-chlorophenoxy)pyridin-3-yl]-1,2-benzisoxazol-5-yl}oxy)propanoic acid

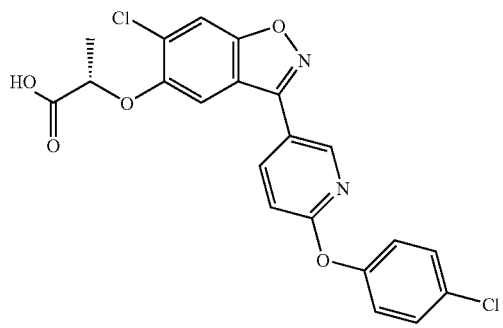

$^1$H NMR (500 MHz, CDCl$_3$) δ 8.9 (s, 1H), 8.39 (d, J=8.0, 1H), 7.80 (s, 1H), 7.46 (s, 1H), 7.40 (d, J=8.5 Hz, 2H), 7.12 (d, J=8.0 Hz, 1H), 7.10 (d, J=8.5 Hz, 2H), 5.02 (q, J=7.5 Hz, 1H), 1.77 (d, J=7.5 Hz, 3H).

MS (ESI, m/z): 445.0 (M$^+$+1).

Example 20

(2S)-2-({6-chloro-3-[6-(4-chlorophenoxy)-2-propylpyridin-3-yl]-1-methyl-1H-indazol-5-yl}oxy)propanoic acid

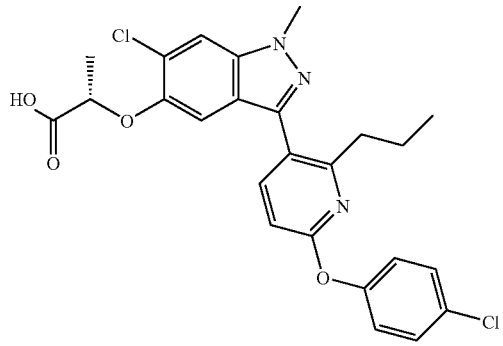

Step 1. Preparation of 6-chloro-3-[6-(4-chlorophenoxy)-2-propylpyridin-3-yl]-5-methoxy-1-methyl-1H-indazole A solution of the ketone from Step 7 of Example 12 (0.86 g, 2.0 mmol) and methylhydrazine (0.18 g, 4.0 mmol) in DMSO (10 mL) was heated at 80° C. for 1 h. The mixture was diluted with ethyl acetate, washed with water and dried over magnesium sulfate. After removal of the solvent, the residue was purified by chromatography on silica gel to give the title product.

Step 2. Preparation of 6-chloro-3-[6-(4-chlorophenoxy)-2-propylpyridin-3-yl]-1-methyl-1H-indazol-5-ol The compound from Step 1 was treated with boron tribromide dimethylsulfide complex according to the procedure described in Step 9 of Example 12 to give the title product as a solid.

Step 3. Preparation of (2S)-2-({6-chloro-3-[6-(4-chlorophenoxy)-2-propylpyridin-3-yl]-1-methyl-1H-indazol-5-yl}oxy)propanoic acid, sodium salt The phenol from Step 2 (0.43 g, 1.0 mmol) and methyl (R)-lactate (0.16 g, 1.5 mmol) were reacted according the general procedure described in Step 11 of Example 1 to give the title compound as a white solid.

$^1$H NMR (500 MHz, CD$_3$OD) δ 7.83 (d, J=8.5 Hz, 1H), 7.71 (s, 1H), 7.42 (d, J=8.5 Hz, 2H), 7.18 (d, J=8.5 Hz, 2H), 6.98 (s, 1H), 6.86 (d, J=8.5 Hz, 1H), 4.40 (m, 1H), 4.07 (s, 3H), 2.71 (m, 2H), 1.59 (d, J=6.5 Hz, 3H), 1.55 (m, 2H), 0.75 (t, J=8.5 Hz, 3H).
MS (ESI, m/z): 500.2 (M$^+$+1).

Example 21

(2S)-2-({6-chloro-3-[6-(4-chlorophenoxy)-2-propylpyridin-3-yl]-1H-indazol-5-yl}oxy)propanoic acid

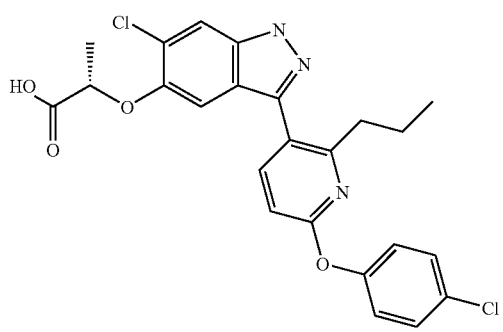

The title compound was prepared by following the same procedure as described for Example 20 using hydrazine instead of methyhydrazine in Step 1.

$^1$H NMR (500 MHz, CD$_3$OD) δ 7.73 (d, J=8.5 Hz, 1H), 7.62 (s, 1H), 7.32 (d, J=8.5 Hz, 2H), 7.15 (d, J=8.5 Hz, 2H), 6.92 (s, 1H), 6.85 (d, J=8.5 Hz, 1H), 4.40 (q, J=6.5 Hz, 1H), 2.71 (m, 2H), 1.59 (d, J=6.5 Hz, 3H), 1.55 (m, 2H), 0.80 (t, J=7.5 Hz, 3H).
MS (ESI, m/z): 487.2 (M$^+$+1).

Example 22

(2S)-2-{[6-chloro-3-[6-(4-chlorophenoxy)-2-propylpyridin-3-yl]-1-(methylsulfonyl)-1H-indazol-5-yl]oxy}propanoic acid

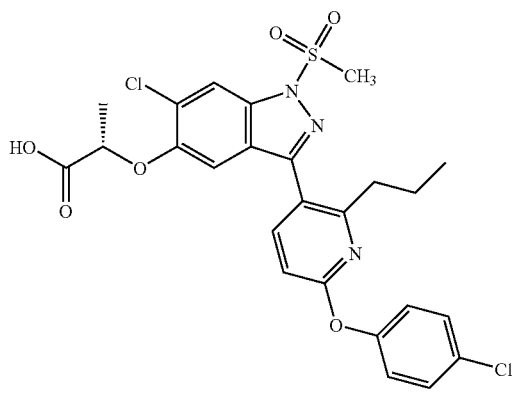

To a solution of the title compound in Example 21 (49 mg, 0.10 mmol) in THF (1 mL) cooled with an ice bath was added sodium hydride (23 mg, 1.0 mmol). The solution was stirred at 0° C. for 30 min and methanesulfonylchloride (0.077 mL, 1.0 mmol) was added. The reaction mixture was warmed to room temperature and quenched with brine (2 mL). After addition of ethyl acetate (5 mL), the organic layer was separated and dried over MgSO$_4$ and concentrated. The residue was purified by preparative HPLC on a RP-C18 column using 10-100% acetonitrile in water gradient solvent system modified with 0.1% acetic acid to give the title compound as a white solid.

$^1$H NMR (500 MHz, CD$_3$OD) δ 7.83 (d, J=8.5 Hz, 1H), 7.82 (s, 1H), 7.53 (d, J=8.5 Hz, 2H), 7.25 (d, J=8.5 Hz, 2H), 6.99 (s, 1H), 6.89 (d, J=8.5 Hz, 1H), 4.41 (q, J=6.5 Hz, 1H), 2.86 (s, 3H), 2.72 (m, 2H), 1.61 (d, J=6.5 Hz, 3H), 1.50 (m, 2H), 0.81 (t, J=7.5 Hz, 3H).
MS (ESI, m/z): 565.3(MH$^+$).

Example 23

(2S)-2-({8-[4-(4-fluorobenzoyl)phenyl]-2-naphthyl}oxy)propanoic acid

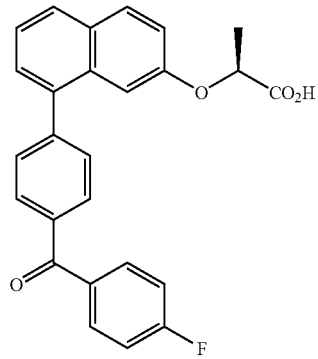

Scheme 3 provides an overview of the synthesis of this compound. The synthesis is described in detail after Scheme 3.

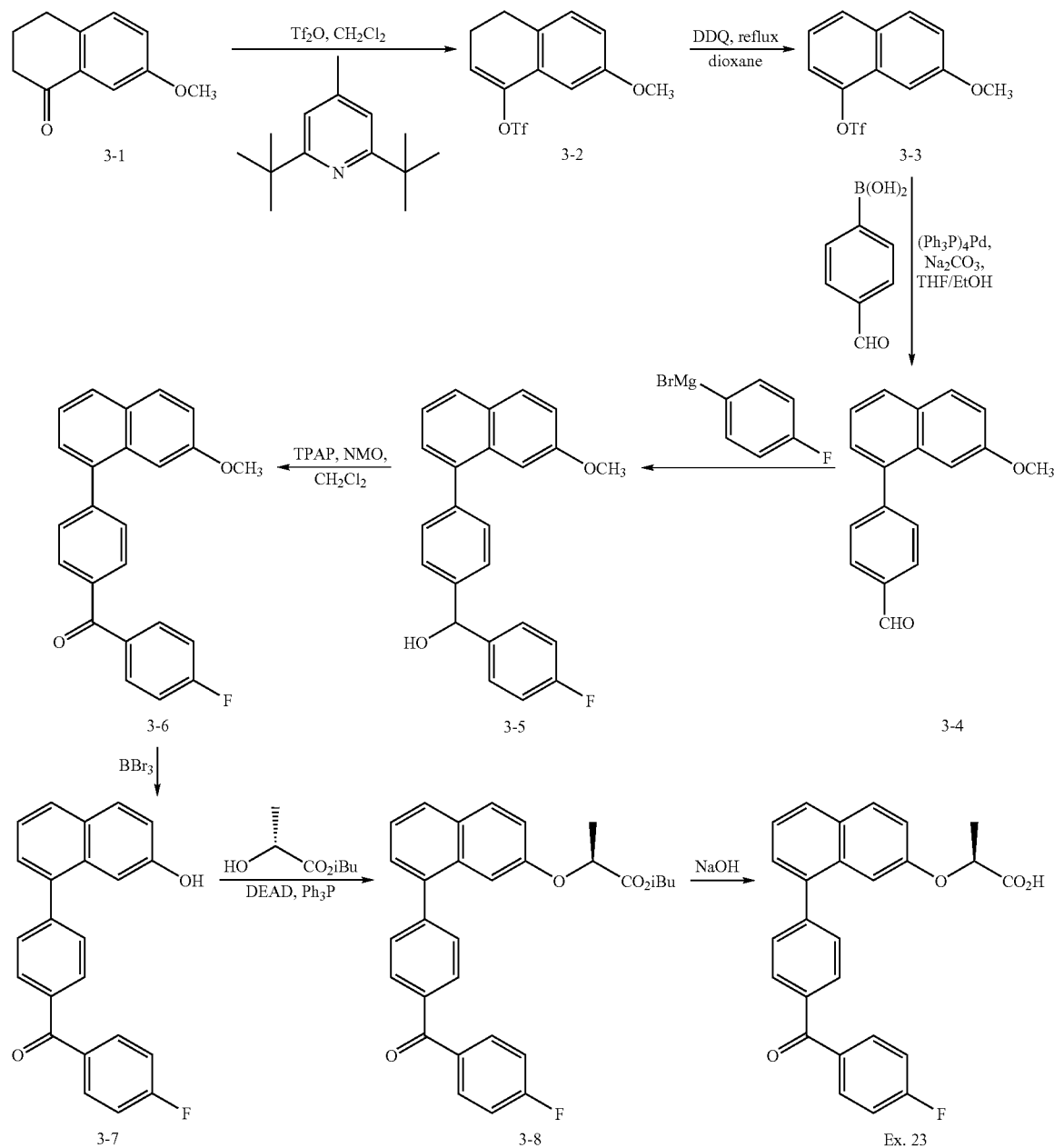

Step 1. Preparation of Compound 3-2

Triflic anhydride (1.05 mL, 6.25 mmole, 1.1 equiv.) was added drop-wise to a mixture of 7-methoxytetralone (Compound 3-1) (1.0 gr, 5.68 mmole) and 2,6-di-tert-butyl-4-methyl pyridine (1.28 gr, 6.25 mmole, 1.1 equiv.) stirring in methylene chloride (28 mL, 0.2 M) at 0° C. under an atmosphere of nitrogen. After the addition was complete the reaction was warmed to room temperature and stirred for 30 minutes. After this time the reaction was diluted with ethyl ether (100 mL) and then was washed with saturated $NaHCO_3$ solution (1×), $H_2O$ (1×) and brine (1×). The organic layer was dried over $MgSO_4$, was filtered to remove drying agent, and the solvent was removed under reduced pressure to provide a crude oil. The crude oil was purified on $SiO_2$ eluting with hexanes/ethyl acetate (gradient elution, 95:5 to 50:50) to give compound 3-2 as an oil.

$^1$H NMR (500 MHz, $CDCl_3$) 7.1 (1H, d, 8.3 Hz), 6.93 (1H, d, 2.6 Hz), 6.83 (1H, dd, 2.6, 8.3 Hz), 6.06 (1H, t, 4.7 Hz), 3.83 (3H, s), 2.82 (2H, t, 8 Hz), 2.52 (2H, m).

Step 2. Preparation of Compound 3-3

A mixture of the enol triflate 3-2 (219 mg, 0.71 mmole) and DDQ (194 mg, 0.852 mmole, 1.2 equiv.) was stirred in dioxane (2.8 mL, 0.25M) at reflux for 1.5 hr. After this time the reaction was cooled to room temperature and filtered through a bed of silica. The silica was then washed with hexanes/ethyl acetate (7:3; 100 mL). The combined washes were concentrated under reduced pressure to afford compound 3-3 as a light tan oil that was used without further purification.

$^1$H NMR (600 MHz, CDCl$_3$) 7.81 (1H, d, 9.0 Hz), 7.80 (1H, d, 8.0 Hz), 7.44 (1H, d, 7.8 Hz), 7.34 (1H, t, 7.9 Hz), 7.32 (1H, d, 2.3 Hz), 7.25 (1H, dd, 2.4, 8.9 Hz), 3.97 (3H, s).

Step 3. Preparation of Compound 3-4

A biphasic suspension of triflate 3-3 (195 mg, 0.633 mmole), 4-formylphenylboronic acid (114 mg, 0.76 mmole, 1.2 equiv.), and palladium (0) tetrakis-(triphenylphosphine) (73 mg, 0.12 mmole, 0.1 equiv.) was stirred at reflux in toluene (4.8 ml), ethanol (1.5 mL), and 2M Na$_2$CO$_3$ (0.7 mL) for 2 hr. After this time the reaction was cooled to room temperature and diluted with ether (100 mL), then washed with H2O (2×) and brine (1×). The organic layer was dried over MgSO$_4$ and filtered to remove drying agent, and the solvent was then removed under reduced pressure to provide compound 3-4 as a crude oil. The crude oil was purified on SiO$_2$ eluting with hexanes/ethyl acetate (gradient elution, 95:5 to 50:50) to give an oil.

$^1$H NMR (500 MHz, CDCl$_3$) 10.15 (1H, s), 8.05 (2H, d, 8 Hz), 7.87 (2H, d, 8.7 Hz), 7.73 (2H, d, 8 Hz), 7.43 (2H, m), 7.22 (1H, dd, 2.6, 9.0 Hz), 7.16 (1H, d, 2.6 Hz), 3.79 (3H, s).

Step 4. Preparation of Compound 3-5

A solution of 4-fluorophenyl magnesium bromide (0.56 mL, 0.65 mmole, 1 M in ether) was added dropwise to a stirring solution of aldehyde 3-4 (142 mg, 0.541 mmole) in tetrahydrofuran (5 mL, 0.1M) at −78° C. under an atmosphere of nitrogen. After 20 min the reaction was warmed to room temperature. Then the reaction was quenched with an aqueous solution of ammonium chloride (5 mL). The mixture was diluted with ether (100 mL) and then was washed with H$_2$O (2×) and brine (1×). The organic layer was dried over MgSO$_4$, filtered to remove drying agent and the solvent removed under reduced pressure to provide compound 3-5 as an unstable crude oil that was used immediately without purification.

Step 5. Preparation of Compound 3-6

TPAP (19 mg, 0.54 mmole, 0.1 equiv.) was added to a stirring solution of the bis-benzylic alcohol 3-5 (0.541 mmole), 0.1 M) and N-methyl morpholine-N-oxide (76 mg, 0.65 mmole, 1.5 equiv.) in methylene chloride (5 mL, 0.1 M) at 0° C. After 3 hr the reaction was filtered through SiO$_2$ then the SiO$_2$ was washed with hexanes/ethyl acetate (7:3, 30 mL). The combined washes were concentrated under reduced pressure to afford compound 3-6 an oil.

$^1$H NMR (500 MHz, CDCl$_3$) 7.99-7.95 (4H, m), 7.87-7.86 (2H, m), 7.68 (2H, d, 8.2 Hz), 7.45 (2H, m), 7.26-7.22 (4H, m), 3.82 (3H, s).

Step 6. Preparation of Compound 3-7

Boron tribromide (0.703 mL, 0.703 mmole, 1.3 equiv., 1.0 M in CH$_2$Cl$_2$) was added dropwise to a stirring solution of ether 3-6 in CH$_2$Cl$_2$ at 0° C. under an atmosphere of nitrogen. After the addition was complete the reaction was warmed to room temperature then stirred for another 1.5 hr. The reaction was quenched with ice-water and stirred for 15 min. The biphasic mixture was diluted with ether (100 mL) and was then washed with H$_2$O (1×) and brine (1×). The organic layer was dried over MgSO$_4$, filtered to remove drying agent, and the solvent was removed under reduced pressure to provide a crude oil. The crude oil was purified on SiO$_2$, eluting with hexanes/ethyl acetate (gradient elution, 95:5 to 50:50) to give compound 3-7 as a yellow solid.

$^1$H NMR (500 MHz, CDCl$_3$) 7.98-7.92 (4H, m), 7.89-7.85 (2H, m), 7.25-7.22 (3H, m), 7.17 (1H, dd, 2.5, 8.7 Hz), 5.12 (1H, br s).

Step 7. Preparation of Compound 3-8

Diethyl azidodicarboxylate (0.024 mL, 0.148 mmole, 1.5 equiv.) was added to a stirring solution of biaryl phenol 3-7 (34 mg, 0.099 mmole), triphenyl phosphine (39 mg, 0.148 mmole, 1.5 equiv.) and iso-butyl-(R)-lactate (0.023 mL, 0.148, 1.5 equiv.) in CH$_2$Cl$_2$ (1 mL, 0.1M) at room temperature under an atmosphere of nitrogen. After 1.5 hr the reaction was purified directly without workup on SiO$_2$ (hexanes/ethyl acetate, 4:1) to give compound 3-8 as an oil.

$^1$H NMR (500 MHz, CDCl$_3$) 8.00-7.93 (4H, m), 7.89-7.85 (2H, m), 7.62 (2H, d, 8 Hz), 7.47-7.43 (2H, m), 7.27-7.22 (3H, m), 7.18 (1H, d, 2.5 Hz), 4.77 (1H, q, 6.8 Hz), 3.94 (1H, dd, 6.9, 10.5 Hz), 3.80 91H, dd, 6.9, 10.5 Hz), 1.83 (1H, septet, 6.9 Hz), 1.65 (3H, d, 6.8 Hz), 0.81 (6H, t, 6.8 Hz).

Step 8. Preparation of (2S)-2-({8-[4-(4-fluorobenzoyl)phenyl]-2-naphthyl}oxy)propanoic acid The isobutyl ester 3-8 (38mg, 0.081 mmole) was stirred with 1 M aqueous NaOH in THF/methanol (1:1, 0.4 mL) for 18 hr. The reaction was purified directly by prep TLC (20 cm×20 cm plate, SiO$_2$, 1000 microns, hexanes/ethyl acetate/ HOAc, 7:3:0.1) to give the title compound as a solid.

$^1$H NMR (500 MHz, CDCl$_3$) 7.94-7.90 (2H, m), 7.83-7.80 (2H, m), 7,72 (2H, d, 6.9 Hz), 7.43 (1H, d, 7.1 Hz), 7.32-7.25 (3H, m), 7.24-7.21 (2H, m), 7.18 (1H, dd, 2.5, 8.9 Hz), 7.11 (1H, d, 2.2 Hz), 4.71 (1H, q, 6.7 Hz), 1.67 (3H, d, 6.7 Hz). MS (M+H) 415.

Example 24

({8-[2-(4-chlorophenoxy)pyrimidin-5-yl]-2-naphthyl}oxy)acetic acid

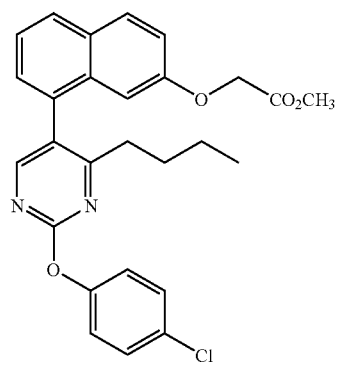

Scheme 4 provides an overview of the synthesis of this compound. The synthesis is described in detail after Scheme 4.

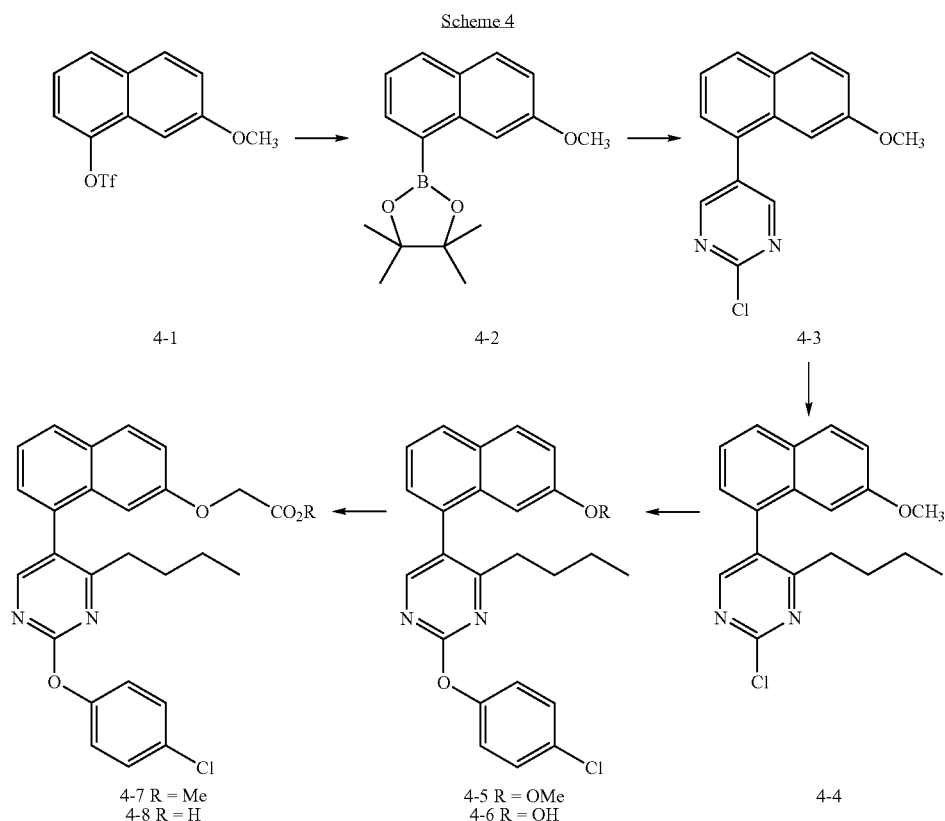

Scheme 4

A mixture of aryl triflate 4-1 (575 mg, 1.88 mmole), bis-pinacolatoborane (715 mg, 2.81 mmol, 1.5 equiv), PdCl$_2$dppf (76 mg, 0.094 mmole, 0.05 equiv) and potassium acetate (553 mg, 5.64 mmole, 3 equiv) was stirred in dioxane (9 mL) under a nitrogen atmosphere. After 24 hr, the reaction was diluted with ethyl acetate/water (1:1, 200 mL). The ethyl acetate layer was washed with water (25 mL), then brine (25 mL), and then was dried with MgSO$_4$. After filtering off the drying agent, the solvent was removed under reduced pressure, and the crude oil was purified on SiO$_2$ eluting with hexanes/ethyl acetate (gradient elution, 0% to 50% ethyl acetate) to give 4-2 as a colorless solid. $^1$H NMR (500 MHz, CDCl$_3$) 8.25 (1H, d, J=2.7 Hz), 8.06 (1 H, dd, J=6.9, 1.4 Hz), 7.85 (1H, d, J=8.0 Hz), 7.75 (1H, d, J=9.0 Hz), 7.35 (1H, dd, J=8.0, 6.9 Hz), 7.17 (1H, dd, J=9.0, 2.7 Hz), 3.98 (s, 3H), 1.45 (s, 12H).

A mixture of 4-2 (135 mg, 0.474 mmole), 2-chloro-5-bromo pyrimidine (92 mg, 0.474 mmole, 1.0 equiv) and Cs$_2$CO$_3$ (250 mg, 0.711 mmole, 1.5 equiv) in DMF (2.4 mL) was degassed (3 freeze-pump-thaw cycles). Palladium tetrakis(triphenylphosphine) (29 mg, 0.025 mmol, 0.05 equiv) was added, and then the yellow suspension was heated at 80-85° C. under a nitrogen atmosphere for 14 hr. The reaction was cooled to room temperature and diluted with ethyl acetate/water (1:1, 100 mL). The ethyl acetate was washed with water (2×20 mL), brine (1×20 mL) then dried with MgSO$_4$. After filtering off the drying agent the solvent was removed under reduced pressure and the crude oil was purified on SiO$_2$ eluting with hexanes/ethyl acetate (gradient elution, 0% to 75% ethyl acetate) to give 4-3 as a colorless solid. $^1$H NMR (500 MHz, CDCl$_3$) 8.84 (2H, s), 7.93 (1h, d, J=8.0 Hz), 7.89 (1H, d, J=8.9 Hz), 7.48 (1H, t, J=7.2 Hz), 7.39 (1H, dd, 7.2, 1.1 Hz), 7.26 (1H, dd, J=8.9, 2.4 Hz), 7.01 (1H, d, J=2.4 Hz), 3.85 (3H, s). MS (M+H) 271.

n-Butyl lithium (230 uL, 0.366 mmole, 1.1 equiv, 1.6 M in hexanes) was added to a solution of 4-3 (90 mg, 0.332 mmole) in THF (1.6 mL) at −78° C. After the addition was complete the reaction was warmed to 0° C., then was quenched with a slight excess of water. A solution of DDQ (52 mg, 0.366 mmole, 1.1 equiv) in THF (1.6 mL) was added to the reaction. After 15 minutes the reaction was diluted with 1N NaOH (1 mL) and ether (100 mL). The ether layer was washed with water (2×20 mL), then brine (20 mL), and then was dried with MgSO$_4$. After filtering off the drying agent the solvent was removed under reduced pressure and the crude oil was purified on SiO$_2$, eluting with hexanes/ethyl acetate (gradient elution, 0% to 75% ethyl acetate) to give 4-4 as a colorless solid. $^1$H NMR (500 MHz, CDCl$_3$) 8.49 (1h, s), 7.93 (1H, d, j=8.0 Hz), 7.89 (1H, d, J=8.9 Hz), 7.47 (1H, dd, j=8.1, 7.1 Hz), 7.32 (1H, dd, j=7.0, 1.1 Hz), 7.25 (1H, dd, j =8.9, 2.5 Hz), 6.59 (1H, d, j=2.5 Hz), 3.79 (3H, s), 3.79-2.59 (1H, m), 2.55-2.49 (1H, m), 1.63-1.59 (2H, m), 1.30-1.15 (2H, m), 0.74 (3H, t, j=7.3 Hz). MS (M+H) 327.

A slurry of 44 (59 mg, 0.181 mmole), p-chlorophenol (23 mg, 0.181 mmole, 1.0 equiv) and Cs$_2$CO$_3$ (76 mg, 0.217 mmole, 1.2 equiv) in DMF (0.9 mL) was heated at 100° C. under an atmosphere of nitrogen for 1.5 hr. The reaction was cooled to room temperature, and then was diluted with ether (100 mL). The ether was washed with water (3×20 mL), then brine (20 mL), and then dried with MgSO$_4$. After filtering off the drying agent the solvent was removed under reduced pressure and the crude oil was purified on SiO$_2$ eluting with hexanes/ethyl acetate (gradient elution, 0% to 75% ethyl acetate) to give 4-5 as a colorless solid. $^1$H NMR (500 MHz, CDCl$_3$) 8.34 (1h, s), 7.87 (1H, d, J=8.0 Hz), 7.84 (1H, d, j=8.9 Hz), 7.43-7.40 3H, m), 7.29-7.27 (3H, m), 7.21 (1H, dd, J=8.9, 2.5 hz), 6.65 (1H, d, J=2.3 Hz), 3.77 (3H, s), 2.55-2.50 ((1H, m), 2.48-2.43 (1H, m0, 1.61-1.56 (2H, m), 1.26-1.11 (2H, m), 0.71 (3H, t, J=7.4 hz); MS (M+H) 419.

BBr$_3$ (0.53 mL, 0.529 mmole, 3 equiv, 1.0M in methylene chloride) was added dropwise to a solution of 4-5 (74 mg, 0.177 mmole) in methylene chloride (1.5 mL) with stirring under a nitrogen atmosphere at 0° C. After 3 hours, water (1 mL) was added with continued stirred for 10 minutes. The reaction was diluted with ether (100 mL), and then was washed with water (20 mL), then brine (20 mL), and then was dried with MgSO$_4$. After filtering off the drying agent the solvent was removed under reduced pressure and the crude oil was purified on SiO$_2$, eluting with hexanes/ethyl acetate (gradient elution, 0% to 100% ethyl acetate) to give 4-6 as a colorless oil. $^1$H NMR (500 MHz, CDCl$_3$) 8.32 (1H, s), 7.87-7.84 (2H, m), 7.39-7.29 (3H, m), 7.27 (1H, d, J=1 Hz), 7.22 (1H, d, J=8.2 Hz), 7.14-7.12 (2H, m), 6.69 (1H, d, J=1.9 Hz), 2.47-2.38 (2H, m), 1.52-1.45 (2H, m), 1.09-1.04 (2H, m), 0.61 (3H, t=7.3 Hz); MS (M+H) 405.

A slurry of 4-6 (23 mg, 0.057 mmole), ethyl bromoacetate (7 mg, 0.057 mmole, 1 equiv), and Cs$_2$CO$_3$ (30 mg, 1.2 equiv) was stirred at room temperature in DMF (0.3 mL) under an atmosphere of nitrogen. After 2 hours the reaction was diluted with ether (100 mL). The ether was washed with water (3×20 mL), then brine (20 mL), and then was dried with MgSO$_4$. After filtering off the drying agent the solvent was removed under reduced pressure, and the crude oil was purified on SiO$_2$, eluting with hexanes/ethyl acetate (gradient elution, 0% to 100% ethyl acetate) to give 4-7 as a colorless oil. $^1$H NMR (500 MHz, CDCl$_3$) 8.33 (1H, s), 7.90 (2H, d, J=9 Hz), 7.48-7.43 (3H, m), 7.33-7.29 (4H, m), 6.64 (1H, d, J=2.6 Hz), 4.58 (2H, s), 4.26 (2H, q, J=7.1 Hz), 2.55-2.41 (2H, m), 1.62-1.54 (2H, m), 1.30 (3H, t, J=7.1 Hz), 1.17-1.11 (2H, m), 0.72 (3H, t, J=7.3 Hz); MS (M+H) 491.

A solution of 4-7 (25 mg, 0.051 mmole) in methanol/THF (1:1, 0.45 mL) was treated with 1N NaOH (1.2 equiv). After 18 hours, the reaction was neutralized with HCl and then was diluted with ether (100 mL). The ether was washed with water (20 mL), then brine (20 mL), and then was dried with MgSO$_4$. After filtering off the drying agent, the solvent was removed under reduced pressure and the crude oil was purified by prep TLC (20 cm×20 cm plate, SiO2, 1000 microns, hexanes/ethyl acetate/HOAc, 7:3:0.1) to give 4-8 as a solid. $^1$H NMR (500 MHz, CDCl$_3$) 8.37 (1H, br s), 7.89-7.86 (2H, m), 7.46-7.40 (3H, m), 7.31-7.25 (4H, m), 6.61 (1H, br s), 4.61 (2H, br s), 2.52-2.4 (2H, m), 1.12-1.06 (2H, m), 0.67 (3H, t, J=7.1 Hz); MS (M+H) 463.

What is claimed is:

1. A compound of formula I:

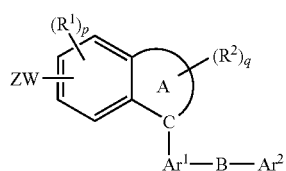

I or a pharmaceutically acceptable salt thereof, wherein:

Ring A is a 5- or 6-membered heteroaromatic ring having 1-2 heteroatoms independently selected from O and N, wherein Ring A together with the phenyl ring to which ring A is fused forms a benzoheteroaromatic ring;

Ar$^1$ and Ar$^2$ are each carbocyclic or heterocyclic aromatic groups which are independently selected from the group consisting of phenyl and pyridine, said aromatic groups being optionally substituted with 1-4 substituent groups independently selected from halogen, —C$_1$-C$_6$ alkyl, —C$_2$-C$_6$ alkenyl, —C$_2$-C$_6$ alkynyl, —OC$_1$-C$_6$ alkyl, —OC$_2$-C$_6$ alkenyl, —C(=O)C$_1$-C$_6$ alkyl, —S(O)$_n$C$_1$-C$_6$ alkyl, C$_3$-C$_7$ cycloalkyl, —OC$_3$-C$_7$ cycloalkyl, —NO$_2$, and —CN, wherein —C$_1$-C$_6$ alkyl, —C$_2$-C$_6$ alkenyl, —C$_2$-C$_6$ alkynyl, —OC$_1$-C$_6$ alkyl, —OC$_2$-C$_6$ alkenyl, —C(=O)C$_1$-C$_6$ alkyl, —S(O)$_n$C$_1$-C$_6$ alkyl, C$_3$-C$_7$ cycloalkyl, and —OC$_3$-C$_7$ cycloalkyl are each optionally substituted with 1-5 halogens;

B is selected from the group consisting of —O—, —S(O)$_n$—, —N(R$^3$)—, —C(=O)—, and —C(R$^4$)$_2$—, —WZ is selected from the group consisting of —O—C(R$^5$)(R$^6$)—Z, —S(O)$_n$—C(R$^5$)(R$^6$)—Z, and —CH$_2$—C(R$^5$)(R$^6$)—Z;

Z is selected from the group consisting of —CO$_2$R$^7$ and tetrazole;

R$^1$ and R$^2$ are each independently selected from the group consisting of halogen, —CN, —NO$_2$, —OH, —C$_1$-C$_5$ alkyl, —OC$_1$-C$_5$ alkyl, —C(=O)C$_1$-C$_5$ alkyl, —S(O)$_n$C$_1$-C$_5$alkyl, and C$_{3-6}$ cycloalkyl, wherein C$_1$-C$_5$ alkyl, —OC$_1$-C$_5$ alkyl, —C(=O)C$_1$-C$_5$ alkyl, —S(O)$_n$C$_1$-C$_5$alkyl, and C$_{3-6}$ cycloalkyl are optionally substituted with 1-5 halogens;

R$^3$ is selected from the group consisting of H and C$_1$-C$_5$ alkyl;

each R$^4$ is independently selected from the group consisting of H, halogen, and —C$_1$-C$_5$ alkyl, wherein —C$_1$-C$_5$ alkyl is optionally substituted with 1-5 halogens;

R$^5$ and R$^6$ are each independently selected from the group consisting of H, halogen, —C$_1$-C$_5$ alkyl, —OC$_1$-C$_5$ alkyl, —C$_2$-C$_5$ alkenyl, —OC$_2$-C$_5$ alkenyl, C$_{3-6}$ cycloalkyl, —(CH$_2$)$_m$phenyl, and —O(CH$_2$)$_m$phenyl, wherein —C$_1$-C$_5$ alkyl, —OC$_1$-C$_5$ alkyl, —C$_2$-C$_5$ alkenyl, and —OC$_2$-C$_5$ alkenyl are optionally substituted with 1-5 halogens, and wherein C$_{3-6}$ cycloalkyl and the phenyl of —(CH$_2$)$_m$phenyl and —O(CH$_2$)$_m$phenyl are optionally substituted with 1-5 groups independently selected from halogen, C$_1$-C$_3$ alkyl and —OC$_1$-C$_3$ alkyl, said C$_1$-C$_3$ alkyl and —OC$_1$-C$_3$ alkyl being optionally substituted with 1-3 halogens; or alternatively R$^5$ and R$^6$ may be joined to form a C$_3$-C$_6$ cycloalkyl group, said C$_3$-C$_6$ cycloalkyl group optionally being substituted with 1-3 halogens;

R$^7$ is selected from the group consisting of H and —C$_1$-C$_6$ alkyl, wherein C$_1$-C$_6$ alkyl is optionally substituted with 1-5 halogens;

m in each instance is an integer from 0-2;

n in each instance is an integer from 0-2;

p is an integer from 0 to 3; and q is an integer from 0-3.

2. A compound in accordance with claim 1 or a pharmaceutically acceptable salt thereof, wherein Ring A together with the phenyl ring to which ring A is fused forms a benzoheteroaromatic ring selected from the group consisting of benzisoxazolyl.

3. A compound in accordance claim 2, or a pharmaceutically acceptable salt thereof, wherein:

Ring A together with the phenyl ring to which ring A is fused forms a benzoheteroaromatic ring selected from the group consisting of benzisoxazolyl;

Ar$^1$ is selected from the group consisting of phenyl and pyridinyl, and Ar$^2$ is selected from the group consisting of phenyl, wherein Ar$^1$ and Ar$^2$ are each optionally substituted with 1-4 substituent groups independently selected from halogen, —C$_1$-C$_4$ alkyl, —OC$_1$-C$_4$ alkyl, —S(O)$_n$C$_1$-C$_4$ alkyl, —NO$_2$, and —CN, wherein —C$_1$-C$_4$ alkyl, —OC$_1$-C$_4$ alkyl, and —S(O)$_n$C$_1$-C$_4$ alkyl are each optionally substituted with 1-3 halogens;

B is selected from —O— and —C(=O)—;

—WZ is —O—C(R$^5$)(R$^6$)—CO$_2$R$^7$;

R$^1$ and R$^2$ are each independently selected from the group consisting of halogen, —OH, —CN, —NO$_2$, —C$_1$-C$_3$ alkyl, —OC$_1$-C$_3$ alkyl, —S(O)$_2$CH$_3$, and —S(O)$_2$CF$_3$, wherein —C$_1$-C$_3$ alkyl and —OC$_1$-C$_3$ alkyl are optionally substituted with 1-3 halogens;

R$^5$ and R$^6$ are each independently selected from the group consisting of H, halogen, and —C$_1$-C$_4$ alkyl, wherein —C$_1$-C$_4$ alkyl is optionally substituted with 1-5 halogens;

R$^7$ is selected from the group consisting of H and C$_1$-C$_6$ alkyl, wherein C$_1$-C$_6$ alkyl is optionally substituted with 1-5 halogens;

n is an integer from 0-2;

p is an integer from 0 to 2; and q is an integer from 0-2.

4. A compound in accordance with claim 3, or a pharmaceutically acceptable salt thereof, wherein:

Ring A together with the phenyl ring to which ring A is fused forms a benzoheteroaromatic ring selected from the group consisting of benzisoxazolyl;

Ar$^1$ is selected from the group consisting of phenyl and pyridinyl, and is optionally substituted with 1-2 groups which are independently selected from C$_1$-C$_4$ alkyl, wherein C$_1$-C$_4$ alkyl is optionally substituted with 1-3 halogens;

Ar$^2$ is phenyl, which is optionally substituted with 1-2 substituent groups independently selected from halogen, —CN, —C$_1$-C$_3$ alkyl, and —OC$_1$-C$_3$ alkyl, wherein —C$_1$-C$_3$ alkyl and —OC$_1$-C$_3$ alkyl are optionally substituted with 1-3 halogens;

B is —O—;

—WZ is —O—C(R$^5$)(R$^6$)—CO$_2$H;

each R$^1$ is independently selected from the group consisting of halogen, —C$_1$-C$_3$ alkyl, and —OH, wherein —C$_1$-C$_3$ alkyl is optionally substituted with 1-3 halogens;

each R$^2$ is independently selected from the group consisting of —C$_1$-C$_3$ alkyl, —S(O)$_2$CH$_3$, and —S(O)$_2$CF$_3$, wherein —C$_1$-C$_3$ alkyl is optionally substituted with 1-3 halogens;

R$^5$ and R$^6$ are each independently H or —C$_1$-C$_3$ alkyl;

p is an integer from 0-2; and q is an integer from 0-2.

5. A compound in accordance with claim 1 having Formula II

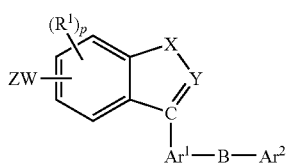

or a pharmaceutically acceptable salt thereof, wherein:

X—Y is selected from the group consisting of —O—N.

6. A compound in accordance with claim 5, or a pharmaceutically acceptable salt thereof, wherein:

Ar$^1$ is selected from the group consisting of phenyl and pyridinyl, and is optionally substituted with 1-2 groups which are independently selected from C$_1$-C$_4$ alkyl, wherein C$_1$-C$_4$ alkyl is optionally substituted with 1-3 halogens;

Ar$^2$ is phenyl, which is optionally substituted with 1-2 substituent groups independently selected from halogen, —CN, —C$_1$-C$_3$ alkyl, and —OC$_1$-C$_3$ alkyl, wherein —C$_1$-C$_3$ alkyl and —OC$_1$-C$_3$ alkyl are optionally substituted with 1-3 halogens;

B is selected from —O— and —C(=O)—;

—WZ is —O—C(R$^5$)(R$^6$)—CO$_2$R$^7$;

each R$^1$ is independently selected from the group consisting of halogen, —C$_1$-C$_3$ alkyl, —OC$_1$-C$_3$ alkyl, and —OH, wherein —C$_1$-C$_3$ alkyl and —OC$_1$-C$_3$ alkyl are optionally substituted with 1-3 halogens;

each R$^2$ is independently selected from the group consisting of H, —C$_1$-C$_3$ alkyl, —S(O)$_2$CH$_3$, and —S(O)$_2$CF$_3$, wherein —C$_1$-C$_3$ alkyl is optionally substituted with 1-3 halogens;

R$^5$ and R$^6$ are each independently selected from the group consisting of H and C$_1$-C$_3$ alkyl, wherein —C$_1$-C$_3$ alkyl is optionally substituted with 1-5 halogens;

R$^7$ is H or —C$_1$-C$_5$ alkyl; and p is an integer from 0-2.

7. A compound in accordance with claim 6 having Formula III

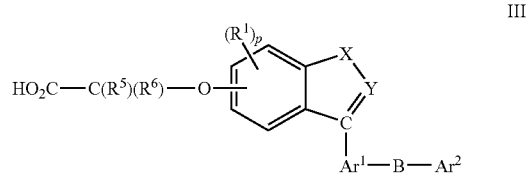

or a pharmaceutically acceptable salt thereof, wherein:

X—Y is selected from the group consisting of —O—N=,

Ar$^1$ is selected from the group consisting of phenyl and pyridinyl, wherein Ar$^1$ is optionally substituted with a —C$_2$-C$_4$ alkyl group, which is optionally substituted with 1-3 F;

each R$^1$ is independently selected from the group consisting of halogen, CH$_3$, —CF$_3$, —OH, —OCH$_3$, and —OCF$_3$;

R$^2$ is selected from the group consisting of H, —C$_1$-C$_3$ alkyl, —CF$_3$, —S(O)$_2$CH$_3$, and —S(O)$_2$CF$_3$;

R$^5$ is H or —C$_1$-C$_3$ alkyl; and

R$^6$ is —C$_1$-C$_3$ alkyl.

8. A compound in accordance with claim 7, or a pharmaceutically acceptable salt thereof, wherein Ar$^1$ is selected from the group consisting of phenyl, and pyridinyl, wherein pyridinyl is connected at the 3-position to the C-atom of the ring A to which Ar$^1$ is connected, and Ar$^1$ is substituted with one —C$_2$-C$_4$ alkyl substituent which is optionally substituted with 1-3 F;

Ar$^2$ is phenyl, which is optionally substituted with 1-2 substituent groups independently selected from halogen, —CN, —C$_1$-C$_2$ alkyl, —CF$_3$, —OCH$_3$, and —OCF$_3$;

B is —O—;

each R$^1$ is independently selected from the group consisting of halogen, —CH$_3$, —CF$_3$, and —OH;

R² is selected from the group consisting of H, —CH₃, —CF₃, —S(O)₂CH₃, and —S(O)₂CF₃;
R⁵ is H or —CH₃; and
R⁶ is —C₁-C₃ alkyl.

9. A compound in accordance with claim 8 having Formula IV

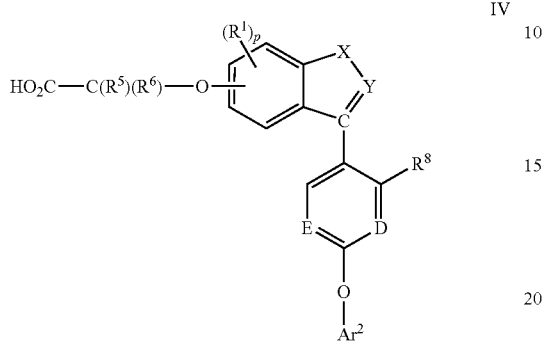

or a pharmaceutically acceptable salt thereof, wherein:
D and E are each independently selected from —CH═ and —N═; and
R⁸ is —C₂-C₄ alkyl, which is optionally substituted with 1-3 F.

10. A compound in accordance with claim 9 having Formula V

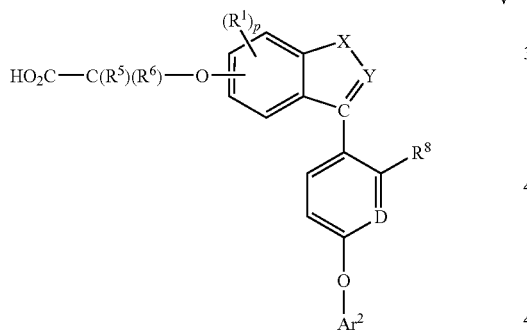

or a pharmaceutically acceptable salt thereof, wherein:
D is selected from —CH═ and —N═; and
R⁸ is —C₂-C₄ alkyl.

11. A compound in accordance with claim 10 having Formula V, or a pharmaceutically acceptable salt thereof, wherein
R⁸ is is n-propyl;
R² is H, —CH₃, or —S(O)₂CH₃; and
R⁶ is C₁-C₂ alkyl.

12. A compound of claim 11, or a pharmaceutically acceptable salt thereof, wherein X—Y is —O—N═; and D is —N═.

13. A pharmaceutical composition comprising a compound in accordance with claim 1, or a pharmaceutically acceptable salt thereof, and a pharmaceutically acceptable carrier.

14. A compound in accordance with claim 3 or a pharmaceutically acceptable salt thereof, wherein the structure is selected from the group consisting of:

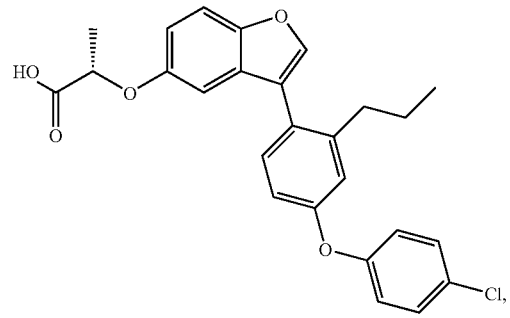

(1)

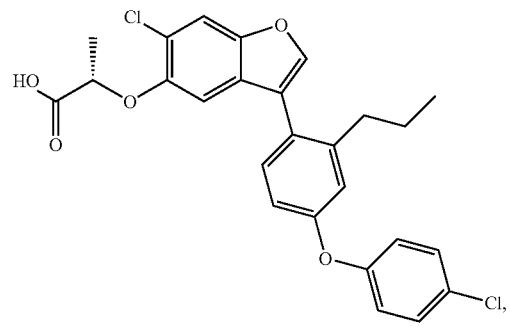

(2)

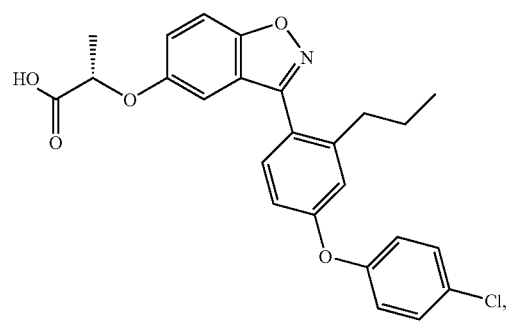

(3)

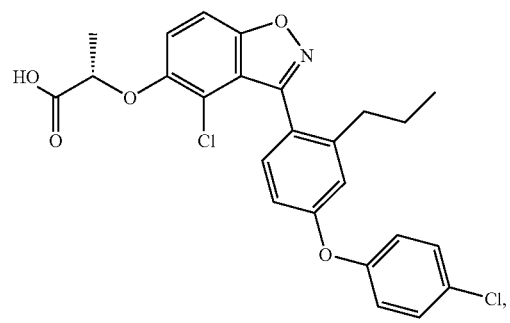

(4)

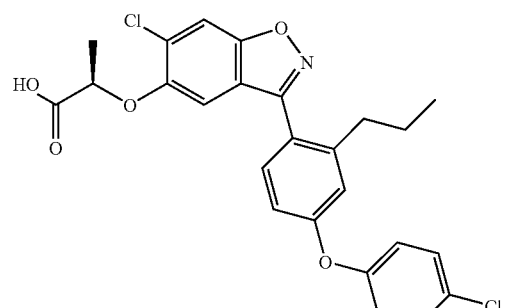

(5)

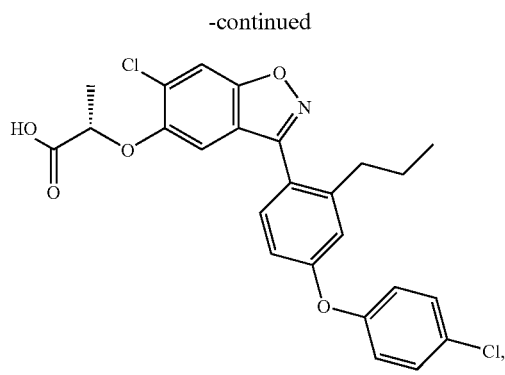
(6)
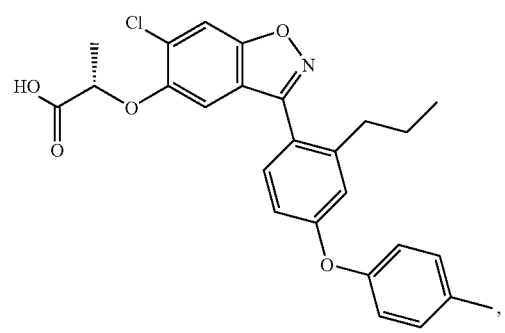
(7)
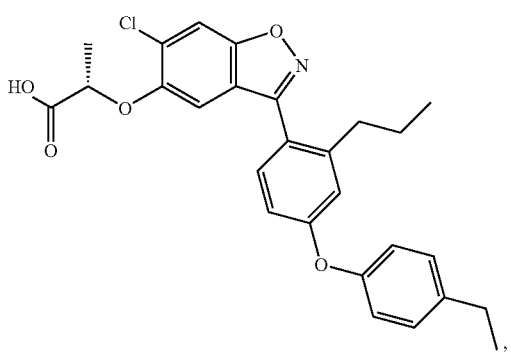
(8)
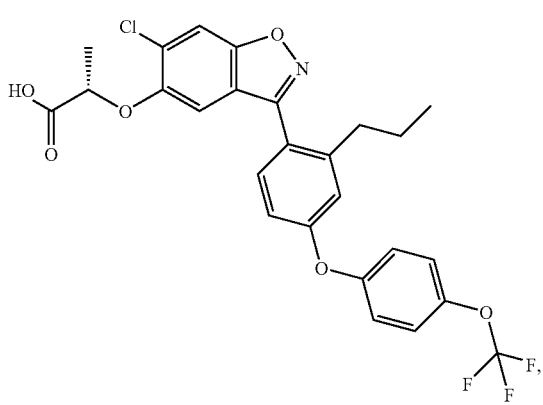
(9)
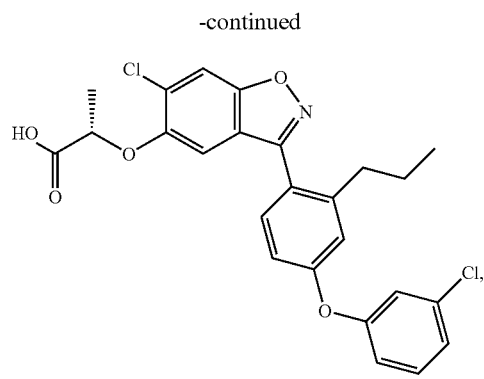
(10)
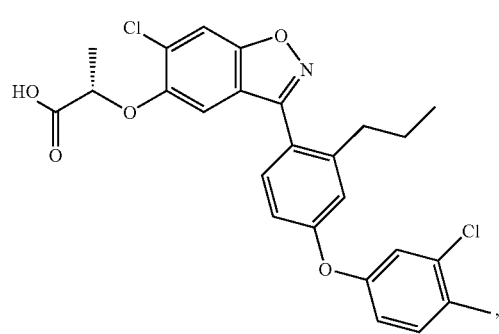
(11)
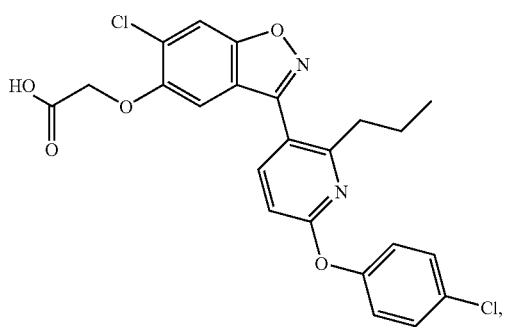
(12)
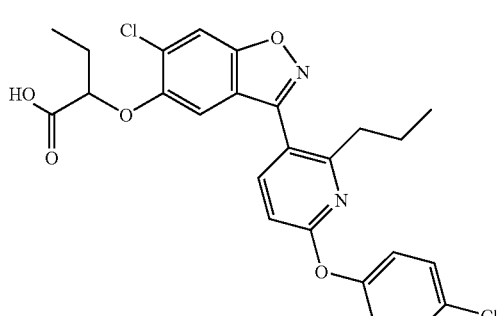
(13)

(14) 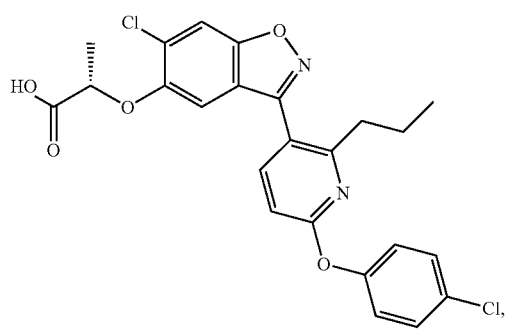
(15) 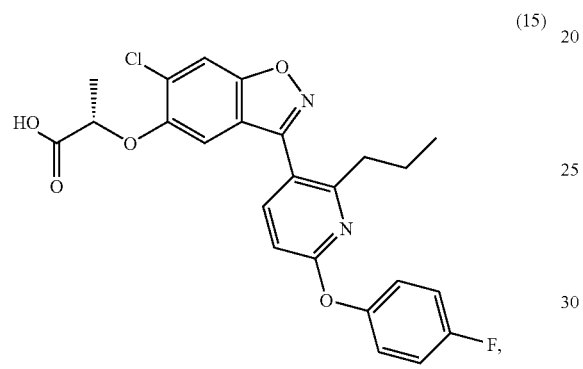
(16) 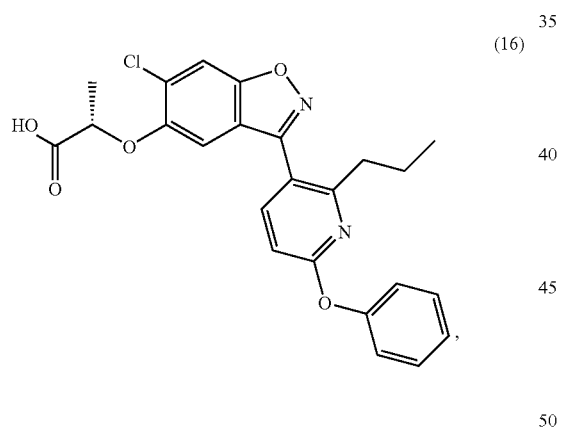
(17) 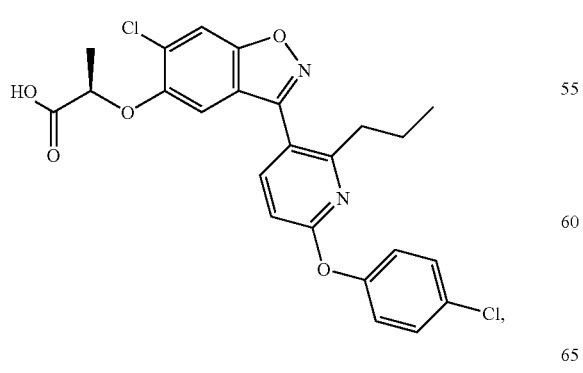
(18) 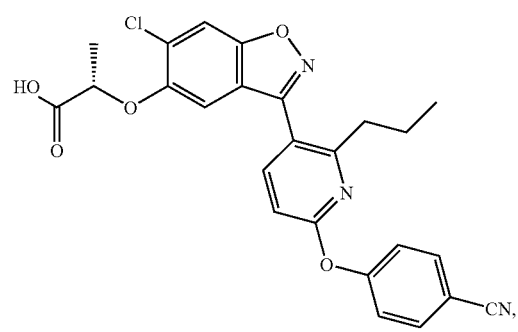
(19) 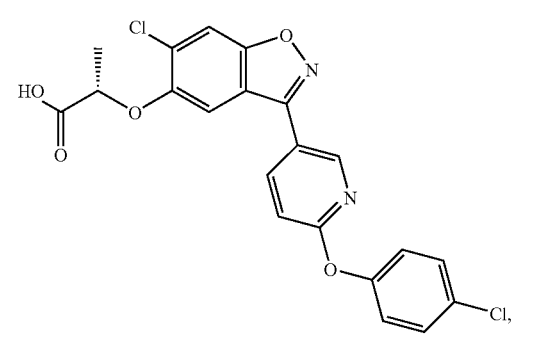
(20) 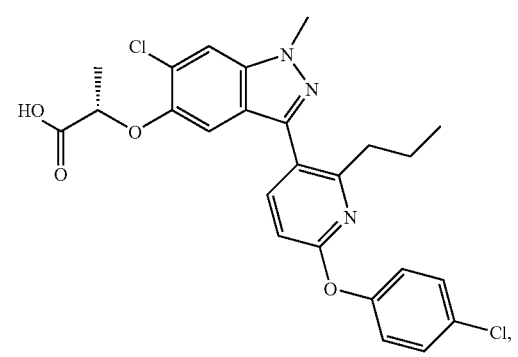
(21) 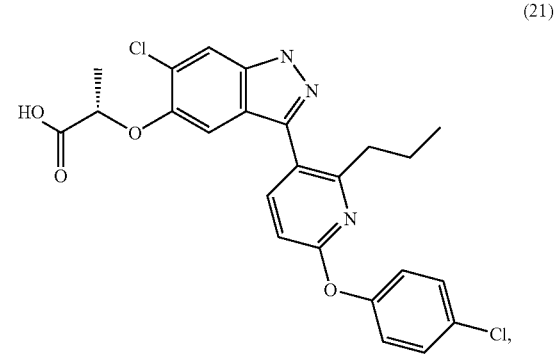

-continued

(22)
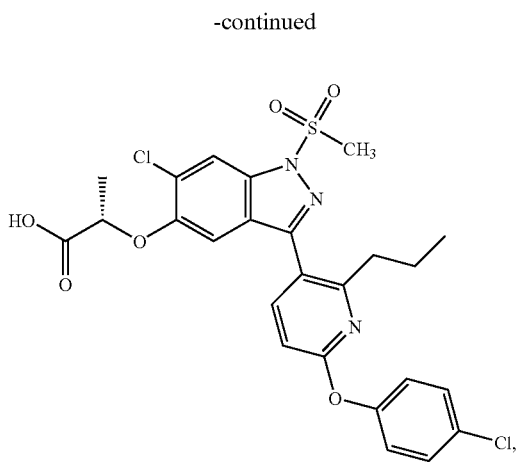

(2-8)
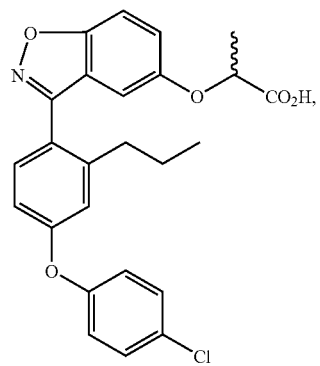

(2-9)
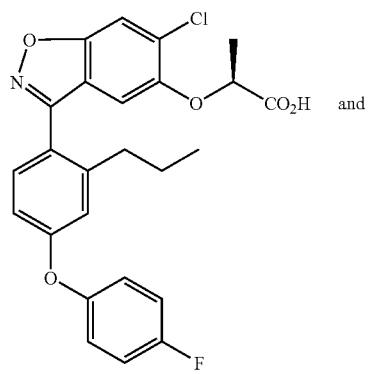
and

-continued (2-10)
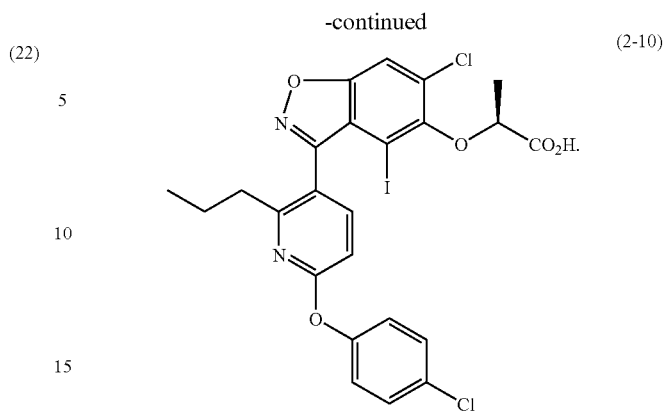

15. A method for treating non-insulin dependent (Type 2) diabetes mellitus in a patient in need of such treatment which comprises administering to said patient a therapeutically effective amount of a compound of claim 1, or a pharmaceutically acceptable salt thereof.

16. A pharmaceutical composition comprising:
   (1) a compound of claim 1, or a pharmaceutically acceptable salt thereof;
   (2) one or more compounds selected from the group consisting of:
      (a) PPAR gamma agonists and partial agonists;
      (b) biguanides;
      (c) protein tyrosine phosphatase-1B (PTP-1B) inhibitors;
      (d) dipeptidyl peptidase IV (DP-IV) inhibitors;
      (e) insulin or an insulin mimetic;
      (f) sulfonylureas;
      (g) α-glucosidase inhibitors;
      (h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) niacin receptor agonists, (v) PPARα agonists, (vi) cholesterol absorption inhibitors, (vii) acyl CoA:cholesterol acyltransferase (ACAT) inhibitors, (viii) CETP inhibitors, and (ix) phenolic anti-oxidants;
      (i) PPAR α/γ dual agonists,
      (j) PPARδ agonists,
      (k) antiobesity compounds,
      (l) ileal bile acid transporter inhibitors;
      (m) anti-inflammatory agents;
      (n) glucagon receptor antagonists;
      (o) GLP-1;
      (p) GIP-1; and
      (q) GLP-1 analogs, and pharmaceutically acceptable salts of these compounds; and
   (3) a pharmaceutically acceptable carrier.

* * * * *